United States Patent
Meyyappan et al.

(10) Patent No.: US 10,406,367 B2
(45) Date of Patent: Sep. 10, 2019

(54) TRANSVASCULAR DIAPHRAGM PACING SYSTEM AND METHODS OF USE

(71) Applicant: Lungpacer Medical, Inc., Burnaby (CA)

(72) Inventors: Ramasamy Meyyappan, Burnaby (CA); Joaquin Andres Hoffer, Anmore (CA); Marcelo Baru, Tualatin, OR (US); Bernard Coquinco, Richmond (CA); Rodrigo Andres Sandoval, Vancouver (CA); Jessica Kit-Sum Tang, Thunder Bay (CA)

(73) Assignee: Lungpacer Medical Inc., Burnaby (CA)

(*) Notice: Subject to any disclaimer, the term of this patent is extended or adjusted under 35 U.S.C. 154(b) by 0 days.

(21) Appl. No.: 16/111,644

(22) Filed: Aug. 24, 2018

(65) Prior Publication Data

US 2018/0361148 A1    Dec. 20, 2018

Related U.S. Application Data

(63) Continuation of application No. 14/410,022, filed as application No. PCT/CA2013/000594 on Jun. 21, 2013.

(Continued)

(51) Int. Cl.
*A61N 1/36* (2006.01)
*A61M 16/00* (2006.01)
(Continued)

(52) U.S. Cl.
CPC .............. *A61N 1/3611* (2013.01); *A61B 5/08* (2013.01); *A61M 16/00* (2013.01);
(Continued)

(58) Field of Classification Search
None
See application file for complete search history.

(56) References Cited

U.S. PATENT DOCUMENTS

| | | |
|---|---|---|
| 1,693,734 A | 12/1928 | Waggoner |
| 2,532,788 A | 12/1950 | Sarnoff |

(Continued)

FOREIGN PATENT DOCUMENTS

| | | |
|---|---|---|
| CN | 1652839 A | 8/2005 |
| CN | 102143781 A | 8/2011 |

(Continued)

OTHER PUBLICATIONS

Escher, Doris J.W. et al., "Clinical Control of Respiration by Transvenous Phrenic Pacing," American Society for Artificial Internal Organs: Apr. 1968—vol. 14—Issue 1—pp. 192-197.

(Continued)

*Primary Examiner* — Brian T Gedeon
(74) *Attorney, Agent, or Firm* — Bookoff McAndrews, PLLC

(57) ABSTRACT

Transvascular diaphragm pacing systems (TDPS) and methods are disclosed for providing respiratory therapy to a patient. The TDPS can provide rapid insertion and deployment of endovascular pacing electrodes in critically ill patients who require intubation and invasive PPMV in order to support the physiological requirements of the human ventilatory system. The systems and methods make best use of the contractile properties of the diaphragm muscle and prevent muscle disuse and muscle atrophy. This can be carried out by engaging the phrenic nerves using patterned functional electrical stimulation applied to endovascular electrodes that are temporarily and reversibly inserted in central veins of the patient, such as the left subclavian vein and the superior vena cava. The TDPS can be designed to seamlessly interface with any commercially available posi- (Continued)

tive-pressure ventilatory assistance/support equipment such as is commonly in use in hospital intensive care units (ICU) for treating critically ill patients with breathing insufficiencies, pain, trauma, sepsis or neurological diseases or deficits.

17 Claims, 35 Drawing Sheets

Related U.S. Application Data

(60) Provisional application No. 61/662,579, filed on Jun. 21, 2012.

(51) Int. Cl.
*A61B 5/08* (2006.01)
*A61N 1/05* (2006.01)

(52) U.S. Cl.
CPC ...... *A61M 16/0069* (2014.02); *A61M 16/026* (2017.08); *A61N 1/056* (2013.01); *A61N 1/0551* (2013.01); *A61N 1/3601* (2013.01); *A61N 1/36139* (2013.01); A61M 2016/0024 (2013.01); A61M 2205/054 (2013.01); A61M 2230/60 (2013.01)

(56) References Cited

U.S. PATENT DOCUMENTS

| | | |
|---|---|---|
| 2,664,880 A | 1/1954 | Wales, Jr. |
| 3,348,548 A | 10/1967 | Chardack |
| 3,470,876 A | 10/1969 | John |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | McCormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | Dimarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |

(56) References Cited

U.S. PATENT DOCUMENTS

| | | |
|---|---|---|
| 6,236,892 B1 | 5/2001 | Feler |
| 6,240,320 B1 | 5/2001 | Spehr et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | McDaniel |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,167,751 B1 | 1/2007 | Whitehurst et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van Venrooij et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,809,442 B2 * | 10/2010 | Bolea .................. A61N 1/0556 607/42 |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |

(56) References Cited

U.S. PATENT DOCUMENTS

| | | |
|---|---|---|
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1 | 8/2013 | Kornet et al. |
| 8,509,901 B2 | 8/2013 | Tehrani |
| 8,509,902 B2 | 8/2013 | Cho et al. |
| 8,509,919 B2 | 8/2013 | Yoo et al. |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | McCabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 * | 3/2014 | Ignagni .................. A61N 1/05 128/204.18 |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,149,642 B2 | 10/2015 | McCabe et al. |
| 9,168,377 B2 | 10/2015 | Hoffer |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,474,894 B2 | 10/2016 | Mercanzini et al. |
| 9,485,873 B2 | 11/2016 | Shah et al. |
| 9,498,625 B2 | 11/2016 | Bauer et al. |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,396 B2 | 5/2018 | Young et al. |
| 9,968,785 B2 | 5/2018 | Hoffer et al. |
| 9,968,786 B2 | 5/2018 | Bauer et al. |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0195571 A1 | 10/2003 | Burnes et al. |
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | McCreery |
| 2004/0186543 A1 | 9/2004 | King et al. |

(56) References Cited

U.S. PATENT DOCUMENTS

| | | |
|---|---|---|
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0121231 A1 | 5/2008 | Sinderby et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2010/0022950 A1 | 1/2010 | Anderson et al. |
| 2010/0036451 A1 | 2/2010 | Hoffer |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0060381 A1 | 3/2011 | Ignagni et al. |
| 2011/0077726 A1 | 3/2011 | Westlund et al. |
| 2011/0093032 A1 | 4/2011 | Boggs, II et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1* | 11/2011 | Tehrani .............. A61N 1/3601 607/42 |
| 2012/0035684 A1 | 2/2012 | Thompson et al. |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |

(56) References Cited

U.S. PATENT DOCUMENTS

| | | |
|---|---|---|
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0202448 A1 | 7/2015 | Hoffer et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De La Rama et al. |
| 2015/0374991 A1 | 12/2015 | Morris et al. |
| 2016/0001072 A1 | 1/2016 | Gelfand et al. |
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | McFarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |

FOREIGN PATENT DOCUMENTS

| | | |
|---|---|---|
| EP | 0993840 A1 | 4/2000 |
| EP | 1304135 A2 | 4/2003 |
| EP | 0605796 B1 | 8/2003 |
| EP | 2489395 A1 | 8/2012 |
| FR | 2801509 A1 | 6/2001 |
| JP | H08510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | WO-9407564 A2 | 4/1994 |
| WO | WO-9508357 A1 | 3/1995 |
| WO | WO-9964105 A1 | 12/1999 |
| WO | WO-9965561 A1 | 12/1999 |
| WO | WO-0100273 A1 | 1/2001 |
| WO | WO-02058785 A1 | 8/2002 |
| WO | WO-03094855 A1 | 11/2003 |
| WO | WO-2006110338 A1 | 10/2006 |
| WO | WO-2006115877 A1 | 11/2006 |
| WO | WO-2007053508 A1 | 5/2007 |
| WO | WO-2008092246 A1 | 8/2008 |
| WO | WO-2008094344 A1 | 8/2008 |
| WO | WO-2009006337 A1 | 1/2009 |
| WO | WO-2009134459 A2 | 11/2009 |
| WO | WO-2010029842 A1 | 3/2010 |
| WO | WO-2010148412 A1 | 12/2010 |
| WO | WO 2011/094631 A1 | 8/2011 |
| WO | WO-2011158410 A1 | 12/2011 |
| WO | WO-2012106533 A2 | 8/2012 |
| WO | WO-2013131187 A1 | 9/2013 |
| WO | WO-2013188965 A1 | 12/2013 |
| WO | WO 2014/008171 A1 | 1/2014 |

OTHER PUBLICATIONS

Ishii, K. et al., "Effects of Bilateral Transvenous Diaphragm Pacing on Hemodynamic Function in Patients after Cardiac Operations," J. Thorac. Cardiovasc. Surg., 1990.

Antonica A., et al., "Vagal Control of Lymphocyte Release from Rat Thymus," Journal of the Autonomic Nervous System, Elsevier, vol. 48(3), Aug. 1994, pp. 187-197.

Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikovaa L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.

Borovikovaa L.V., et al., "Vagus Nerve Stimulation Attenuates the Systemic Inflammatory Response to Endotoxin," Nature, Macmillan Magazines Ltd, vol. 405, May 25, 2000, pp. 458-462.

Chinese Search Report for Application No. CN2013/80023357.5, dated Jul. 24, 2015.

Co-pending U.S. Appl. No. 15/606,867, filed May 26, 2017.

Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.

Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.

De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.

Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.

European Search Report for Application No. 13758363, dated Nov. 12, 2015.

European Search Report for Application No. EP17169051.4, dated Sep. 8, 2017, 7 pages.

Extended European Search Report for Application No. 14864542.7, dated Jun. 2, 2017, 8 pages.

Extended European Search Report for Application No. 15740415.3, dated Jul. 7, 2017.

Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.

(56) References Cited

OTHER PUBLICATIONS

Frisch S., "A Feasibility Study of a Novel Minimally Invasive Approach for Diaphragm Pacing," Master of Science Thesis, Simon Fraser University, 2009, p. 148.
Furman, S., "Transvenous Stimulation of the Phrenic Nerves," Journal of Thoracic and Cardiovascular Surgery, 1971, vol. 62 (5), pp. 743-751.
Gaykema R.P.A. et al., "Subdiaphragmatic Vagotomy Suppresses Endotoxin-Induced Activation of Hypothalamic Corticotropin-Releasing Hormone Neurons and Acth Secretion," Endocrinology, the Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Hoffer J.A. et al., "Diaphragm Pacing with Endovascular Electrodes", IFESS 2010—International Functional Electrical Stimulation Society, 15th Anniversary Conference, Vienna, Austria, Sep. 2010.
Japanese Office Action in corresponding Japanese Application No. 2014-560202, dated Dec. 6, 2016, 4 pages.
Japanese Office Action in corresponding Japanese Application No. 2014-560202, dated Oct. 17, 2017, 5 pages.
Kawashima K., et al., "Extraneuronal Cholinergic System in Lymphocytes," Pharmacology & Therapeutics, Elsevier, vol. 86, 2000, pp. 29-48.
Levine S., et al., "Rapid disuse atrophy of diaphragm fibers in mechanically ventilated humans," New England Journal of Medicine, 2008, vol. 358, pp. 1327-1335.
Lung pacer: Therapy, News.< http://lungpacer.com>. Accessed Dec. 27, 2016.
Madretsma, G.S., et al., "Nicotine Inhibits the In-vitro Production of Interleukin 2 and Tumour Necrosis Factor-α by Human Mononuclear Cells," Immunopharmacology, Elsevier, vol. 35 (1), Oct. 1996, pp. 47-51.
Marcy, T.W. et al., "Diaphragm Pacing for Ventilatory Insufficiency," Journal of Intensive Care Medicine, 1987, vol. 2 (6), pp. 345-353.
Meyyappan R., "Diaphragm Pacing during Controlled Mechanical Ventilation: Pre-Clinical Observations Reveal a Substantial Improvement in Respiratory Mechanics", 17th Biennial Canadian Biomechanics Society Meeting, Burnaby, BC, Jun. 6-9, 2012.
Nabutovsky, Y., et al., "Lead Design and Initial Applications of a New Lead for Long-Term Endovascular Vagal Stimulation," PACE, Blackwell Publishing, Inc, vol. 30(1), Jan. 2007, pp. S215-S218.
Notification of Reasons for Rejection and English language translation issued in corresponding Japanese Patent Application No. 2015-517565, dated Mar. 28, 2017, 6 pages.
Onders R.,, "A Diaphragm Pacing as a Short-Term Assist to Positive Pressure Mechanical Ventilation in Critical Care Patients," Chest, Oct. 24, 2007, vol. 132(4), pp. 5715-5728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-To-Wean Intensive Care Unit Patients," Surgical Endoscopy, 2007, vol. 21, pp. 475-479.
Pavlovic D., et al., "Diaphragm Pacing During Prolonged Mechanical Ventilation of the Lungs could Prevent from Respiratory Muscle Fatigue," Medical Hypotheses, vol. 60 (3), 2003, pp. 398-403.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-R413.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sandoval R., "A Catch/Ike Property-Based Stimulation Protocol for Diaphragm Pacing", Master of Science Coursework project, Simon Fraser University, Mar. 2013.
Sarnoff, S.J. et al., "Electrophrenic Respiration," Science, 1948, vol. 108, p. 482.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.
Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.
Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.
Scheinman R.I., et al., "Role of Transcriptional Activation of IκBα in Mediation of Immunosuppression by Glucocorticoids," Science, vol. 270, Oct. 13, 1995, pp. 283-286.
Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.
Steinlein, O., "New Functions for Nicotinic Acetylcholine Receptors?," Behavioural Brain Research, vol. 95, 1998, pp. 31-35.
Sternberg E.M., (Series Editor) "Neural-Immune Interactions in Health and Disease," The Journal of Clinical Investigation, vol. 100 (11), Dec. 1997, pp. 2641-2647.
Sykes., A.P., et al., "An Investigation into the Effect and Mechanisms of Action of Nicotine in Inflammatory Bowel Disease," Inflammation Research, vol. 49, 2000, pp. 311-319.
Toyabe S., et al., "Identification of Nicotinic Acetylcholine Receptors on Lymphocytes in the Periphery as well as Thymus in Mice," Immunology, vol. 92, 1997, pp. 201-205.
Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.
Wanner, A. et al., "Trasvenous Phrenic Nerve Stimulation in Anesthetized Dogs," Journal of Applied Physiology, 1973, vol. 34 (4), pp. 489-494.
Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.
Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.
Whaley K., et al., "C2 Synthesis by Human Monocytes is Modulated by a Nicotinic Cholinergic Receptor," Nature, vol. 293, Oct. 15, 1981, pp. 580-582 (and reference page).
Office Action dated Apr. 1, 2019 in U.S. Appl. No. 16/114,064 (61 pages).

* cited by examiner

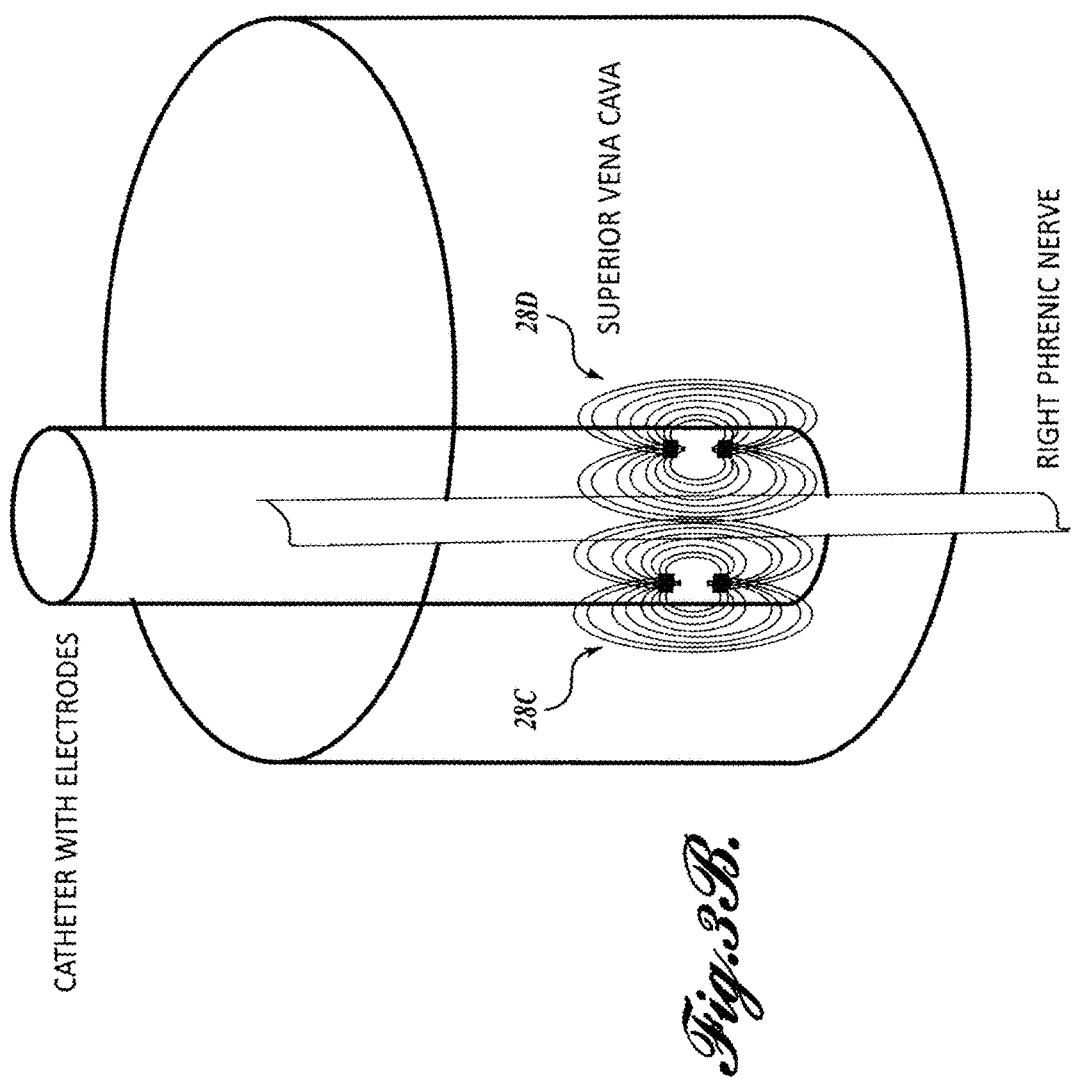

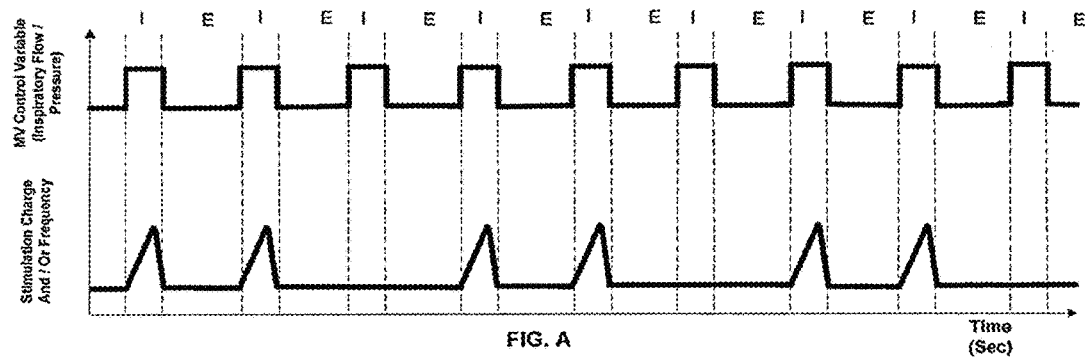
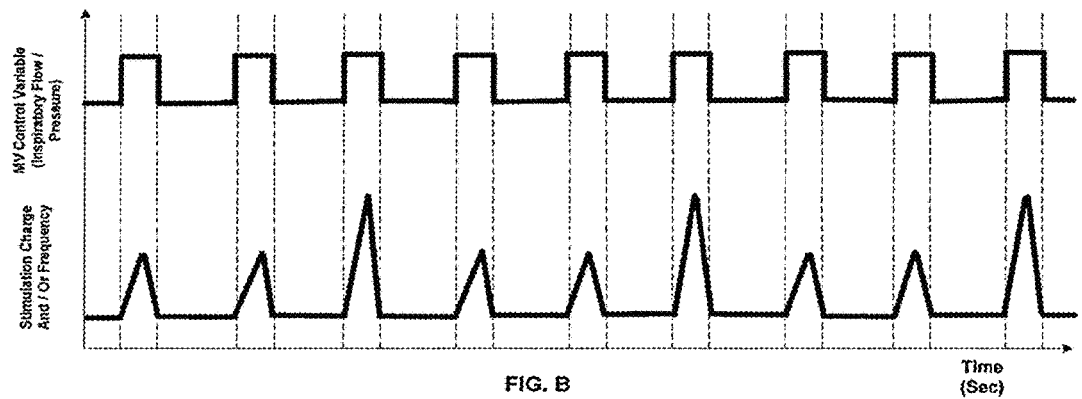
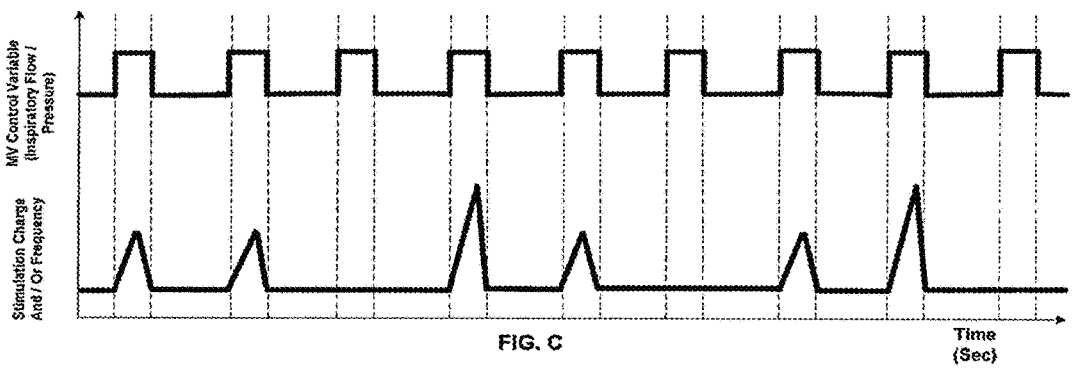
Fig. 13.

ously synchronized to some ventilator breaths, or as a stand-alone system. In some embodiments, the systems and methods may be employed just minutes or hours after first
TRANSVASCULAR DIAPHRAGM PACING SYSTEM AND METHODS OF USE

CROSS-REFERENCE TO RELATED APPLICATION APPLICATIONS

This application is a continuation of U.S. application Ser. No. 14/410,022, filed Dec. 19, 2014, which is a National Stage filing under 35 U.S.C. § 371 of International Application No. PCT/CA2013/000594, filed Jun. 21, 2013, which claims the benefit of U.S. Provisional Application No. 61/662,579, filed Jun. 21, 2012. Each of the disclosures of the above applications is expressly incorporated by reference herein.

BACKGROUND

Patients in hospital Intensive Care Units (ICU) may experience impairment in their ability to breathe volitionally due to their underlying disease condition and require positive pressure mechanical ventilation (PPMV) to provide ventilatory assistance. PPMV is routinely used in combination with sedation in the ICU to provide artificial ventilation for these critically ill individuals. Additionally, many patients undergoing surgery under general anesthesia, for example in hospital Operating Rooms (OR), or procedures under anesthesia or sedation, for example in hospital Emergency Rooms (ER), commonly require PPMV for ventilatory assistance while anesthetized or sedated.

Although mechanical ventilation is a life-sustaining modality, when combined with sedation or anesthesia it interferes with active contraction of the diaphragm. Prolonged totally controlled mechanical ventilation can result in the complete absence of neural activation and mechanical activity of the diaphragm and has been shown to induce muscle atrophy, proteolysis, and reactive oxygen species liberation, leading to rapid loses in diaphragmatic function, a syndrome known as Ventilator-Induced Diaphragmatic Dysfunction (VIDD).

The onset of diaphragm disuse atrophy is rapid, leading to slower patient recovery, which often results in ventilator dependence and translates into higher incidence of ventilator-acquired pneumonia and nosocomial infections, longer stays in the ICU, and escalating hospitalization costs.

In addition to ICU patients, mechanical ventilation is the primary modality of ventilatory assistance for individuals with disease conditions that adversely affect neurological function, such as Spinal Cord Injury (SCI). These individuals may experience impairment in their ability to breathe volitionally due to partial or complete loss of control of the diaphragm, and are prone to lifelong dependence on a mechanical ventilator.

Several viable alternatives to PPMV for assisting breathing are currently available, and have been indicated for use in patients requiring long-term ventilatory assistance such as Spinal Cord Injury (SCI) patients or patients with Congenital Central Hypoventilation Syndrome (CCHS). They include phrenic nerve stimulation and diaphragmatic pacing. These methods use electrical stimulation to induce contraction of the diaphragm using an electrode and an external pacing control box or an implanted pacemaker device.

The two phrenic nerves, which control activation of the diaphragm, run through the thorax, along the left and right sides of the heart, and then to the diaphragm. Phrenic nerve stimulation is performed by electrically stimulating the phrenic nerve to control the patient's diaphragm, which may induce a respiratory cycle. Conventional techniques include surgically implanting a nerve cuff around the phrenic nerve (at the neck or chest level), and then delivering an electrical stimulus from an externally located controller through the cuff to the phrenic nerve. This procedure is quite invasive, requiring incisions when deploying the nerve cuffs, and quite expensive, so it is only selectively used in patients with a life-long requirement for assisted ventilation. In addition, the direct placement of the nerve cuffs around the phrenic nerves may damage the phrenic nerves. These phrenic nerve stimulation systems have not heretofore been prescribed for temporary use in critically ill ICU patients.

Other phrenic nerve stimulation techniques are known, such as that described in U.S. Pat. No. 8,195,297. However, the system disclosed in the '297 patent does to allow for rapid, short term use in an ICU environment for the management of ICU patients particularly in the first few days after start of PPMV.

Another method for electrically stimulating the diaphragm is known as diaphragmatic pacing. Conventionally, diaphragmatic pacing is performed by laparoscopically implanting four electrodes directly on the diaphragm (two on each side), with electrical leads connected to a controller residing external to the body. Conventional diaphragmatic pacing procedures are also quite time consuming and relatively invasive, requiring incisions during implantation, presenting risk during the implantation procedure and risk of chronic infection at the lead entrance sites to the body. Accordingly, these diaphragmatic pacing systems have not heretofore been prescribed for temporary use in critically ill ICU patients.

One such diaphragmatic pacing system is described in U.S. Pat. No. 7,962,215. In addition to being surgically demanding, the diaphragmatic pacing system of the '215 patent is employed to administer therapy to convert Type IIa (fast-type) muscle fibers to Type I (slow-type) muscle fibers in patients who have been ventilated for prolonged periods, whose muscle fibers have all atrophied and converted to Fast-type (VIDD). The therapy described in the '215 patent, however, will not be desirable in the treatment of critical care patients that still have both Type IIa (fast-type) muscle fibers and Type I (slow-type) and will need to have both types to successfully wean off of PPMV.

Accordingly, there exists a need for minimally invasive diaphragm pacing systems and methods for rapid, short term use, as appropriate in the ICU environment, for the management of ICU patients particularly in the first few days or weeks after start of PPMV.

SUMMARY

Examples of systems and methods disclosed herein address this need and others by providing a minimally invasive nerve stimulation system that paces the phrenic nerves transvascularly via disposable endovascular electrodes that can be percutaneously placed under local anesthesia. As will be described in the Detailed Description, such pacing systems and methods can be employed to provide short periods of electrical stimulation for preventing diaphragm disuse atrophy in patients at risk of becoming ventilator-dependent and/or to rehabilitate diaphragm disuse atrophy in ventilator-dependent patients.

The system is designed to work either in conjunction with a mechanical ventilator, causing diaphragmatic contractions in synchrony with each ventilator administered breath, intermittently synchronized to some ventilator breaths, or as a stand-alone system. In some embodiments, the systems and methods may be employed just minutes or hours after first intubation of the subject. Such diaphragm pacing therapy is expected to prevent, reduce or reverse diaphragm disuse atrophy that typically occurs in patients who are on PPMV or are expected to require PPMV and sedation for prolonged periods and by extension, the adverse effects associated with PPMV will be avoided or reduced. As a result, patients may be successfully weaned from PPMV earlier than currently known methods, providing drastic health benefits to patients not to mention substantial reductions in total in-patient costs.

In accordance with one aspect of the present disclosure, a method is provided for administering a treatment plan designed for preventing or reversing diaphragm disuse atrophy in a patient receiving respiratory assistance from a ventilator. The ventilator is employed to provide a breath cycle to the patient, the patient having a prescribed assist level. The method comprises monitoring the breath cycle of the ventilator, administering a pre-programmed stimulation signal to the patient to recruit the phrenic nerve of the patient, and regulating the diaphragm output of the patient for each breath cycle. In some embodiments, the stimulation signal is administered via one or more endovascular electrodes.

In accordance with a first embodiment, the administration of the stimulation signal can occur within a time period, such as 1 hour, 3 hours, 6 hours, 12 hours, 1 day, 3 days, and 1 week, of the patient's first reception of respiratory assistance from the ventilator.

In accordance with a second embodiment, the method also includes obtaining data indicative of at least one of: one or more ventilator breath parameters; one or more pacing parameters; and a prescribed assist level for the patient.

In accordance with a third embodiment, the one or more ventilator breath parameters includes timing data indicative of the duration of a ventilated breath.

In accordance with a fourth embodiment, the method also includes maintaining synchrony between the delivery of the stimulation signal and the ventilator breath cycle.

In accordance with a fifth embodiment, maintaining synchrony includes determining the current breath cycle via data from one or more sensors, and comparing the current breath cycle with the timing data from at least one previous breath cycle.

In accordance with a sixth embodiment, recruitment of the diaphragm provides at least a portion of the prescribed assist level.

In accordance with a seventh embodiment, the method further comprises determining a diaphragm contribution level attributable to the administration of the stimulation signal, wherein the prescribed assist level is the sum of the diaphragm contribution level and a ventilator contribution level.

In accordance with an eight embodiment, the simulation signal includes stimulation signal characteristics that cause the stimulation signal, when delivered to the patient, to satisfy the diaphragm contribution level.

In accordance with a ninth embodiment, the diaphragm contribution level is measured in tidal volume or pressure, individually, in combination, and including components thereof.

In accordance with a tenth embodiment, the prescribed diaphragm contribution level is dependent on the condition of the patient and the contractile capacity and/or functional status of the diaphragm.

In accordance with a eleventh embodiment, determining the contractile capacity includes measuring strength and endurance from the response of the diaphragm to test stimulation patterns.

In accordance with a twelfth embodiment, the condition of the patient and contractile capacity of the diaphragm and/or functional status of the phrenic nerves are assessed prior to the administration of the treatment plan and/or during administration of the treatment plan.

In accordance with a thirteenth embodiment, determining the strength and endurance of the patient's diaphragm includes measuring maximum diaphragm output and fatigue characteristics of the diaphragm.

In accordance with a fourteenth embodiment, monitoring the breath cycle includes sensing breath cycle data via a breath sensor discrete from and interfaced with a breathing circuit of the ventilator and the patient airway, and determining the inspiration phase and the expiration phase of the breath cycle and the duration of each phase from the sensed breath cycle data.

In accordance with a fifteenth embodiment, monitoring the breath cycle further includes determining at least one of the amplitude and rate of change of ventilator output signals for each breath.

In accordance with a sixteenth embodiment, administering a stimulation signal includes generating a stimulation signal in accordance with one or more pacing parameters; and delivering the stimulation signal in relation to a ventilator breath cycle.

In accordance with a seventeenth embodiment, regulating the diaphragm output of the patient for each breath cycle, such as a paced breath cycle, includes monitoring the diaphragm output in response to the last administered stimulation signal; and comparing the diaphragm output of the last administered stimulation signal to a preset target range. Alternatively, the method can skip pacing for one breath cycle (MV-Only), but stimulate the at the next breath cycle (i.e., mechanical ventilation and diaphragm pacing. The method can then compare both of these values and regulate the next paced breath.

In accordance with an eighteenth embodiment, monitoring the diaphragm output in response to the last administered stimulation signal includes sensing diaphragm output data via one or more sensors, wherein the diaphragm output data is indicative of one or more of: air flow, tidal volume, pressure, and/or parameters derived from combinations of flow, tidal volume and/or pressure; and processing the sensed diaphragm data to determine the diaphragm output.

In accordance with a nineteenth embodiment, regulating the diaphragm output of the patient for each breath cycle further includes modifying the stimulation signal to be administered with the next ventilator breath if the diaphragm output of the last administered stimulation signal is outside of the preselected target range.

In accordance with a twentieth embodiment, the preselected target range includes a diaphragm contribution level.

In accordance with a twenty-first embodiment, the method further comprises determining a cause if the diaphragm output of the last administered stimulation signal is outside of the preselected target range.

In accordance with a twenty-second embodiment, if the cause is due to a variation in the respiratory mechanics of the patient, then the condition of the patient's diaphragm and respiratory system during administration of the treatment plan is assessed.

In accordance with a twenty-third embodiment, the method further comprises reprogramming the stimulation signal based on the condition of the assessed diaphragm.

In accordance with a twenty-fourth embodiment, assessing the diaphragm includes monitoring data indicative of flow and pressure of the ventilator breath cycle to determine timing of the end expiration delay; progressively stimulating the diaphragm with stimulating signals based on the monitored data of the ventilator breath cycle; and determining one or more functional characteristics of the diaphragm and respiratory system, wherein the one or more functional characteristics includes one or more of Maximum Static Inspiratory Pressure, Inspiratory Capacity, Work of Breathing, Pressure-Time Product, Pressure-Time Index, Electromyogram (EMG), Maximum Relaxation Rate, and Expiration Time Constant.

In accordance with a twenty-fifth embodiment, the diaphragm stimulation is targeted to take place during each ventilator breath in order to reduce positive pressure and reduce the risk of Ventilator Induced Lung Injury (VILI).

In accordance with a twenty-sixth embodiment, monitoring the breath cycle of the ventilator includes sensing signals indicative of ventilator inspiration and expiration; and calculating one or more of: inspiration phase; expiration phase; inspiration pause; expiration pause.

In accordance with a twenty-seventh embodiment, administering the stimulation signal includes delivery of the stimulation signal contemporaneously with inspiration phase.

In accordance with anther aspect of the present disclosure, a transvascular diaphragm pacing system is provided for preventing or reversing diaphragm disuse atrophy in a patient receiving respiratory assistance from a ventilator. The system comprises at least one endovascular electrode configured to transmit a stimulation signal delivered thereto. The stimulation signal in some embodiments is configured to recruit a phrenic nerve of the patient, the stimulation signal in some embodiments have one or more stimulation parameters. The system also includes one or more sensors configured to sense breath cycle signals from an associated ventilator and diaphragm response from recruitment of the phrenic nerve, and a pulse generator coupled in electrical communication with the at least one endovascular electrode, and at least one input device configured to input data indicative of one or more aspects of a therapy plan. The system further includes a controller coupled in electrical communication with the one or more sensors, the at least one input device, and the pulse generator. The controller is some embodiments is programmed to: receive input data indicative of one or more aspects of the therapy plan, wherein the input data includes sensed signals indicative of ventilator operation and one or more pacing parameters; monitor the breath cycle signals and determine the inspiration phase and expiration phase of the breath cycle; generate the stimulation signal according to the one or more pacing parameters and delivering the generated stimulation signal to the at least one transvascular electrode at a preselected time of the ventilator breath cycle; and regulate the diaphragm output of the patient for each breath cycle.

In accordance with a twenty-eighth embodiment, the controller is further programmed to regulate the diaphragm output of the patient to satisfy a prescribed assist level of the patient.

In accordance with a twenty-ninth embodiment, the controller is further programmed to maintain synchrony of the delivery of the stimulation signal with the ventilator breath cycle.

In accordance with a thirtieth embodiment, the controller is further programmed to: monitor the diaphragm output in response to the last administered stimulation signal; and compare the diaphragm output of the last administered stimulation signal to a preselected target range.

In accordance with a thirty-first embodiment, the controller is programmed to monitor the diaphragm output by sensing diaphragm output data via one of said one or more sensors and processing the sensed diaphragm data to determine the diaphragm output, wherein the diaphragm output includes flow, tidal volume and/or pressure and/or parameters derived from combinations of flow, tidal volume and/or pressure.

In accordance with a thirty-second embodiment, the controller is further programmed to modify the stimulation signal to be administered with the next ventilator breath if the diaphragm output of the last administered stimulation signal is outside a preselected range. Alternatively, the signal could be modified and administered at the next breath with programmed pacing (i.e., a combined breath) as some ventilator breaths may be skipped between stimulations.

In accordance with a thirty-third embodiment, the controller is further programmed to determine a cause if the diaphragm output of the last administered stimulation signal is outside of the preselected target range.

In accordance with a thirty-fourth embodiment, if the controller determines that the cause is due to a variation in the respiratory mechanics of the patient, then the controller is further programmed to assess the condition of the patient's diaphragm and respiratory system during administration of the treatment plan.

In accordance with a thirty-fifth embodiment, the controller is further programmed to reprogram the stimulation signal based on the condition of the assessed diaphragm.

In accordance with a thirty sixth embodiment, the controller is further programmed to assess the diaphragm by monitoring data indicative of flow and pressure of the ventilator breath cycle to determine timing of the end expiration delay, progressively stimulating the diaphragm with stimulating signals based on the monitored data of the ventilator breath cycle, and determining one or more functional characteristics of the diaphragm and respiratory system. In some embodiments, the one or more functional characteristics includes one or more of Maximum Static Inspiratory Pressure, Inspiratory Capacity, Work of Breathing, Pressure-Time Product, Pressure-Time Index, EMG, Maximum Relaxation Rate, and Expiration Time Constant.

In accordance with a thirty-seventh embodiment, the controller is further programmed to determine the readiness to wean from the ventilator based on the assessment of the diaphragm.

In accordance with a thirty-eighth embodiment, the stimulation signal includes a doublet or triplet pulse at the beginning of the stimulation train or in the middle of the simulation train.

In accordance with another aspect of the present disclosure, a method is provided for preventing respiratory disuse atrophy in a patient who is attached to a mechanical ventilator and receiving artificial breath cycle respiratory assistance and sedation. The method comprises placing a first electrode in the patient's vasculature in proximity to the left phrenic nerve, placing at second electrode in the patient's vasculature in proximity to the right phrenic nerve, and within hours of attaching the patient to the ventilator, delivering a pre-programmed stimulation signal to the first and second electrodes in order to stimulate the diaphragm in synchrony with the ventilator breath cycle.

In accordance with a thirty-ninth embodiment, within hours includes one of the following: within twelve hours; within six hours, within five hours; within four hours, within three hours; and within one hour.

In accordance with a yet another aspect of the present disclosure, a method is provided for administering a treatment plan for preventing or speeding up reversal of diaphragm disuse atrophy in a patient receiving respiratory assistance from a ventilator. The ventilator provides a breath cycle to the patient and the patient has a prescribed assist level. The method comprises storing a measurement value indicative of a preselected range of diaphragm output, wherein the diaphragm output is at least a portion of the prescribed assist level, monitoring the breath cycle of the ventilator, administering a stimulation signal to the patient in synchrony with the breath cycle of the ventilator to recruit the diaphragm of the patient, the recruitment of the diaphragm causing a level of diaphragm output, and regulating the diaphragm output of the patient attributable to phrenic recruitment for each stimulated breath cycle in order to fall within the preselected range of diaphragm output.

In accordance with a fortieth embodiment, regulating the diaphragm output of the patient for each breath cycle includes monitoring the diaphragm output in response to the last administered stimulation signal, and comparing the diaphragm output of the last administered stimulation signal to the preselected range of diagram output.

In accordance with a forty-first embodiment, monitoring the diaphragm output in response to the last administered stimulation signal includes sensing diaphragm output data via one or more sensors, and processing the sensed diaphragm output data to determine the diaphragm output. In some embodiments, the diaphragm output includes one or more of: air flow, tidal volume, pressure, and/or parameters derived from combinations of flow, tidal volume and/or pressure.

In accordance with a forty-second embodiment, regulating the diaphragm output of the patient for each breath cycle further includes comparing the determined diaphragm output to the preselected range of diagram output, and modifying the stimulation signal to be administered with the next ventilator breath if the diaphragm output from the last administered stimulation signal fell outside of the preselected range of diagram output.

In accordance with a forty-third embodiment, modifying the stimulation signal includes increasing the intensity of the stimulation signal.

In accordance with a forty-fourth embodiment, increasing the intensity includes one or more of: increasing the frequency of stimulation signal pulses; increasing the amplitude of stimulation signal pulses; and/or increasing the duration of stimulation signal pulses.

In accordance with a forty-fifth embodiment, diaphragm output includes tidal volume, pressure, or combinations thereof.

In accordance with a still another aspect of the present disclosure, a method is provided for preventing diaphragm disuse atrophy in a critically ill patient. The method comprises attaching a patient to a ventilator, monitoring the breath cycle of the ventilator; administering, within one of twelve hours or six hours of attaching the patient to the ventilator, a pre-programmed stimulation signal to the patient to recruit the diaphragm of the patient for outputting a level of diaphragm output, and regulating the level of diaphragm output of the patient for each breath cycle based on the administration of the stimulation signal to match or exceed a preselected threshold.

In accordance with yet still another aspect of the present disclosure, a method is provided for constructing a therapy plan for a patient. The therapy plan attempts to prevent disuse atrophy or rehabilitate the patient's diaphragm. The method comprises assessing the diaphragm for maximum diaphragm output and fatigue characteristics, and determining one or more stimulation signals that cause diaphragm output to be a preselected percentage of the maximum diaphragm output.

In accordance with a forty-sixth embodiment, the method further comprises creating a stimulation administration plan including a series of discrete stimulation signals, wherein the series of stimulation signals can vary by rate, duration, pulse width, frequency, and amplitude.

In accordance with still yet another aspect of the present disclosure, a method is provided for assessing a diaphragm. The method comprises monitoring data indicative of flow and pressure of a ventilator breath cycle, stimulating the diaphragm with stimulating signals based on the monitored data of the ventilator breath cycle, and determining one or more functional characteristics of the diaphragm from the response generated from the stimulation of the diaphragm with the stimulation signals. In some embodiments, the one or more functional characteristics including one or more of Maximum Static Inspiratory Pressure, Inspiratory Capacity, Work of Breathing, Pressure-Time Product, Pressure-Time Index, EMG, Maximum Relaxation Rate, and Expiration Time Constant.

In accordance with still another aspect of the present disclosure, a transvascular diaphragm pacing system is provided for constructing a therapy plan for a patient. The therapy plan in some embodiments prevents diaphragm disuse atrophy or rehabilitates the patient's diaphragm. The system includes at least one endovascular electrode configured to transmit a stimulation signal delivered thereto. The stimulation signal in some embodiments is configured to recruit a phrenic nerve of the patient and the stimulation signal has one or more stimulation parameters. The system also includes one or more sensors configured to sense breath cycle signals from an associated ventilator and diaphragm response from recruitment of the phrenic nerve, a pulse generator coupled in electrical communication with the at least one endovascular electrode, and at least one input device configured to input data indicative of one or more aspects of a therapy plan. The system further includes a controller coupled in electrical communication with the one or more sensors, the at least one input device, and the pulse generator. The controller is some embodiments is programmed to assess the diaphragm for maximum diaphragm output and fatigue characteristics, and determine one or more stimulation signals that cause diaphragm output to be a preselected percentage of the maximum diaphragm output.

In accordance with yet still another embodiment, a transvascular diaphragm pacing system is provided for assessing a diaphragm. The system includes at least one endovascular electrode configured to transmit a stimulation signal delivered thereto. The stimulation signal in some embodiments is configured to recruit a phrenic nerve of the patient and the stimulation signal has one or more stimulation parameters. The system also includes one or more sensors configured to sense breath cycle signals from the ventilator and the diaphragm response from recruitment of the phrenic nerve, a pulse generator coupled in electrical communication with the at least one endovascular electrode, and at least one input device configured to input data indicative of one or more aspects of a therapy plan. The system further includes a controller coupled in electrical communication with the one or more sensors, the at least one input device, and the pulse generator. The controller is some embodiments is programmed to: monitor data indicative of flow and pressure of a ventilator breath cycle; stimulate the diaphragm with stimulating signals based on the monitored data of the ventilator breath cycle; and determine one or more functional characteristics of the diaphragm from the response generated from the stimulation of the diaphragm with the stimulation signals. In some embodiments, the one or more functional characteristics include one or more of Maximum Static Inspiratory Pressure, Inspiratory Capacity, Work of Breathing, Pressure-Time Product, Pressure-Time Index, EMG, Maximum Relaxation Rate, and Expiration Time Constant.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 3A is one example of one pair of catheter-mounted phrenic nerve stimulating electrodes positioned within the left subclavian vein of the patient;

FIG. 3B is one example of one pair of catheter-mounted phrenic nerve stimulating electrodes positioned within the superior vena cava of the patient;

FIG. 13 illustrates yet other examples of timing as well as amplitude modulations for the stimulation trains generated and delivered to the phrenic nerves;

FIG. 33A-C graphically represent the benefits of examples of the system of FIG. 1 in preventing diaphragm disuse atrophy or rehabilitating the diaphragm for successful weaning from respiratory assistance.

DETAILED DESCRIPTION

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The following discussion provides examples of transvascular diaphragm pacing systems (TDPS) and methods for providing respiratory therapy to a patient. Some examples of the TDPS provide rapid insertion and deployment of endovascular pacing electrodes in critically ill patients who require intubation and invasive PPMV in order to support the physiological requirements of the human ventilatory system. Examples described herein make best use of the contractile properties of the diaphragm muscle and prevent muscle disuse and muscle atrophy. This can be carried out by engaging the phrenic nerves using patterned functional electrical stimulation applied to endovascular electrodes that are temporarily and reversibly inserted in central veins of the patient, such as the left subclavian vein and the superior vena cava. In some examples, the TDPS is designed to seamlessly interface with any commercially available positive-pressure ventilatory assistance/support equipment such as is commonly in use in hospital intensive care units (ICU) for treating critically ill patients with breathing insufficiencies, pain, trauma, sepsis or neurological diseases or deficits.

Rapid insertion and deployment of the disclosed systems can be effected via employment of minimally invasive central line catheter-based electrodes, such as those described in U.S. application Ser. No. 12/524,571, filed Jul. 25, 2009, which can be quickly installed in the patient under local anesthesia and rapidly activated, such that a pacing therapy can be initiated within one or a few hours of admission/intubation. If indicated by the patient clinical status, pacing via electrical stimulation can proceed in synchrony with ventilator breaths provided by virtually any brand or model of commercially available positive-pressure ventilator operating in typical modes such as Control Mode, Support Mode or Assist Mode. Once therapy is complete, the pacing catheter electrodes can be easily removed. In some embodiments, system pacing follows the operation of a ventilator while in other embodiments, the ventilator initiates and/or assists a breath cycle based on physiological responses generated by the pacing system.

Figure 33B:
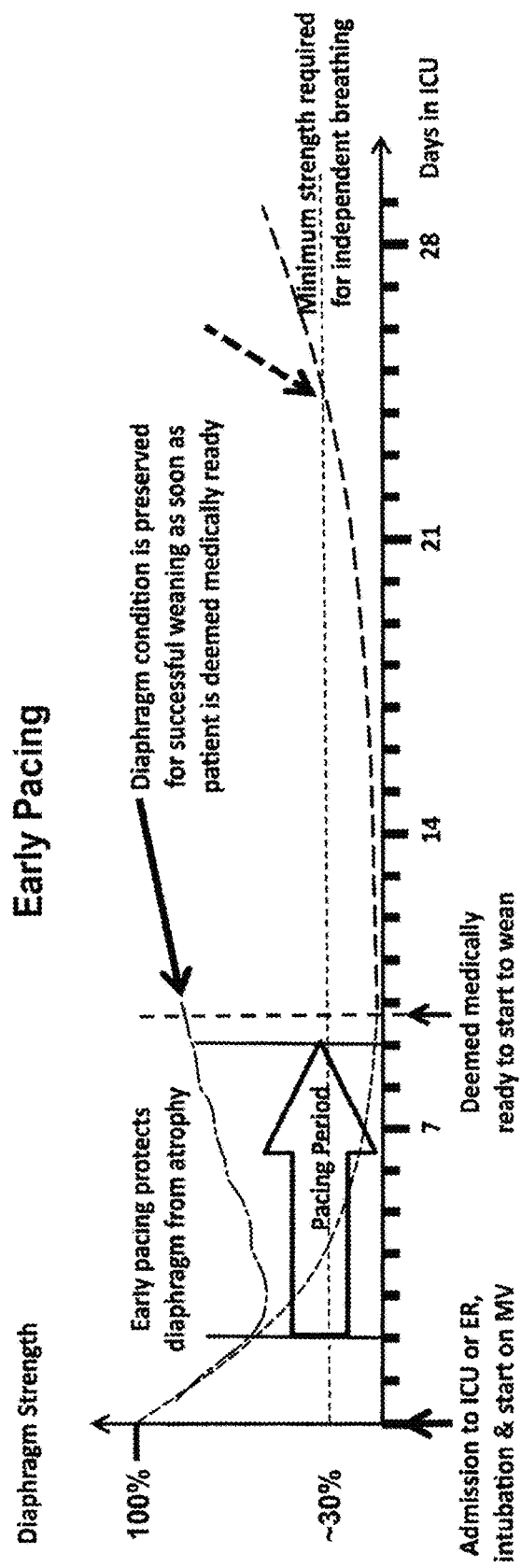
Figure 33C:
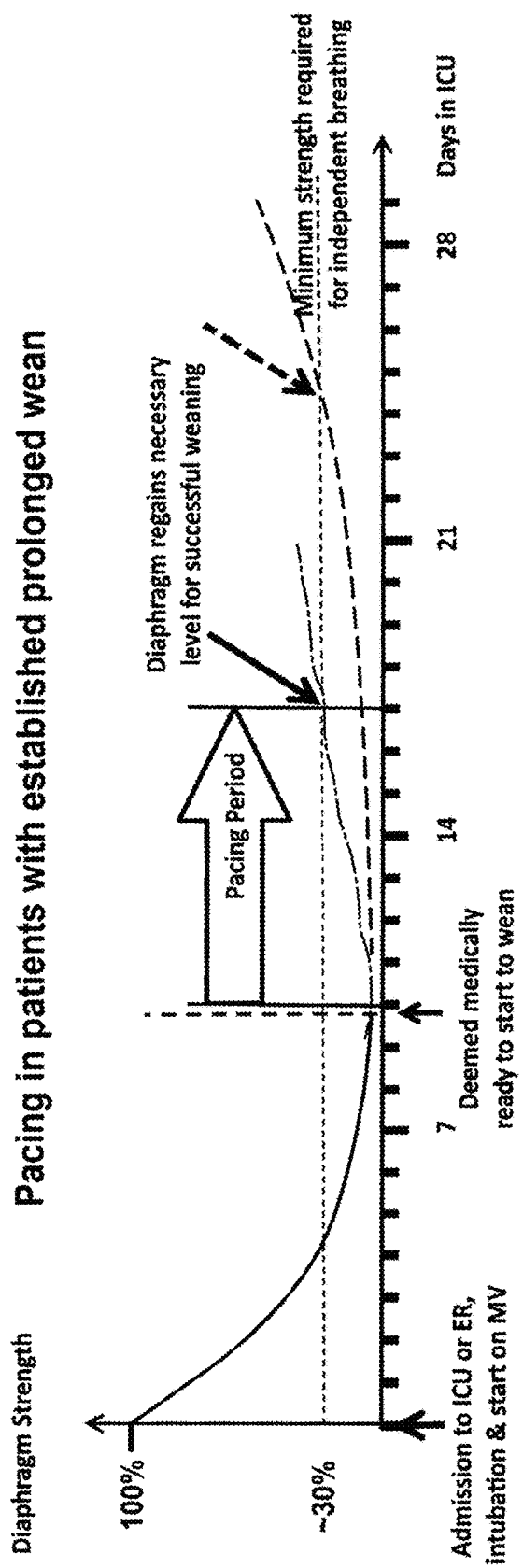

Rapid deployment, i.e., within a few hours of admission/intubation, is advantageous in preventing the ill effects of muscle disuse atrophy, which are known to occur very quickly in ventilated and sedated patients, and to maintain diaphragm muscle strength and endurance during the critical period when a patient is unable to breathe independently. FIG. 33A-C illustrate examples of employing the TDPS to prevent diaphragm disuse atrophy or rehabilitate the diaphragm for successful weaning from respiratory assistance. As a result, early and successful weaning from the ventilator can be realized. Another advantage stemming from the rapid deployment capability of the systems described herein and a rapid initiation of a diaphragm pacing therapy is that this intervention will help prevent/reduce the deleterious effects of high positive airway/lung pressures (such as Ventilator Induced Lung Injury, VILI) that are commonly encountered in patients subjected to mechanical ventilation and contribute to failure to wean and protracted dependence on ventilation in many cases. Patients who remain on mechanical ventilation have high risk of ventilator-associated pneumonia (VAP) and of contracting nosocomial (hospital-borne) infections. It is therefore important to ensure that a patient on mechanical ventilation is liberated (weaned) from ventilation as soon as medically possible. Examples of the pacing systems and methods described herein address this need and others.

As will be described in more detail below, the systems of the present disclosure are designed to stimulate the right phrenic nerve (to recruit the right hemi-diaphragm), the left phrenic nerve (to recruit the left hemi-diaphragm), or both phrenic nerves in order to recruit the entire diaphragm muscle. Furthermore, each phrenic nerve may be recruited using a single channel of stimulation or two or more channels of stimulation per nerve. An example showing one embodiment employing two channels of stimulation per phrenic nerve is shown in FIG. 3. In some examples that employ two channels of stimulation per nerve, the stimulation pulses can be delivered 180 degrees out of phase.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
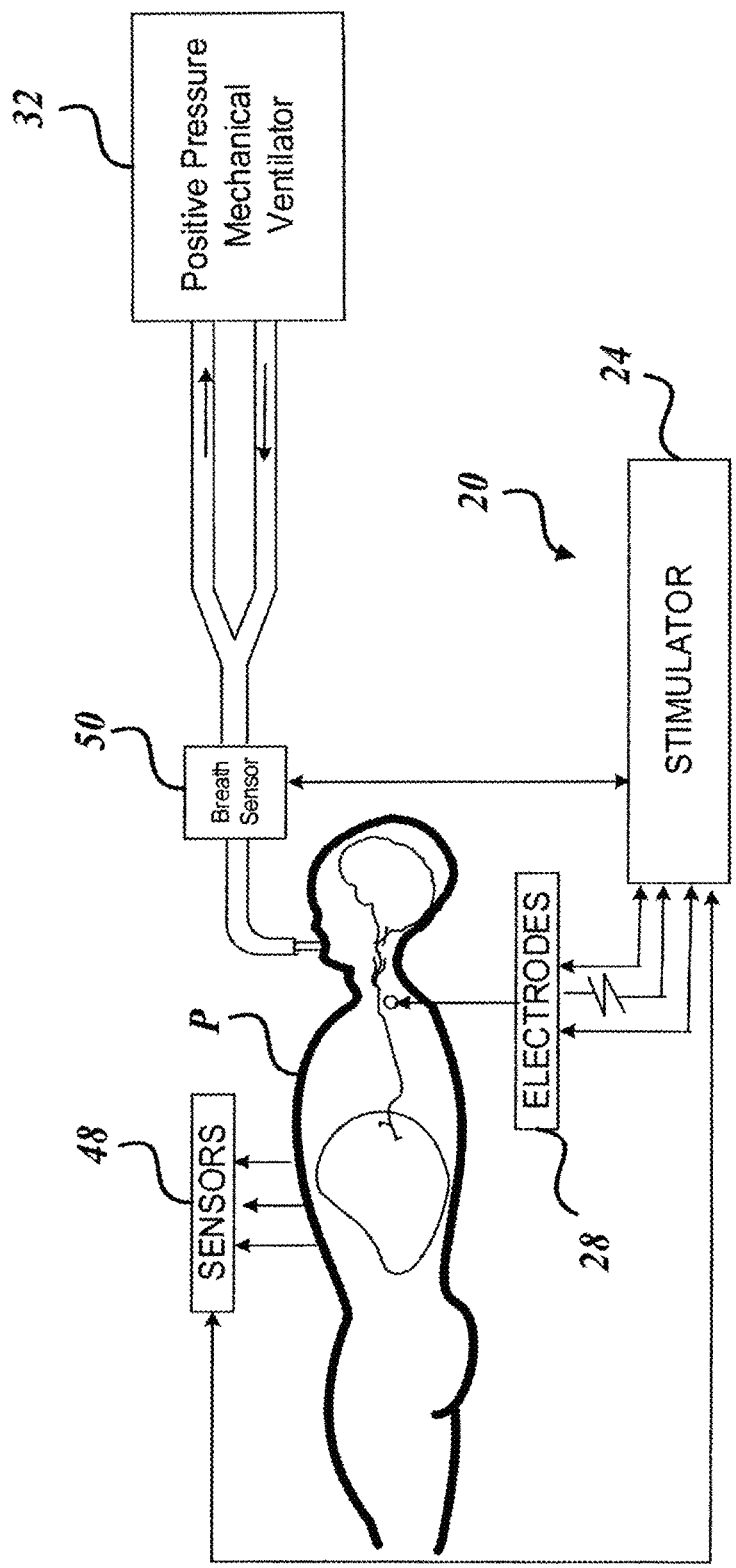
FIG. 1 is a schematic diagram of one example of a transvascular diaphragm pacing system formed in accordance with aspects of the present disclosure.
Figure 4:
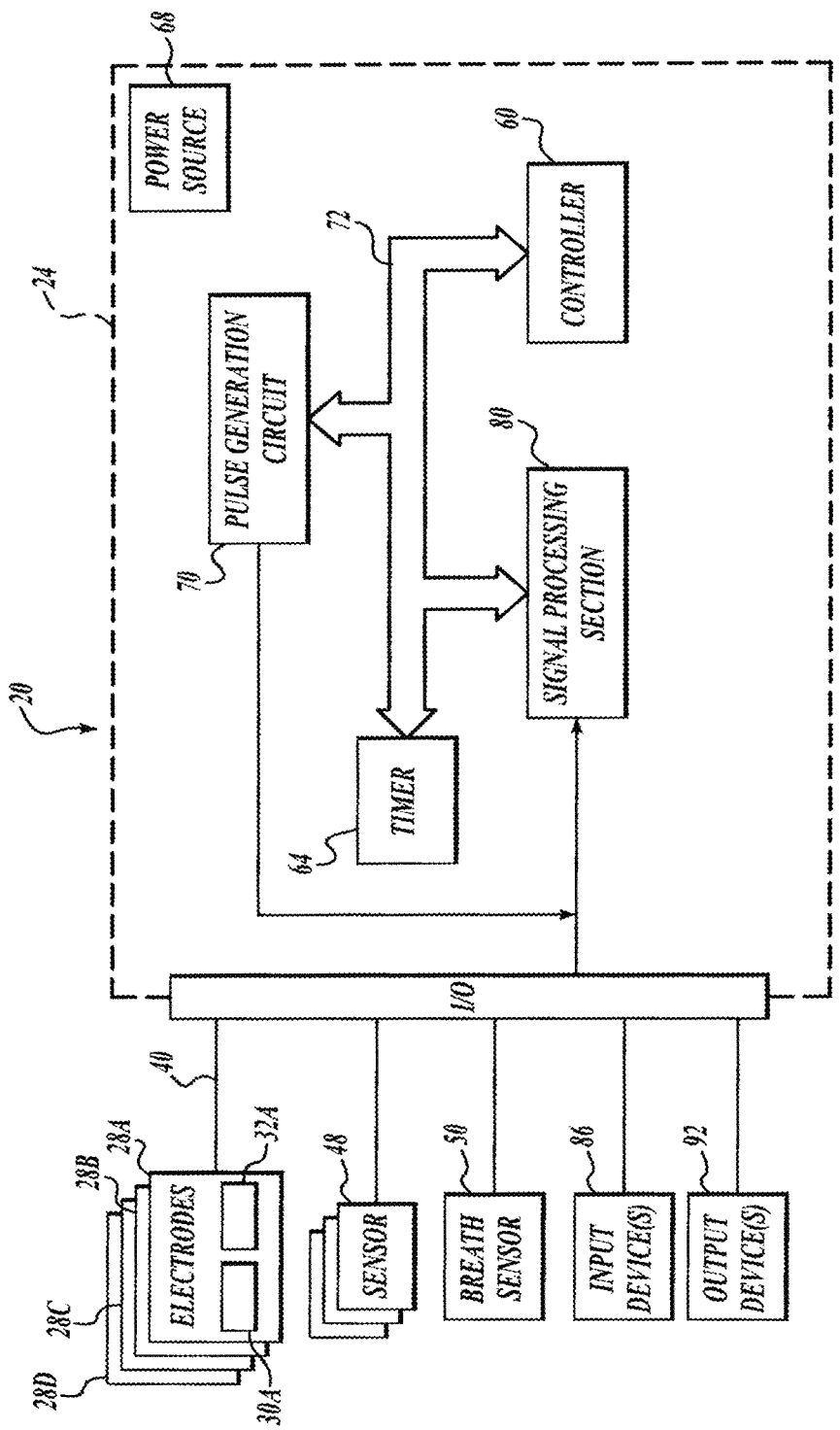
FIG. 4 is a block diagram of the components of one embodiment of the system of FIG. 1.

Turning now to FIG. 1, one example is shown of a transvascular diaphragm pacing system, generally designated 20, formed in accordance with aspects of the present disclosure. As best shown in FIGS. 1 and 4, the system 20 includes a stimulator 24 coupled in electrical communication (e.g., wired or wireless) with one or more transvascular electrodes 28 suitable for placement in-vivo near the left and/or right phrenic nerves. In use, the stimulator 24 is configured to transmit a stimulatory signal in the form of stimulation pulses to one or more of the electrodes 28. The electrodes 28, in turn, emit the stimulatory signal in the vicinity of a left and/or right phrenic nerve. Stimulation of the left and/or right phrenic nerve, in turn, aims to cause recruitment of the subject's diaphragm.

As will be described in more detail below, the parameters (amplitude, duration, frequency, etc.) of stimulation pulses affect the amount of diaphragm recruitment, and the resulting output (such as tidal volume, pressure) therefrom. In that regard, and as will be described in more detail below, sensors 48 configured to sense various physiological parameters of the patient, some indicating diaphragm output, can provide feedback to the stimulator 24 for regulation of the administered therapy.

As described herein, the system 20 can be the sole respiratory aid for the patient. In other embodiments, the system 20 operates in conjunction with a positive pressure mechanical ventilator 32 ("ventilator 32") in order to satisfy the respiratory needs of the patient. In some embodiments, signals sensed from a breath sensor 50 that monitors the breath cycle of the ventilator 32 can be employed to synchronize the delivery of the stimulation signals with the ventilator breath cycle.

The respiratory needs of the patient are sometimes referred to as the patient's prescribed assist level. The prescribed assist level is generally quantified as the amount of tidal volume or pressure (or a combination of the two) provided to the patient during one breath cycle that satisfies the minimum physiological functions of the patient. Generally, the prescribed assist level in terms of tidal volume is approximately 7-10 mL per Kg of patient weight. In some embodiments, the prescribed assist level is satisfied solely via artificial means (e.g., via system 20, via ventilator 32, or a combination of the two). This may occur in patients that are heavily sedated and/or unconscious. In other embodiments, the prescribed assist level may include some patient initiated respiratory effort.

As will be described below, in some embodiments, the clinician, as part of a therapy plan, can program the system 20 in order to satisfy the prescribed assist level (i.e., in tidal volume, pressure, or both) via recruitment of the diaphragm. In other embodiments, the clinician can program the system 20 to contribute only a percentage of the prescribed assist level (in volume, pressure, or both), referred to herein as the diaphragm contribution or diaphragm contribution level, via electrical recruitment of the phrenic nerve or nerves. The percentage can vary, and is patient-dependent based on a variety of factors, such as the condition of the patient, the ailment afflicting the patient, time elapsed preceding any stimulation therapy, etc. In this embodiment, the remaining percentage of the prescribed assist level can then be satisfied by the ventilator 32, which can be appropriately programmed by the clinician at the onset of or during administration of the therapy plan.

In some embodiments, as will be described in more detail below, the system 20 carries out one or more assessments of the patient in order to determine, for example, the current condition of the patient's diaphragm, the stimulation signal characteristics that relate to the recruitment of the diaphragm, such as threshold pulse width, pulse amplitude, pulse frequency, sub-maximal pulse width, and supra-maximal pulse width, etc. Threshold Pulse Width refers to a minimum pulse width at and above which there is a diaphragmatic response. Threshold Frequency refers to a minimum frequency at and above which partly or completely fused Tetanic contractions are produced, so as to generate useful diaphragmatic force and/or work.

Figure 2:
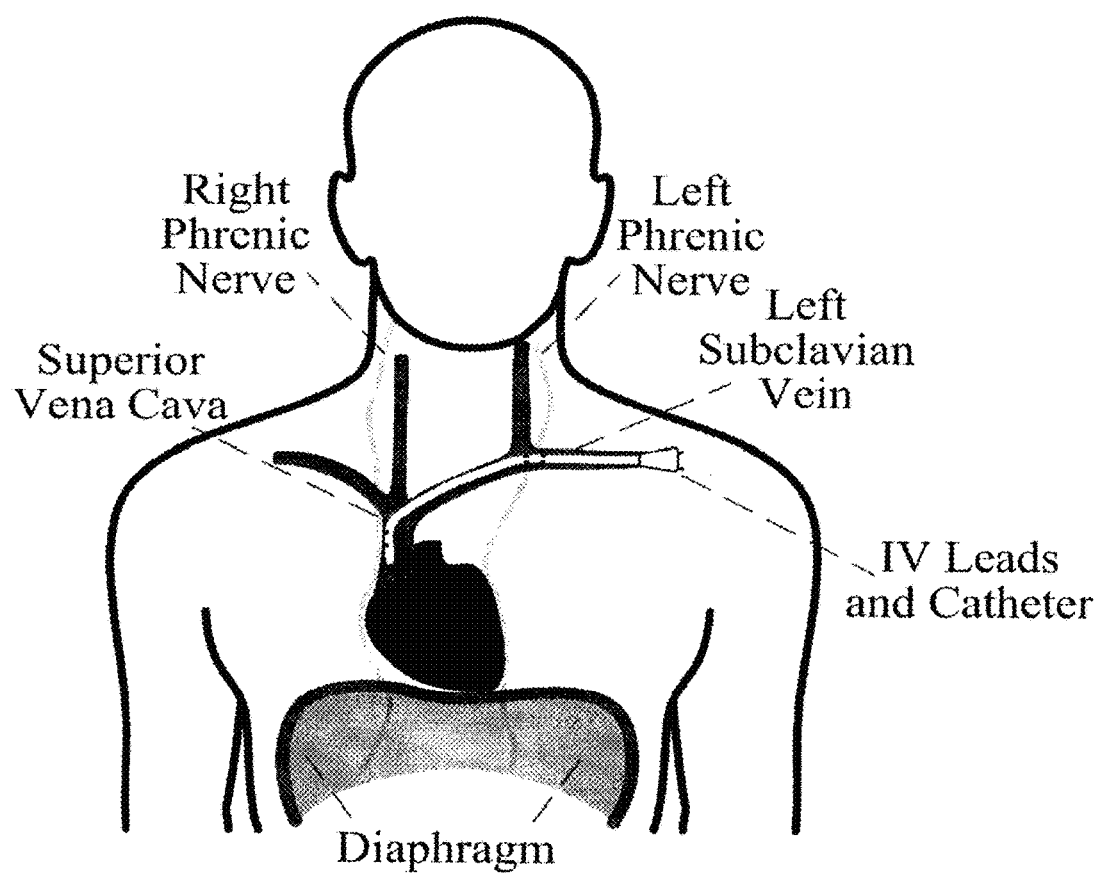
FIG. 2 is a schematic diagram of the location of the left and right phrenic nerves in a patient in relation to the heart and diaphragm of the patient.
Figure 2A:
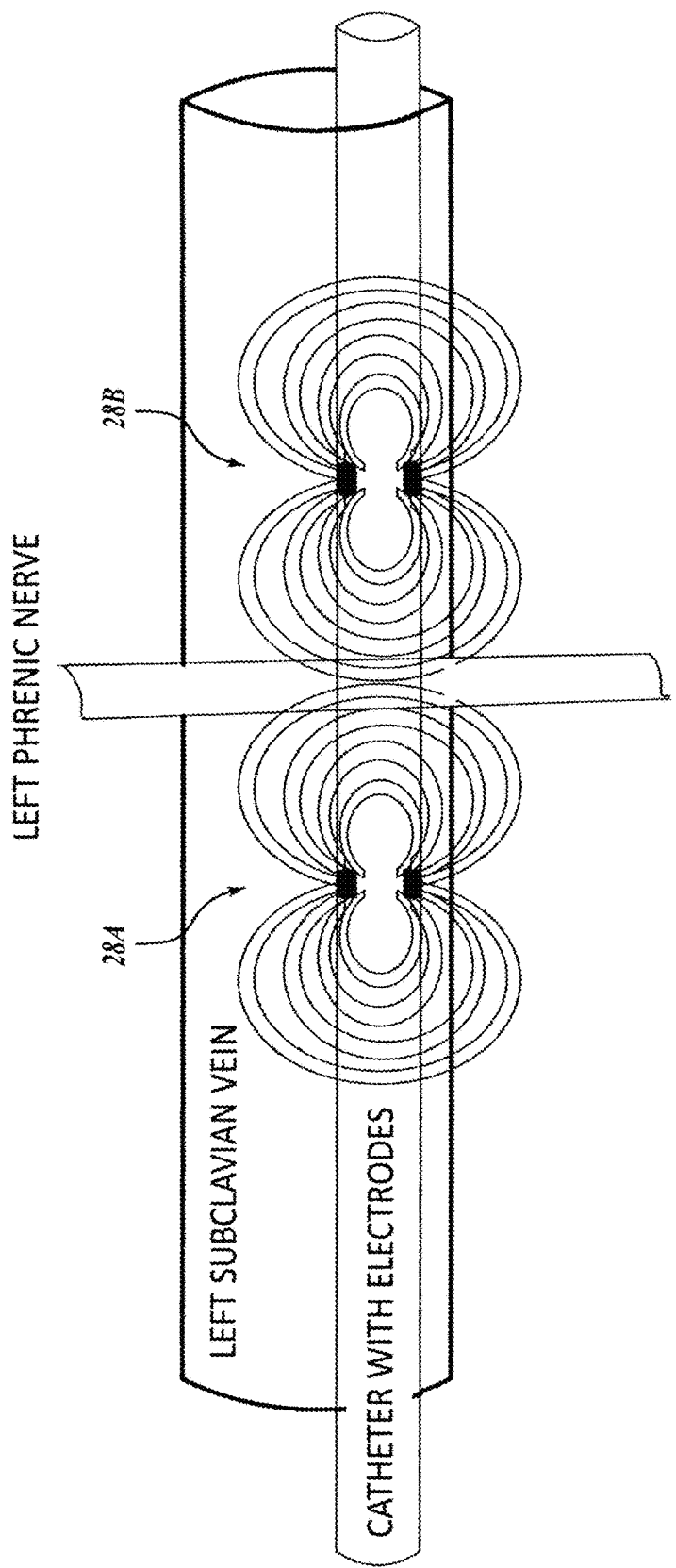

Turning now to FIG. 2, placement of the electrodes 28 will now be described with reference to a heart H and diaphragm D of a patient P. As shown in FIG. 2, the left and right phrenic nerves run along the lateral and medial side of the heart to a diaphragm D. The left subclavian vein traverses in proximity to the left phrenic nerve and transmits blood from the upper extremities to the heart H. The superior vena cava traverses near the right phrenic nerve and carries deoxygenated blood from the upper half of the body to the heart's right atrium. As known in the art, when either left or right phrenic nerve receives a high enough electric stimulus as a voltage (V), current (mA) or charge (nano-coulombs) the phrenic nerve is activated and causes the diaphragm D to contract.

FIG. 3 illustrates one embodiment showing two channels of transvascular stimulation delivered to the left phrenic nerve by endovascular electrodes placed in the left subclavian vein and two channels of transvascular stimulation delivered to the right phrenic nerve by endovascular electrodes placed along the lateral wall of the superior vena cava. Each phrenic nerve can be partially or fully recruited from more than one endovascular electrode combination. Partial nerve recruitment from more than one electrode combination is useful to reduce muscle fatigue over time.

Turning now to FIG. 4, the components of the system will now be described in detail. As shown in FIG. 4, the system 20 includes a first electrode 28A having anodal and cathodal electrode contacts 30A, 32A placed within the left subclavian vein and positioned in the vicinity of the left phrenic nerve. In the embodiment shown, a second electrode 28B having anodal and cathodal electrode contacts 30B, 32B may be also placed within the left subclavian vein and positioned in the vicinity of the left phrenic nerve.

The system 20 further includes a third electrode 28C having anodal and cathodal electrode contacts 30C, 32C placed within the superior vena cava and positioned in the vicinity of the right phrenic nerve. In the embodiment shown, a fourth electrode 28D having anodal and cathodal electrode contacts 30D, 32D may be also placed within the superior vena cava and positioned in the vicinity of the right phrenic nerve.

While two electrodes are shown and described for stimulating each of the left and right phrenic nerves, it will be appreciated that other numbers of electrodes may be practiced with embodiments of the present disclosure. For example, four electrodes can be used for stimulating each phrenic nerve. For more information regarding the placement of a plurality of electrodes endovascularly as well as the configuration of one type of electrode structure that can be practiced with embodiments of the present disclosure, please see U.S. application Ser. No. 12/524,571, filed Jul. 25, 2009, the disclosure of which is hereby expressly incorporated in its entirety. Additionally, while electrodes with anodal and cathodal electrode contacts are utilized to emit the stimulation pulses into the phrenic nerves, other configurations are possible. For example, several cathodal electrode contacts may be used in conjunction with a single anodal electrode contact, and vice versa.

Each electrode 28 is connected in electrical communication with the stimulator 24. In the embodiment shown, each electrode 28 is electrically connected to the stimulator 24 via lead(s) 40.

The system 20 further includes one or more sensors 48 configured to monitor the response to phrenic nerve stimulation and/or other physiological characteristics of the patient. As will be described in more detail below, the one or more sensors 48 can be part of a feedback control scheme for regulating the stimulation administered to the patient. The plurality of sensors 48 can transmit data to the stimulator 24 indicative of one or more of the following: electromyographic activity (intramuscular, surface, and/or intraesophageally monitored), central venous pressure (any specific component of this signal), heart rate, chest wall acceleration, blood oxygen saturation, carbon dioxide concentration, catheter position/depth within vein, mechanical movement (i.e., from accelerometers, length gauges, and/or strain gauges) resistance (i.e., from impedance pneumographs, and/or piezoresistive sensors) and/or other physiological or mechanical parameters. It will be appreciated that the information can be appropriately processed (e.g., filtered, conditioned, amplified, etc.) prior to use by the stimulator 24.

The term "volume" as used herein includes, but is not limited to, Inspired Tidal Volume, Expired Tidal Volume or Minute Volume. The term "pressure" as used herein includes, but is not limited to, Airway Pressure, Alveolar Pressure, Ventilator Pressure, Esophageal Pressure, Gastric Pressure, Transdiaphragmatic Pressure, Intra-Thoracic Pressure Positive End-Expiratory Pressure or Pleural Pressure. Any pressure may be Peak Pressure, Mean Pressure or Baseline Pressure. The term "flow" as used herein includes, but is not limited to, Inspiratory Flow or Expiratory Flow.

In some embodiments, the electrodes 28 can also monitor physiological variables of the subject by virtue of their placement in the central veins. Such monitored physiological variables can include, but are not limited to: central venous pressure, electrocardiogram, and mixed venous oxygen saturation. It will be appreciated that one or more sensors discrete from the electrodes, such as one or more of the sensors 48, may be used to monitor such physiological variables.

In some embodiments, the system 20 can additionally or alternatively include a breath sensor 50 for sensing parameters of the ventilator 32. In that regard, the breath sensor 50 can be configured to interface with any standard breathing circuit used in critical care ventilators and therefore the pacing system is independent of the brand of ventilator used. The breath sensor 50, by virtue of its location in the breathing circuit, can monitor and/or measure several ventilation parameters and communicate such parameters to the stimulator 24. As will be described in more detail below, the breath sensor 50 can be part of or used solely as a feedback control scheme for regulating the stimulation administered to the patient. The sensed ventilation parameters may include, but not limited to, airflow (inspired and/or expired), volume, pressure (airway, esophageal, gastric, and/or some combination/derivative of the former). In some embodiments, other sensors may aid in the procurement of one or more ventilation parameters.

In some embodiments, the example parameters are being measured both to and from the ventilator 32. In the embodiment shown, the breath sensor 50 is external to the ventilator 32 so that the system is independent of ventilator model. However, the system 20 could also be integrated to use a ventilator's internal sensors or signals externally supplied by the ventilator can provide the information to the system 20 for proper operation so that an external breath sensor can be omitted.

The stimulator 24 functions, in part, as a signal generator for providing therapy to the diaphragm in response to information received from the one or more of the sensors 48 and 50 and/or information programmed into the system 20 by the clinician. In that regard, the stimulator 24 delivers pulses to the endovascular electrodes 28 in accordance with one or more protocols described herein. As will be described in more detail below, the pulses in some embodiments are generated by the stimulator 24 with characteristics that deliver a suitable charge to the phrenic nerves in order to provide enough diaphragm recruitment to satisfy the selected diaphragm contribution (e.g., in volume, pressure, both, or derived parameters from volume and pressure) of the prescribed assist level described above.

Towards that end, the stimulator 24 is configured to deliver fully programmable stimulation, including, but not limited to, the following: any number of pulses, any combination of the defined pulses, any order of delivery of the defined pulses, multiple instances of any defined pulse(s), any frequency of stimulation, and/or any delay between pulses (interpulse delay). Each pulse can be independently programmable (e.g., frequency, amplitude, duration, etc.). The stimulation pulse(s) and/or train(s) may or may not generate a repeatable pattern.

Figure 6:
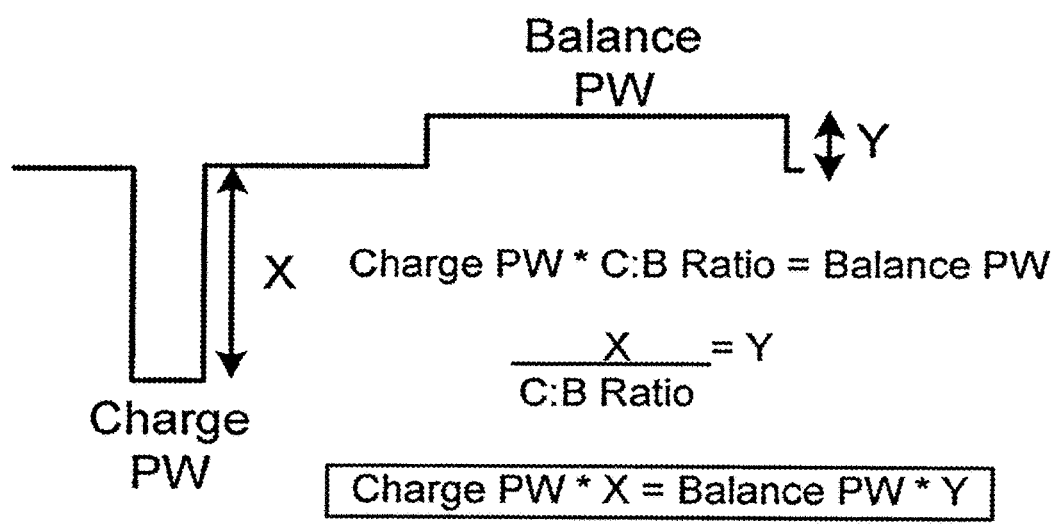
FIG. 6 illustrates one example of the programmable parameters of each stimulation pulse as well as the ratiometric relationship between the charge injection pulse and charge balance pulse when exemplifying net-charge.

Each pulse includes a charge injection phase and a charge balance phase (biphasic). In some embodiments, the balance phase duration and amplitude is programmable as a ratio of the charge phase duration and amplitude so that zero net charge is maintained, as shown in FIG. 6. This ratio, denominated as the Charge:Balance Ratio (C:B Ratio), is applied so that the product of amplitude and duration (charge) is equal in both the charge phase and the balance phase. In some embodiments, each pulse is programmable via the following parameters: ratio of charge phase duration to balance phase duration; pulse width range; stimulation amplitude (current level); and delay between the charge phase and the balance phase. Stimulation amplitude may be changed during the same phase (i.e., generate a gradually decreasing current for the charge pulse width). While zero net change is preferred, non-netzero charges may be used.

Figure 5:
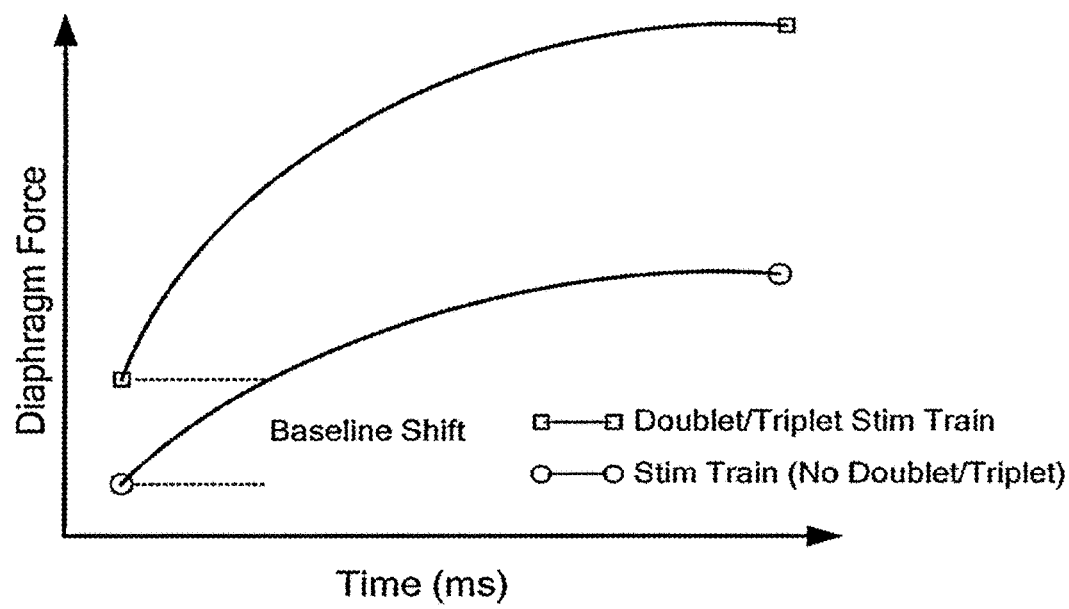
FIG. 5 illustrates the shift in force generated when stimulating with a train that begins with a doublet/triplet.
Figure 7:
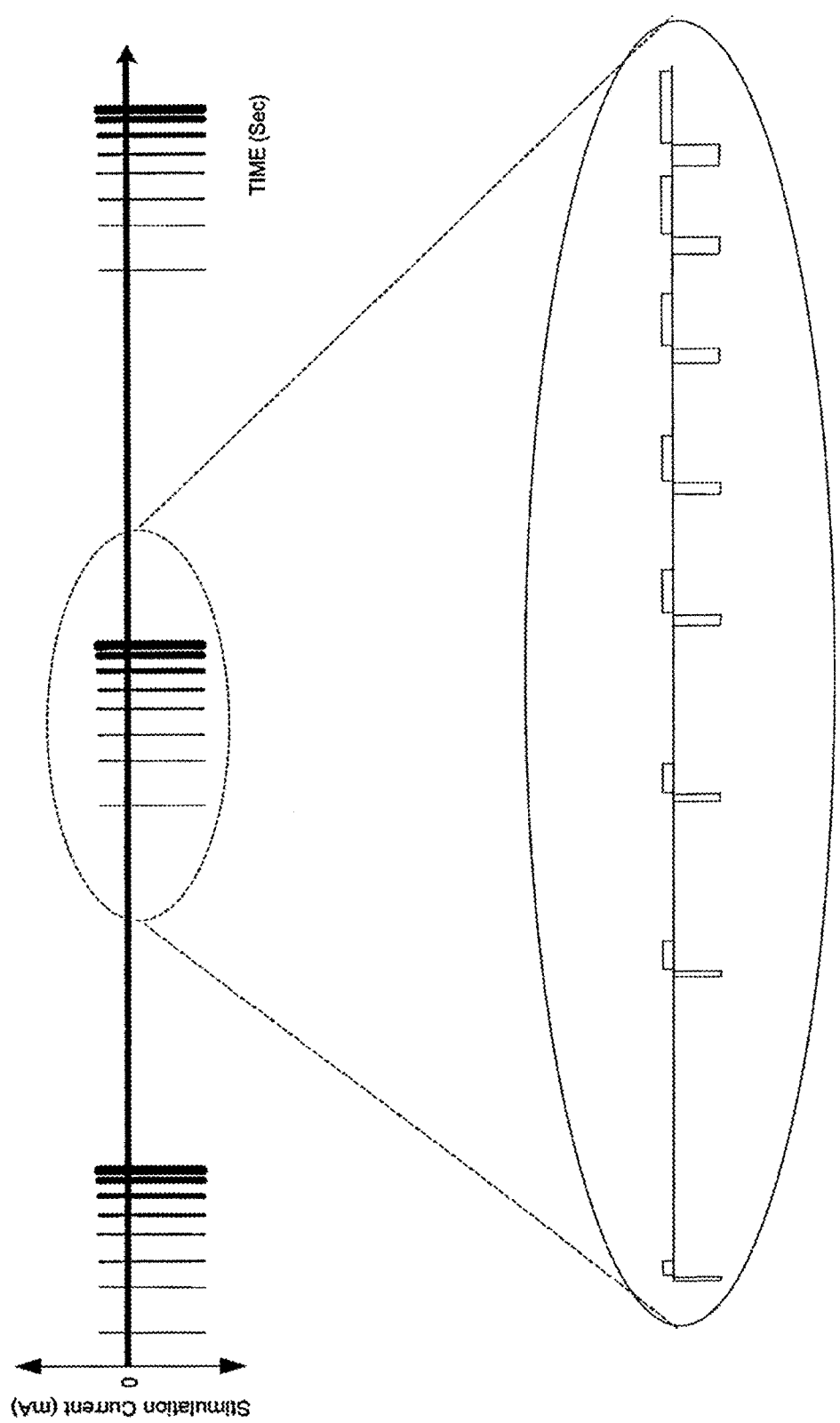
FIG. 7 illustrates one example of three stimulation trains, in each of which the pulse width and frequency are modulated to increase from the start to end of the stimulation train to cause graded contraction of the diaphragm.
Figure 8:
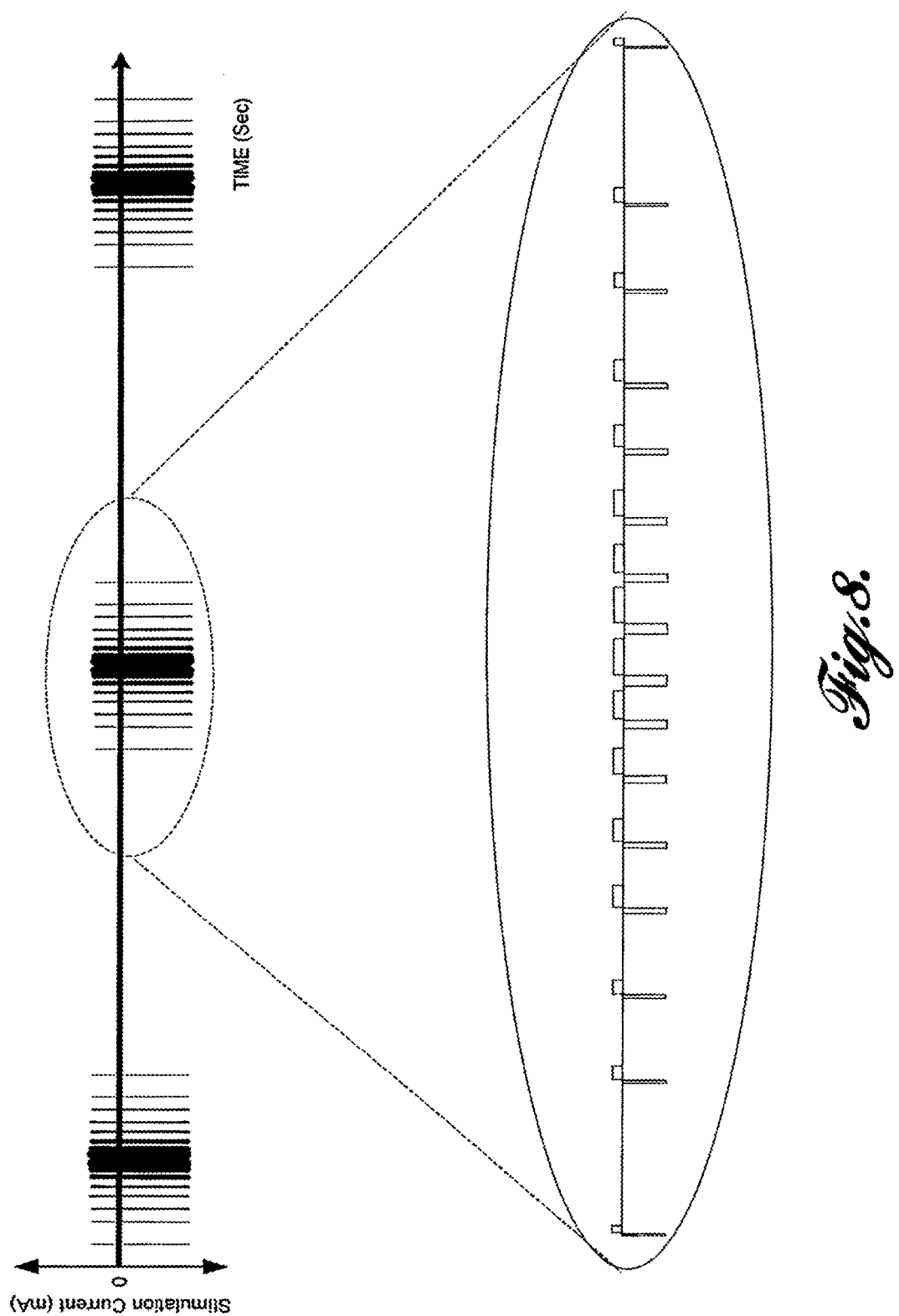
FIG. 8 illustrates one example of three stimulation trains, in each of which the pulse width and frequency are modulated to first increase and then decrease from the start to end of the stimulation train to cause graded contraction of the diaphragm.

Because the diaphragm is skeletal muscle, pacing may be accomplished by delivering one or more stimulation signals to produce a mechanically effective contraction of the diaphragm. In that regard, the stimulation signals may include a plurality of pulses that are grouped in stimulation trains. As used herein, a stimulation train is defined as a collection of stimulation pulses. This definition does not imply a specific composition, order of delivery, and/or shape profile or envelope. FIGS. 7 and 8 illustrate examples of stimulation trains generated by the stimulator 24 and delivered to the electrodes 28 for stimulating the phrenic nerves. The stimulation trains may start with a doublet (pair of pulses) or a triplet, which can be physiologically relevant; two or three pulses in quick succession at the beginning of recruitment has been shown to increase the overall force profile by shifting the baseline up during the initial onset of recruitment, as demonstrated in FIG. 5. Similarly, a doublet or triplet delivered part-way through a train can cause a sustained force increase. The upward shift in early force production infers that fewer stimulation pulses can be used to generate the same amount of force from the diaphragm in a comparable period of time. This can be quite beneficial since over-activating the diaphragm with excessive numbers of stimulation pulses may induce fatigue, and may also cause conversion of fibers from fast-twitch (powerful, but fatigued easily) to slow-twitch (fatigue-resistant but unable to produce large amounts of force).

Stimulation or pulse trains are typically characterized by the rate, the duration, the pulse width, the frequency, and the amplitude of the signals. The rate of the stimulation train corresponds to the number of stimulation trains delivered per minute, which can correlate with the patient's respiratory rate or mechanical ventilator rate. The duration of the stimulation train refers to the length of time the stimulation train is delivered. The pulse width indicates the duration of each individual pulse creating the stimulation train. Similarly, the frequency indicates the number of individual pulses delivered per second. Finally, the amplitude refers to the voltage of each pulse delivered. The parameters of amplitude, frequency, and pulse width determine the strength of the induced diaphragmatic pacing.

In some embodiments, the stimulation trains form ramp trains. For example, ramp trains can be formed by linearly increasing (or decreasing) either the instantaneous frequency of consecutive pulses in a train, the durations (pulse widths) of consecutive pulses in a train, or both. Ramp trains indicate that a change in injected charge is induced by the programmed stimulation parameters and any applied modulation.

Figure 9:
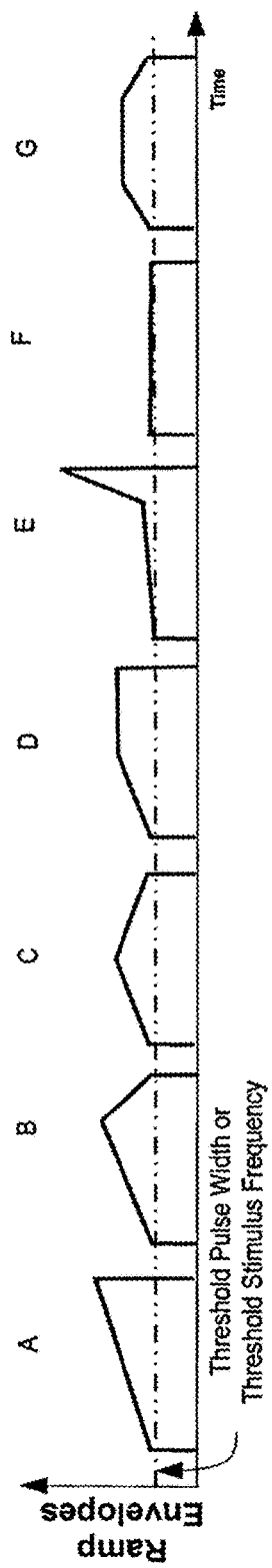
FIG. 9 illustrates examples of representative ramp envelopes where the ramp slopes represent the modulations in pulse width and/or pulse frequency within a train.
Figure 10:
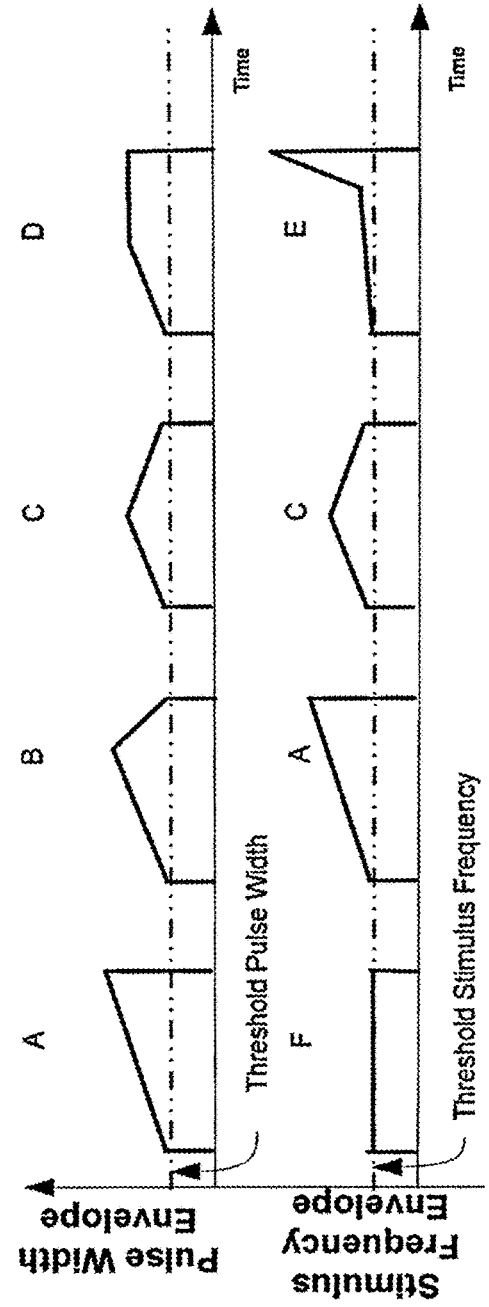
FIG. 10 illustrates examples of representative pulse width ramp envelopes and stimulus frequency envelopes, which can be combined together to form a single pacing ramp.

Variations in pulse width and frequency modulation allow different ramp train envelopes to be designed. Referring to FIG. 9, ramp envelopes can be generated during a single pacing ramp in pulse width alone, frequency alone or both in pulse width and frequency. Pulse width and stimulus frequency envelopes can be modulated together or combined, as shown in the examples of FIG. 10, during pacing to generate a desired ramp train. For example, combination AF will cause a graded recruitment of the phrenic motoneurons at a constant frequency (no rate coding) and Combination BA will gradually recruit and de-recruit the motoneurons, with a steadily increasing rate coding; although any combination is possible. It will also be possible to alter the rate of recruitment and de-recruitment (slope) of motoneurons, independent of the rate coding, by adjusting the relative percentage of pulse width increase and decrease duration within a single pacing ramp. Further, the pulse width and frequency modulation can be defined mathematically as piecewise functions in time, thereby allowing any desired ramp envelope to be generated while remaining within the scope of the present disclosure.

Although a large set of ramp trains can be generated, there will be some embodiments where the ramp trains aim to achieve one or more of the following: 1) mimic physiological contraction of the diaphragm by independently controlling recruitment and rate coding by means of pulse width and frequency modulation, respectively; 2) delay the onset of neuromuscular fatigue; 3) maintain the native fiber composition of the healthy diaphragm; 4) condition the diaphragm towards a specific fiber type, for e.g. Type I (Slow Twitch, Fatigue Resistant).

With the various programmable stimulation trains or ramp trains, a therapy plan can be constructed by the clinician with or with the aid of the system 20. The therapy plan constructed by the clinician is patient dependent in order to achieve various goals. The therapy plan may include one or more of the following: timing of delivery of pacing in relation to ventilator breaths (e.g., every breath, every other breath, every five breaths, etc.); intermittent stimulation segments (e.g., stimulation delivery for 15 minutes every hour), etc. As an example, in a patient who requires PPMV and sedation, a therapy plan would take into consideration both major objectives of minimizing VIDD and minimizing risk of VILI. As another example, in a therapy plan for a patient who able to remain awake during part of the day and breathe independently for some hours and will soon be attempting to wean, it may be desirable to not pace while the patient is breathing spontaneously but, conversely, to pace at a low assistive level during the night while the patient is again sedated and placed back on PPMV, in order to reduce the peak pressure required for ventilation and thus reduce risk of VILI.

In some embodiments, the therapy plan includes the ability to skip stimulation, sometimes referred to as skipped breaths, which allows for a ventilator breath to be delivered without being accompanied by stimulation from the system 20. Additionally or alternatively, the therapy plan may include sigh breaths. Sigh breaths are characterized as intermittently programmable breaths that inject more charge than a normal breath (i.e. a higher magnitude stimulation train). Physiologically, this results in a more forceful contraction of the diaphragm. Both functions are programmable independently and can be repeatable. For sigh breaths only, the percentage increase in amplitude is programmable based on the amplitude of a typical paced breath. It is possible to implement these features independently or combined.

FIG. 13A-C illustrate an example of skipped breaths, sigh breaths, and a combination of skipped breaths and sigh breaths, respectively. FIG. 13A is an example of skipped breaths, where the system 20 skips every 3rd breath. This means that during the skipped breath, the patient receives the ventilatory support entirely from the ventilator 32. During the skipped breaths, respiratory mechanics such as tidal volume, compliance of the lungs, resistance to airflow or the recruitment of the lung regions may vary. FIG. 13B is an example of sigh breaths generated by the system 20 while operating in synchrony with the ventilator 32. In this example, a sigh breath is delivered every $3^{rd}$ breath. Depending upon whether flow is controlled or pressure controlled, the sigh breaths can alter the respiratory mechanics. This feature mimics a feature of spontaneous breathing namely, variable tidal volume. FIG. 13C is an example of both skipped and sigh breaths being administered in a periodic manner by the system 20.

The stimulator 24 in some embodiments is configured to generate constant-amplitude current pulses with pulse duration in the range from 50-300 microsec, controllable in increments of 10 microsec. The amplitude and duration of each pulse in a train can be independently programmed. The amplitude of pulses can be selected between 0.1 and 10 mA in 0.1 mA increments. The main parameter that determines whether a stimulus pulse will be sufficient to activate a nerve axon (reach its threshold to fire an action potential) is the charge delivered by the stimulus, where charge (in nC)=pulse current amplitude (in mA)×pulse duration (in microsec). In this regard, the stimulator 24 can produce pulses in the range from 5 nC to 3000 nC and the charge per pulse can be specified in increments of 1 nC.

FIG. 4 shows a schematic diagram of one embodiment of the stimulator 24. As shown in FIG. 4, the stimulator 24 includes a controller 60, which receives signals sensed from one or more sensors 48 and/or the breath sensor 50. The stimulator 24 may also include a timer 64 coupled to controller 60, and a power source 68. The controller 60 is coupled to a pulse generation circuit 70, which delivers stimulation signals to one or more of the electrodes 28 via leads 40. In one embodiment, the components described above are coupled via bus 72. In some embodiments, the power source 68 of the stimulator 24 includes one or more batteries. In other embodiments, the power source 68 includes a power regulation section that receives power from standard "mains," and transforms it into appropriate power for the circuitry of the stimulator 24.

Those skilled in the art and others will recognize that the controller 60 serves as the computational center of the stimulator 24 for carrying out logic or by supporting the execution of routines, instructions, etc., for providing functionality to the stimulator 24. In that regard, the logic, routines, instructions, etc., described herein may be implemented in hardware, in software, or a combination of hardware and software.

In some embodiments, the controller 60 includes one or more processors and memory. The logic, routines, instructions, etc., may include a set of control algorithms, including resident program instructions and calibrations stored, for example, in the memory and executed to provide a desired functionality of the system 20. The algorithms may be executed during preset loop cycles such that each algorithm is executed at least once each loop cycle. Algorithms stored in non-volatile storage medium can be executed by the processor to: 1) monitor inputs from the sensors 48, 50 and other data transmitting devices or polls such devices for data to be used therein; 2) cause the pulse generator to generate and transmit one or more pulses to the electrodes 28; and 3) regulate the diaphragm output of the patient, among other functions. Loop cycles are executed at regular intervals, for example each 3.125, 6.25, 12.5, 25 and 100 milliseconds during ongoing operation of the system 20. Alternatively, algorithms may be executed in response to the occurrence of an event.

As used herein, the term processor is not limited to integrated circuits referred to in the art as a computer, but broadly refers to a microcontroller, a microcomputer, a microprocessor, a programmable logic controller, an application specific integrated circuit, other programmable circuits, such as programmable gate arrays, combinations of the above, among others. In some embodiments, the controller 60 may include additional components including but not limited to a high speed clock, analog to digital (A/D) and digital to analog (D/A) circuitry, input/output circuitry and devices (I/O) and appropriate signal conditioning and buffer circuitry.

It will be appreciated that the signals received from the sensors 48, 50 may be processed by an optional signal processing section 80 prior to arriving at the controller 60. For example, the signal processing section 80 may include dedicated circuits, processors, such as digital signal processors (DSP), etc., for receiving, processing and filtering electrical signals sensed by the sensors associated with the subject and/or the ventilator 32. Signal processing section 80 can include amplifiers and circuits to condition, filter and/or amplify the electrical signals supplied thereto. In some embodiments, the signal processing section 80 carries out discrete tasks, such as the determination of one or more physiological states. One physiological state that can be determined by signal processing section 80 is a patient's minute volume or ventilation. Minute ventilation is a respiratory related parameter that is a measure of the volume of air inhaled and exhaled during a particular period of time. The minute ventilation is the product of respiration rate and tidal volume. Signal processing section 80 can also be used to receive and process signals representing other respiratory activity such as intrathoracic pressure, chest wall motion, etc. Of course, the determination of one or more physiological states, processing of signals, implementation of logic or processes, etc., can be carried out solely by the controller 60.

Still referring to FIG. 4, the stimulator 24 includes one or more input devices 86. The input devices 86 may include switches, knobs, etc., supported by the housing of the stimulator, and/or computer style devices, such as a keyboard, a touchpad, etc. The input devices 86 provide for the input of data, such as the pacing parameters, ventilator parameters, etc., into the stimulator 24. Output devices 92, such as a monitor, may also be provided.

In accordance with aspects of the present disclosure, one or more embodiments of the system 20 can be operated in various pacing modes. The pacing modes may be alternatively employed by a clinician, depending on the clinical status and needs of each patient and on the operational properties of a ventilator, such as ventilator 32, which may be available in a particular ICU. The pacing modes can include but are not limited to Ventilator-Initiated Pacing Mode, Pacer-Initiated Ventilation Mode, and Autonomous Pacing Mode. Those skilled in the art will understand that these modes may be engaged in many ways to generate different combinations of system functionality, but for reasons of brevity all possible combinations are not listed herein. Each of these modes will now be described in some detail.

Figure 11:
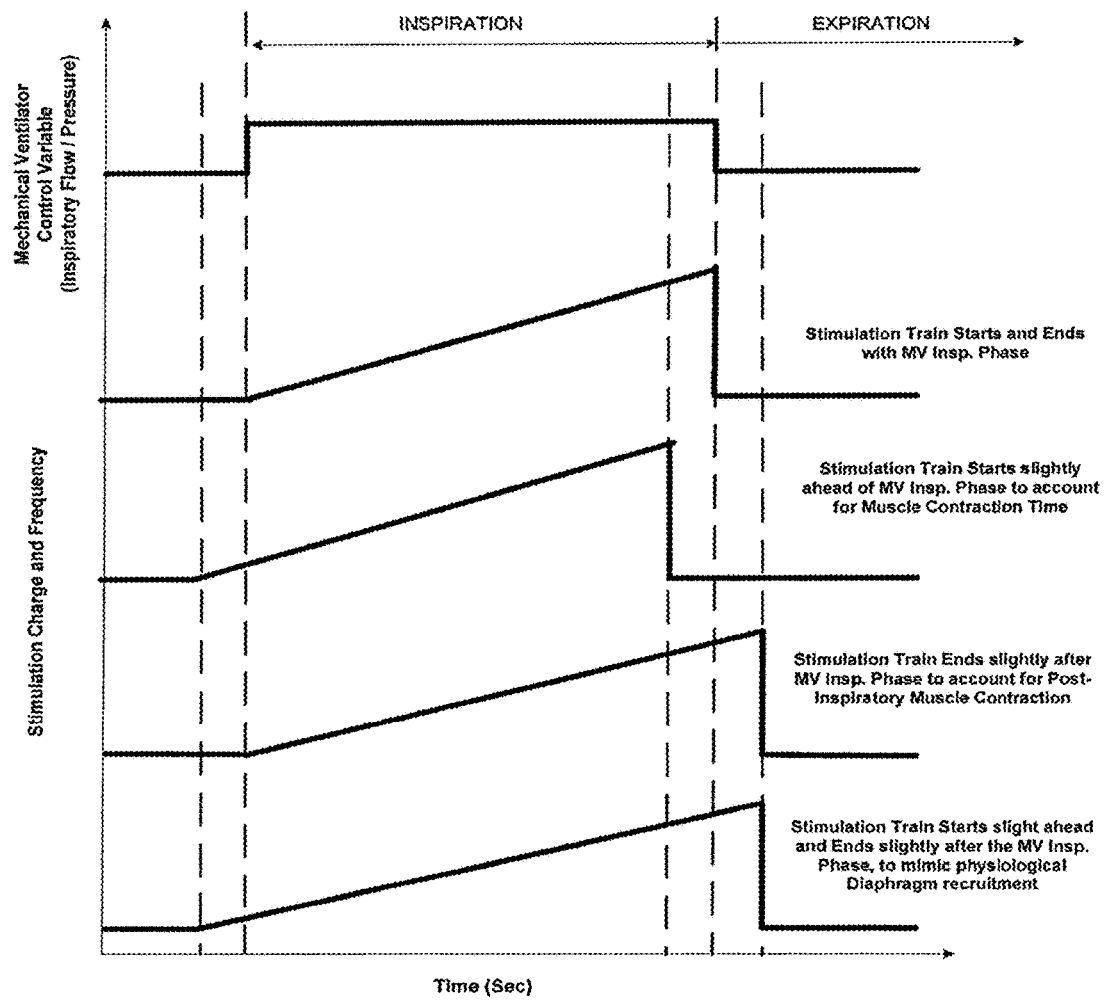
FIG. 11 illustrates examples of timing for the start time and end time of stimulation trains generated and delivered to the phrenic nerves, relative to a ventilator breath.
Figure 12:
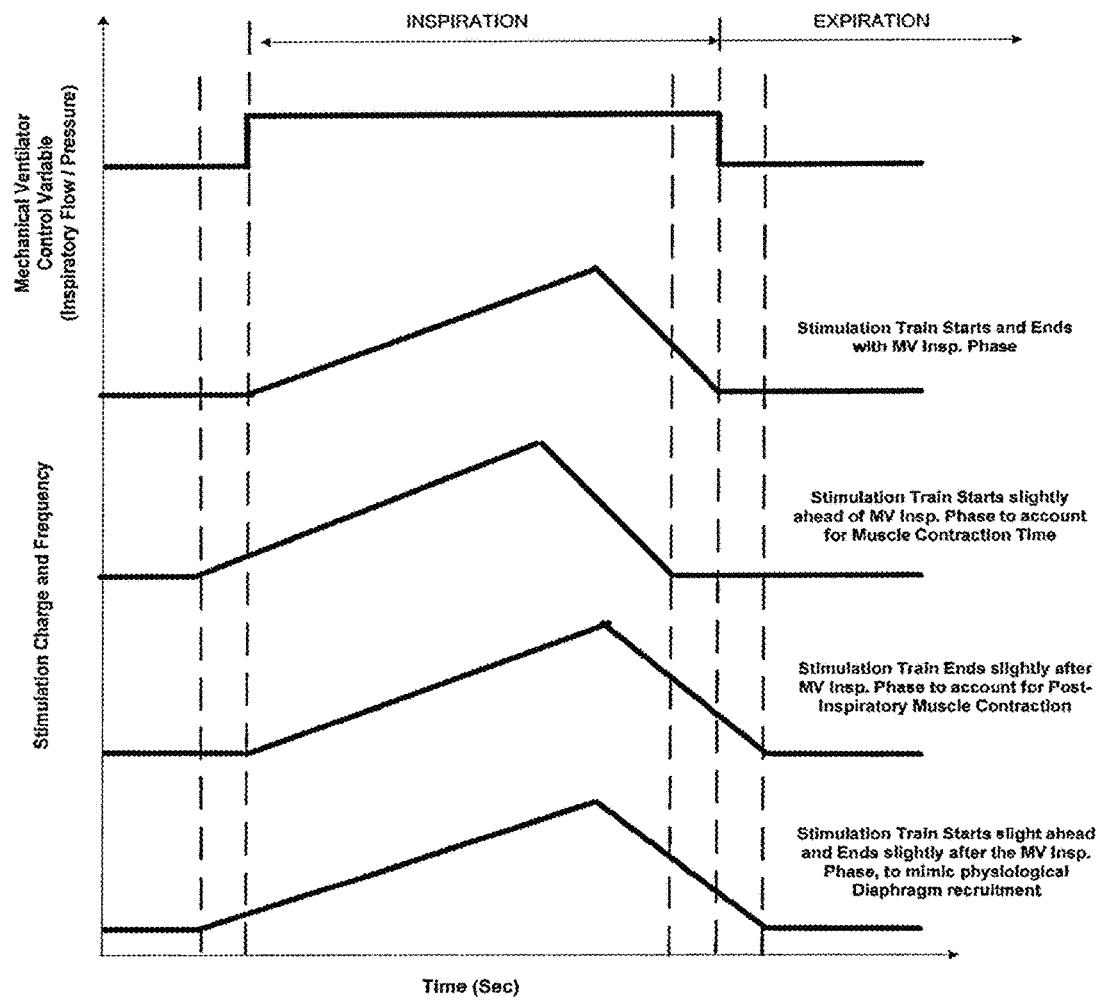
FIG. 12 illustrates other examples of timing for the stimulation trains generated and delivered to the phrenic nerves.

The first mode of the system 20 to be described herein is the Ventilator Initiated Pacing Mode. As will be described in more detail below, this mode operates the stimulator 24 in synchrony with the operation of the ventilator 32. This mode can work with any mechanical ventilator in control mode, whereby the flow or pressure is controlled by the ventilator and delivered at a pre-determined frequency (breath rate). Delivery of stimulation ramp trains generated by the stimulator 24, such as any of those shown in FIGS. 9 and 10, can be synchronized with the ventilator 32 in several ways, some of which are shown in FIGS. 11 and 12. For example, stimulation can begin at any time before, during, or after the onset of the inspiratory phase of the ventilator 32 and/or can end at any time before, during, or after the end of the inspiratory phase of the ventilator 32.

Figure 14:
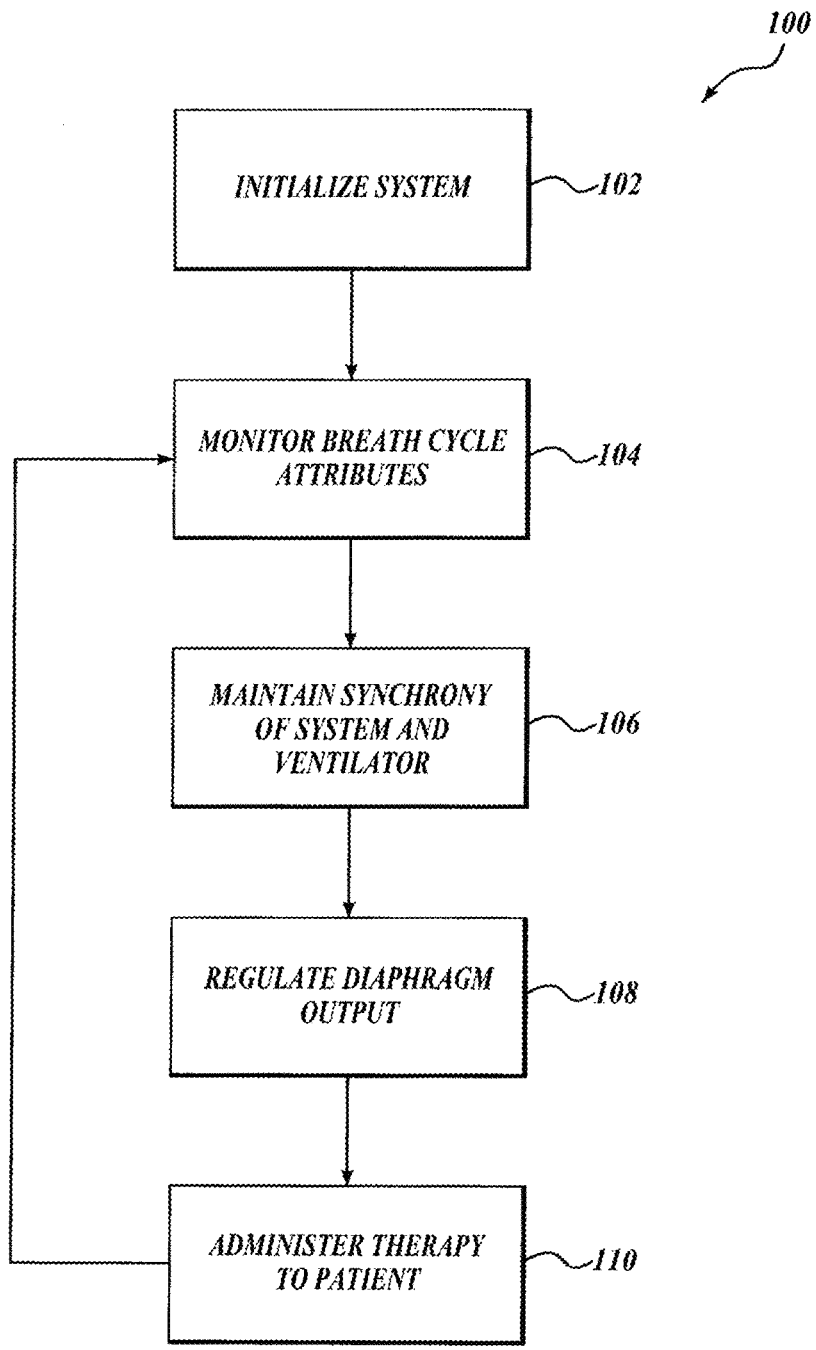
FIG. 14 illustrates one example of a process configured to carry out one or more functions of the system 20, including but not limited to the Ventilator Initiated Pacing Mode.

Turning now to FIG. 14, there is shown one example of a routine 100 configured to carry out one or more functions of the system 20, including the Ventilator Initiated Pacing Mode. As will be appreciated by one skilled in the art, the logic or routines described herein may represent one or more of any number of processing strategies such as event-driven, interrupt-driven, multi-tasking, multi-threading, and the like. As such, various acts or functions illustrated may be performed in the sequence illustrated, in parallel, or in some cases omitted. Likewise, the order of processing is not necessarily required to achieve the features and advantages, but is provided for ease of illustration and description. Although not explicitly illustrated, one or more of the illustrated acts or functions may be repeatedly performed depending on the particular strategy being used. Some of the functions carried out by the routine can be combined or can be further separated into additional steps or acts.

Figure 15:
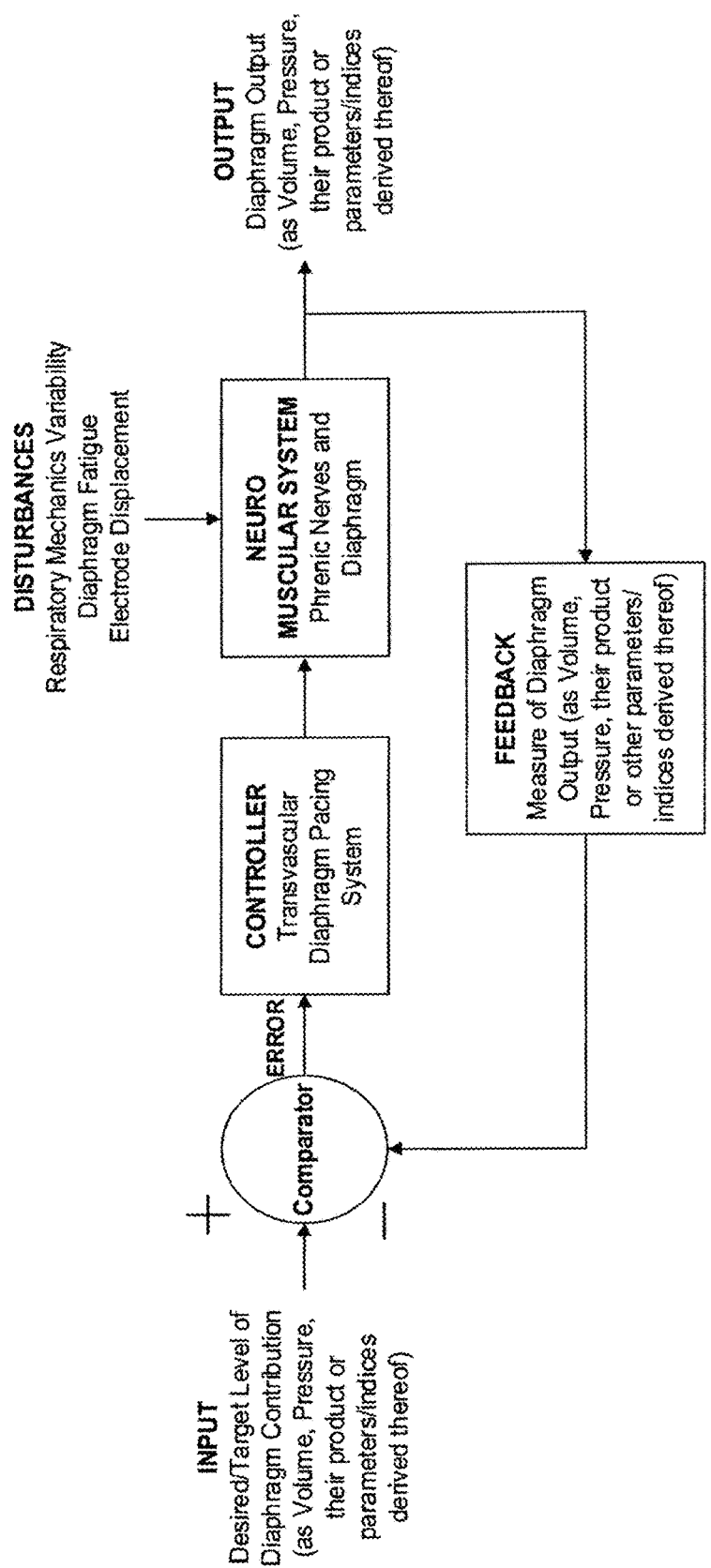
FIG. 15 illustrates one feedback scheme that may be practiced by the process of FIG. 14 and the system of FIG. 1.

As shown in FIG. 15, the routine 100 begins at block 102, where the system is initialized. Initialization allows a clinician to program the system 20, for example, by inputting via input devices 86 various system parameters according to a therapy plan. As was described in some detail above, the therapy plan can include a level of diaphragm contribution and the prescribed assist level if not already known by the system 20 or derivable from other data known by system 20. In some embodiments, the level of diaphragm contribution can be entered as either a percentage of prescribed assist level or as tidal volume, pressure or both volume and pressure, or as a parameter derived from volume and pressure.

Figure 21:
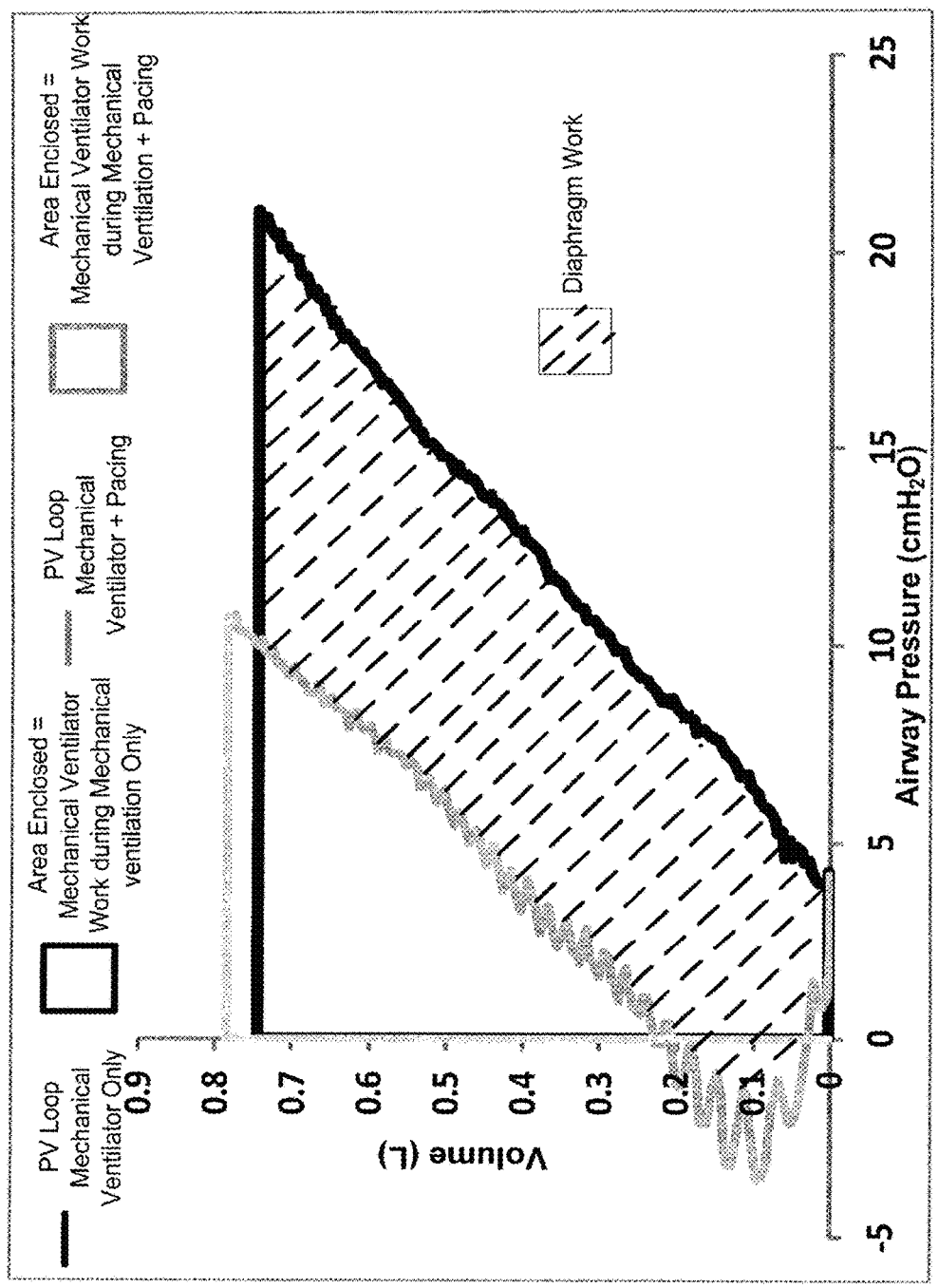
FIG. 21 is a graphical representation of one example of calculating the Work of Breathing (WOB), the calculation in turn used to regulate diaphragm contribution.

In some embodiments, the clinician can input the prescribed assist level for the patient depending upon clinical status. The prescribed assist level in some embodiments is programmed as tidal volume. Alternatively, it can also be programmed as: (1) a desired amount of pressure generated by the diaphragm; (2) the product of pressure and volume, referred to as Work of Breathing (WOB) shown in FIG. 21; (3) the integral of pressure with respect to time, referred to as Pressure-Time Product (PTP); (4) indices derived from the monitored variables, such as Pressure-Time Index (PTI); or (5) a reduction in the airway pressure attained by PPMV plus Pacing, when compared to PPMV alone. The prescribed assist level can be set in terms of one of the parameters mentioned above or as a combination of one or more of these parameters, while remaining within the scope of the claimed subject matter.

Along with the diaphragm contribution level, the clinician can program the system 20 with one or more stimulation parameters, such as amplitude, duration, frequency, etc., that are capable of recruiting the diaphragm in order to satisfy the diaphragm contribution level (e.g., in volume or pressure, or both). In other embodiments, as will be described in detail below, some of the stimulation parameters which correspond to the diaphragm contribution level, may have been previously programmed into or obtained by the system 20.

The clinician may also enter the amount of therapy to be provided per 24 hour period. For example, the clinician may wish to administer therapy for eight (8) hours out of each 24 hour period. The therapy can be administered consecutively for 8 hours, or can be segmented into time period blocks (e.g., 2 hrs., 1 hr., 30 minutes, 15 minutes, etc.), which can be either constant or variable. If variable, the time period blocks can form a repeatable pattern, if desired. The therapy may also vary the diaphragm contribution throughout the period of administered stimulation. In some embodiments, the clinician can program sigh breaths or skipped breaths, as described above with reference to FIG. 13A-C. The clinician can further enter one or more ventilation parameters, such as ventilator operating mode, breath cycle timing (i.e., breaths per minute), etc. It will be appreciated that other data may be entered by the clinician during the initialization stage for providing functionality to the system 20.

Returning to FIG. 14, the routine 100 proceeds to block 104, where the respiratory cycle of the patient and/or the ventilator are monitored. In one embodiment, the routine 100 carries out a breath detection algorithm, which uses data from the breath sensor 50 and detects the different phases of ventilator breath or a spontaneous breath, such as inspiration phase, inspiration pause, expiration phase and expiration pause. Further, the breath detection algorithm can quantify the different attributes of a breath such as duration of any of the breath phases mentioned above. The breath detection algorithm can use any of the monitored signals, such as flow, volume or pressure to evaluate a series of conditional expressions to identify and/or calculate the attributes of a breath cycle. The method of identifying and/or calculating the attributes of a breath cycle may include, but is not limited to, Slope Threshold Detection, Amplitude Threshold Detection or a combination thereof. Furthermore, the breath detection algorithm can store and/or process waveform data of the current breath or any set of previous breaths. The breath detection algorithm may also facilitate the operation of the system in an event-predictive or in an event-triggered manner. In case of detection of a spontaneous breath, the system may either stop ongoing stimulation, continue stimulating so as to add to the spontaneous breath, or skip the next breath.

Next, at block 106, synchrony between the ventilator 32 and the administration of pacing therapy is maintained. This ensures that diaphragm pacing by stimulation signals emitted by the electrodes is synchronized with each breath administered by the ventilator 32. If an uncoupling is suspected, pacing may be skipped and resumed as soon as the ventilatory pattern stabilizes again. In other embodiments, the pacing can continue while synchrony is reestablished. In some embodiments, synchrony is determined by comparing the attributes of at least one previous breath cycle (e.g., 12 breaths per minute, etc.) with the attributes of the current breath cycle of the ventilator 32 as determined via processing of the signals from the breath sensor 50 and/or one or more of the sensors 48.

From block 106, the routine proceeds to block 108. At block 108, the diaphragm output (e.g., tidal volume, pressure, or a combination of the two) is regulated to ensure the programmed prescribed assist level is satisfied. In this regard, in some embodiments, the system 20 monitors the data from one or more of the sensors 48 and/or sensor 50 for determining the diaphragm contribution (tidal volume, pressure, or both) for each ventilator breath. This may be calculated from the measured output (i.e., the sum of diaphragm contribution and ventilator contribution) of each ventilator breath or can be calculated directly from the sensor data. If the diaphragm output (or diaphragm contribution) from the previous administered stimulation signal is within a preselected range, the programmed stimulation parameters are maintained, and will be subsequently employed to generate the stimulation train for therapy administration at the next breath.

If the calculated diaphragm contribution resulting from the last administered stimulation signal differs from the target diaphragm contribution value by more than a preselected amount, the stimulation parameters may be modified (e.g., amplitude and/or duration are increased) so as to maintain the diaphragm output within a desired range. Such a difference between the calculated diaphragm contribution responsive to the last administered stimulation signal and the programmed diaphragm contribution value can be seen as a change in either the pressure (in Volume-Controlled Modes/Ventilators) or as a change in tidal volume (in Pressure-Controlled Modes/Ventilators) or as a change in any signal sensed by one or more of the sensor(s) 48 or sensor 50. The modified stimulation parameters are then stored in memory. In some embodiments, the system 20 operates in accordance with a "closed-loop" feedback scheme to regulate the diaphragm output during operation of the system 20, one example of which is shown in FIG. 15.

In some embodiments, an evaluation is carried out to determine the reason for such a drop in tidal volume or pressure. For example, in some embodiments, the discrepancy in reaching the diaphragm contribution target may be due to a displacement of a stimulation electrode away from an optimal position. In other embodiments, the discrepancy or variability in tidal volume or pressure between breaths can be attributable to either changing respiratory mechanics of the patient or to time-dependent fatigue of the higher force producing fast-fatigable (Type IIb) fibers.

Figure 16:
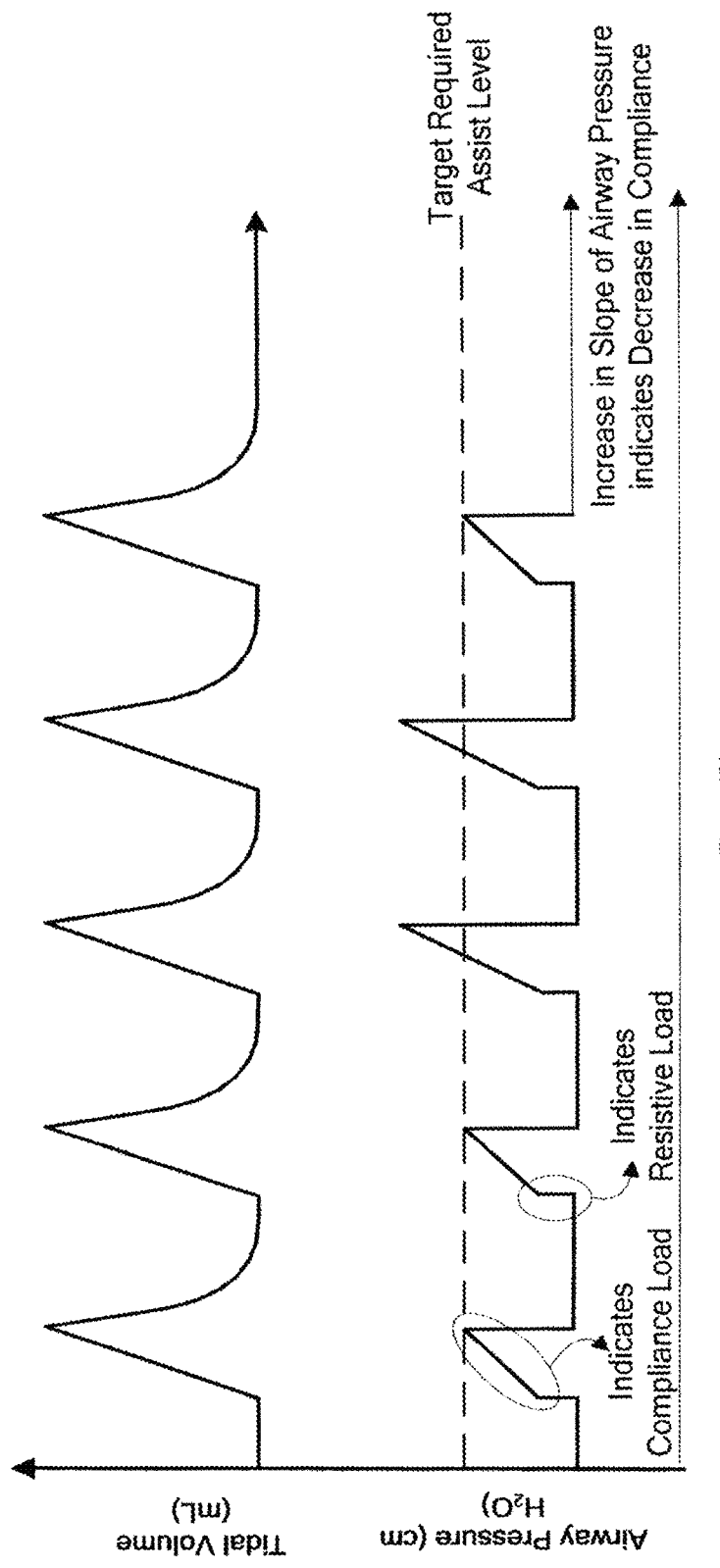
FIG. 16 illustrates one example of a change in respiratory mechanics during pacing in synchrony with a volume controlled mechanical ventilator.

Changes in respiratory mechanics may include changes in airway resistance and/or compliance of the lungs/chest wall. For example, in the embodiment shown in FIG. 16, the tidal volume is controlled during all breaths, representing a ventilator operating in a Volume Controlled Mode. If any changes occur to the resistive load or the compliance load, these will be reflected as changes in the airway pressure represented in the plot below the tidal volume. In the example of FIG. 16, the first two breaths illustrate the baseline level of airway pressure when pacing the diaphragm in synchrony with the ventilator 32. On the 3rd breath, the system encounters a change in compliance load, which can be inferred from the increased peak airway pressure and change in slope of the airway pressure waveform.

In the 4th breath shown in FIG. 16, the system 20 can validate the measured drop in compliance and assumes it is due, for example, to a reduction in force contribution of fast fatigable Type IIb fibers. By the 5th breath, the system 20 has adjusted its pacing parameters to restore the desired level of diaphragm contribution (negative pressure) to the overall ventilatory assist system, thereby returning the airway pressure to the prescribed assist level.

It will be appreciated that similar principles can be applied to a pressure controlled ventilator, where changes in respiratory mechanics may be indicated by changes in tidal volume between breaths. The system 20 may be configured to adaptively modify the pacing parameters to return the tidal volume to the prescribed assist level.

Figure 17A:
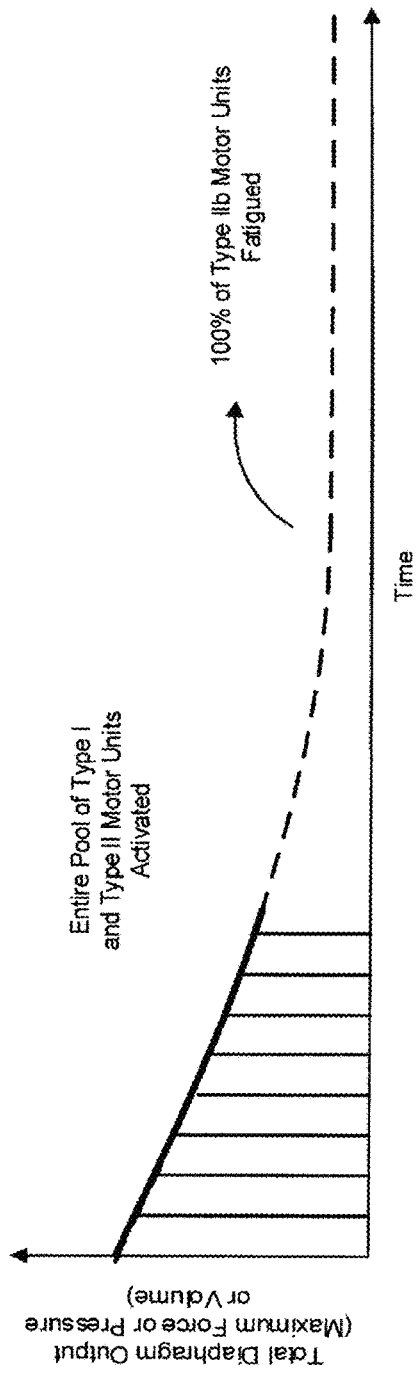
FIG. 17A-B illustrate examples of maintaining the diaphragm output at a prescribed level despite a time dependent fatiguing and drop-out of stimulated Type IIb fibers.
Figure 17B:
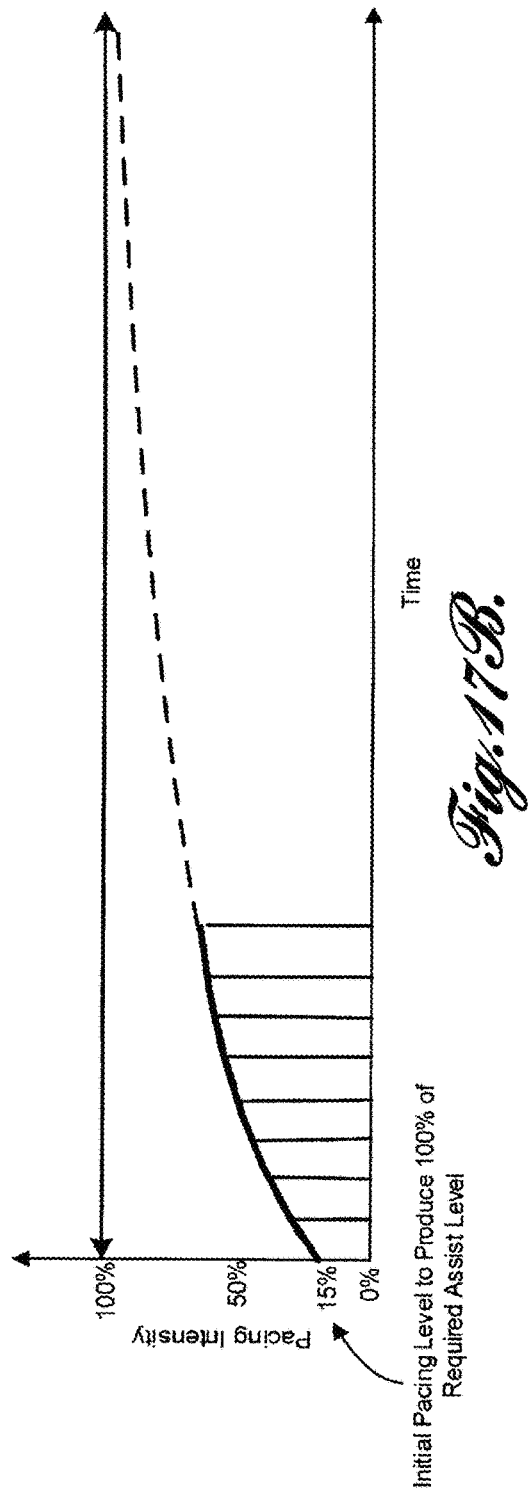
Figure 18:
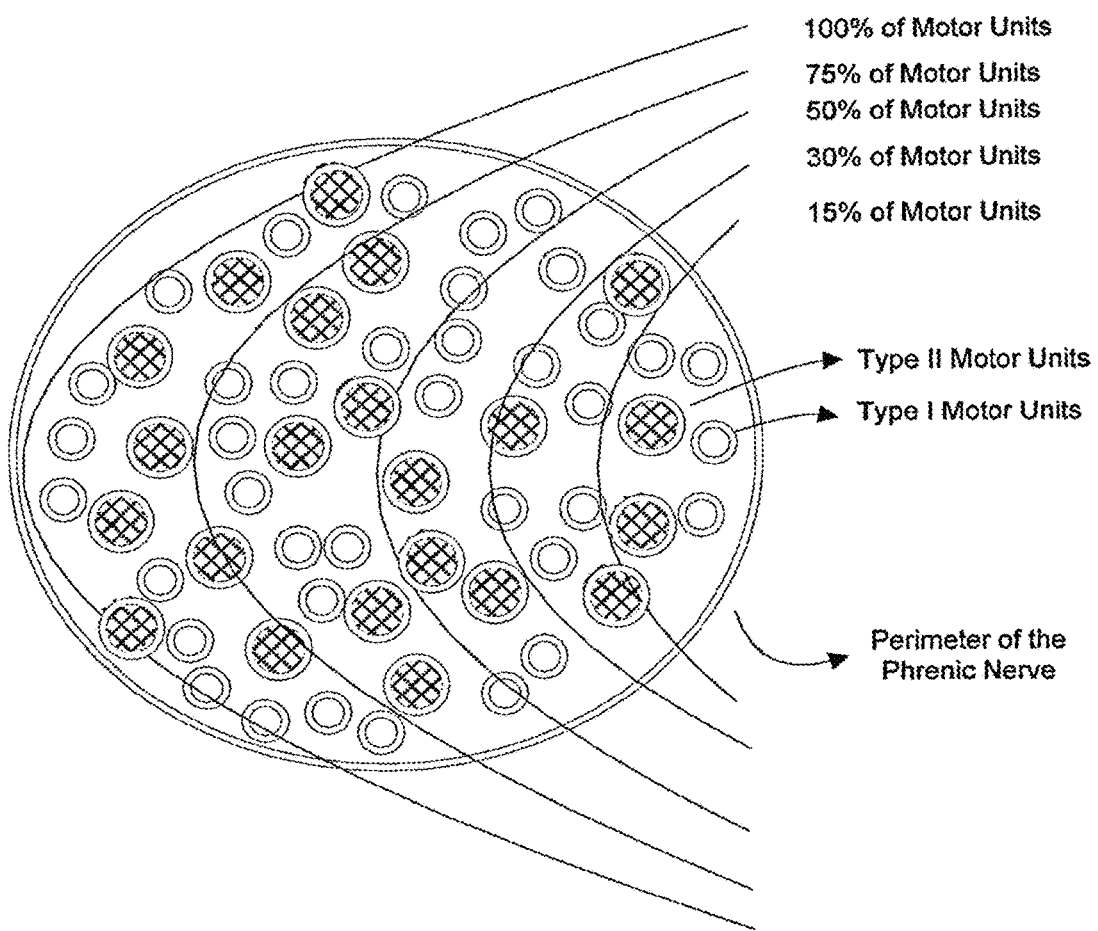
FIG. 18 illustrates one example of progressive recruitment of nerve axons across the cross-section of the phrenic nerve and their associated motor units by increasing the pacing intensity.

As described above, the discrepancy or variability in tidal volume or pressure between breaths can be also attributable to time-dependent fatigue of the higher force producing fast-fatigable (Type IIb) fibers. For example, FIG. 17A illustrates a natural progressive decline in the percentage of Type IIb Fast Fatigable Motor Units contributing to force development. Initially, Type IIb Motor Units can produce much larger forces than Type I Motor Units and their larger diameter axons are also easiest to be recruited by electrical stimulation. Therefore, a low level of intensity of phrenic nerve stimulation is initially sufficient to produce the diaphragm contribution level, as illustrated by FIG. 17B. As shown schematically in FIG. 18, initially perhaps only 15% of all motor units in a phrenic nerve need to be recruited by the system 20 to meet the prescribed force/pressure levels of the diaphragm contribution.

Figure 17C:
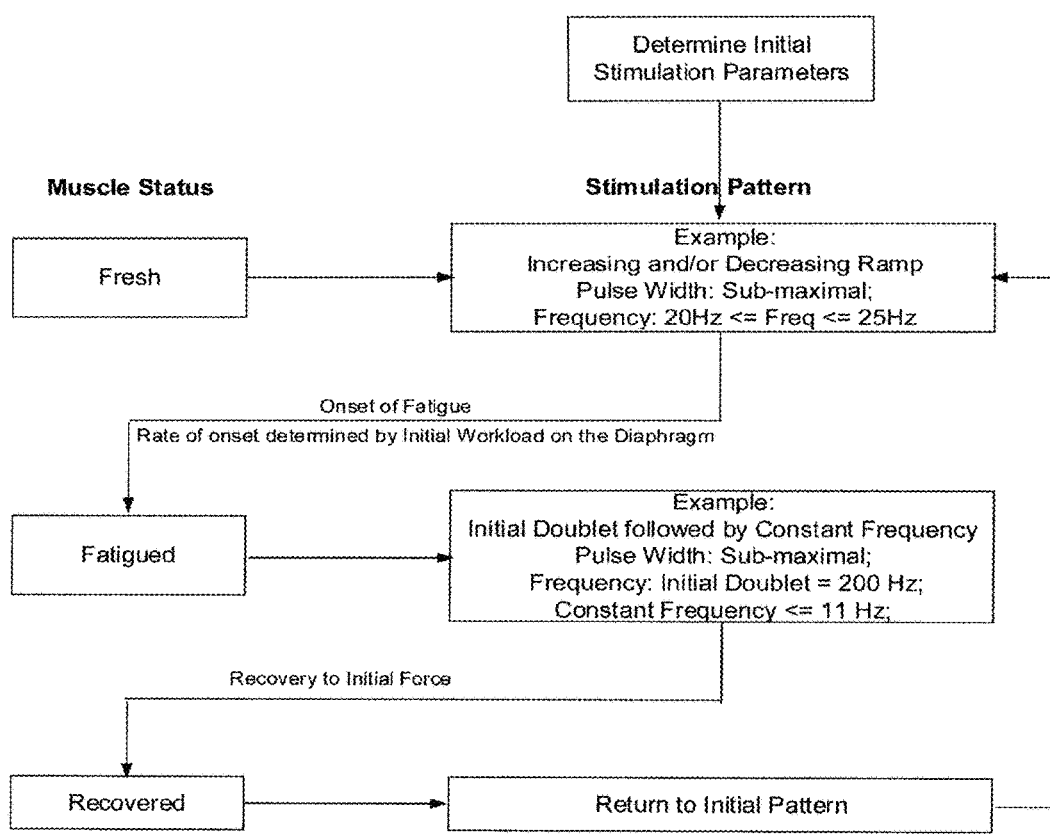
FIG. 17C illustrates a process for using doublets to enhance force in fatiguing muscle.

As shown in FIG. 17, Type IIb Motor Units tend to fatigue and produce less force with the passage of time, leading to a decline in the force (Diaphragm Contribution) below the programmed level of diaphragm contribution. To maintain the diaphragm contribution, the intensity of stimulation can be progressively increased so as to recruit additional Type I and Type IIa Motor Units. As a result, the stimulation spreads across a higher cross-sectional area (e.g. 30%) of the phrenic nerve to recruit more Type I and Type II Motor Units and the prescribed force is produced.

The force declines again as the Type IIb Motor Units present in the newly activated cross-section of the phrenic nerves, fatigue in turn. At this point the pacing intensity is increased again by the pacing control system in order to activate an even larger cross-sectional area of the phrenic nerve, recruiting more Motor Units to reestablish the force output. This progressively increasing activation of the phrenic nerve continues and finally up to 100% of the phrenic nerve motor units may be recruited. Eventually all the Type IIb Motor Units are knocked out by fatigue and only the Type I and Type IIa Motor Units continue to contribute force.

It will be appreciated that the increase in the stimulation may be a simple linear equation or a complex equation with weights assigned to the proportion of available fibers and their fatigue resistant properties. The loss of force may be attributed specifically to the fatigue of the fast fatigable fibers, using parameters such as Maximum Relaxation Rate and half-relaxation time. The changes in slope of the first half of the diaphragm relaxation curve indicative of the relative contribution of Type I and Type II fibers to force development may also be used. Other parameters specific to fatigue such as Pressure-Time Index, Expiratory Time Constant, EMG (and any derived parameters thereof such as power spectrum), Ratio between slow and fast twitch amplitudes, may also be employed to infer the varying conditions and to determine the modified stimulation parameters.

In another embodiment, the closed-loop control strategy may include using doublets/triplets in response to contractile slowing accompanying fatigue of the diaphragm Motor Units. When fatigue is detected by the system 20, the stimulation pattern is automatically changed to include doublet/triplets and otherwise lower stimulation frequency, as this form of stimulation is known in the art to optimize force production in fatiguing/fatigued motor units. Once the fatigued motor units have recovered their strength, the stimulation pattern can again be changed to moderate stimulation frequency with or without doublets. This closed-loop scheme allows for continuous pacing of the diaphragm irrespective of the onset or progression of fatigue, also reduces the number of stimulation pulses delivered and protects the muscle from potential injury that could be caused by over-stimulation.

Figure 24:
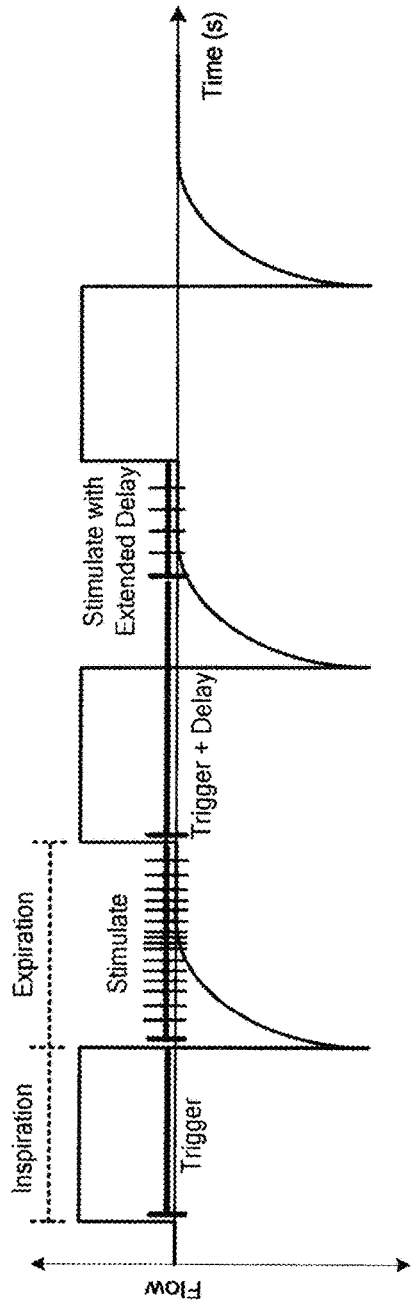
Figure 25:
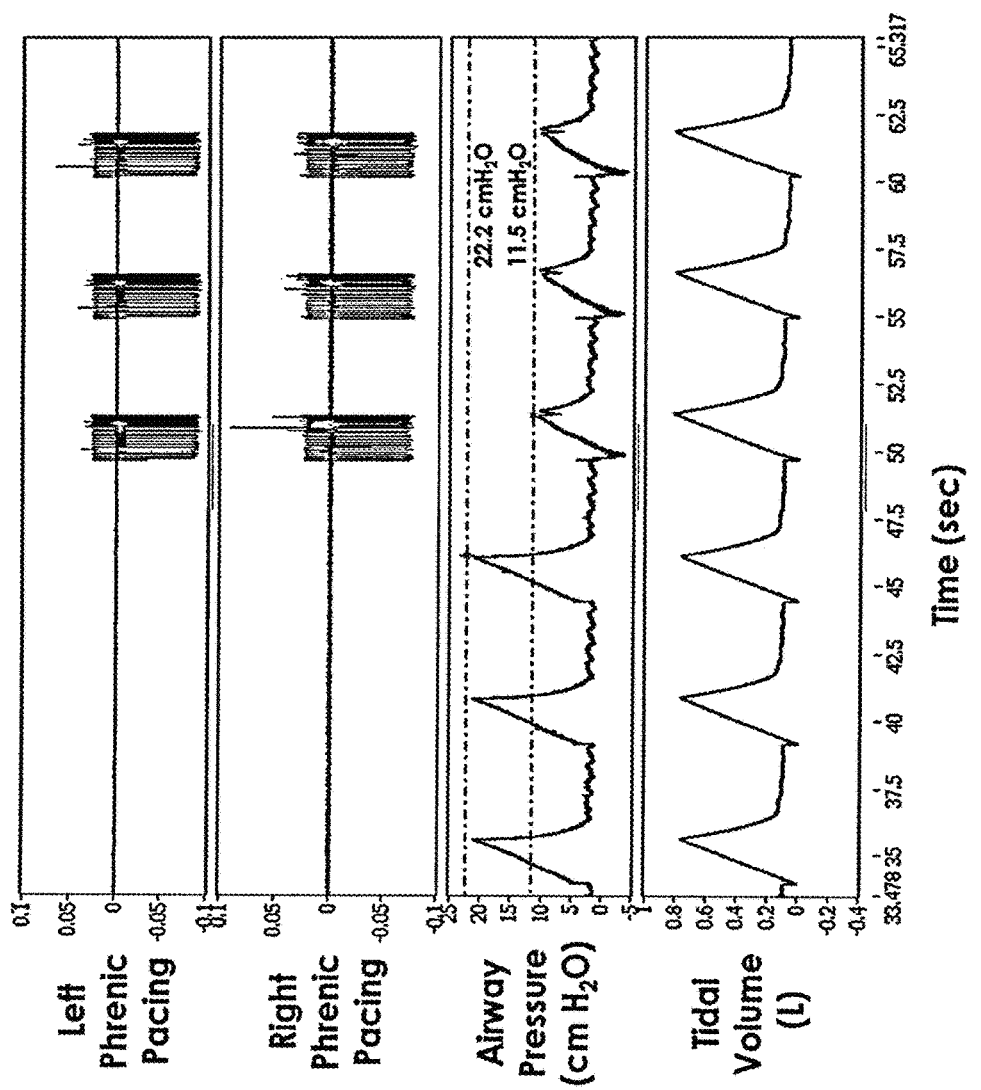
FIG. 25 is a graphical representation of airway pressure data obtained from a volume controlled ventilator with and without stimulation.

Returning to FIG. 14, the stimulation therapy is administered at block 110. Administration of the stimulation therapy includes generation of a stimulation signal, such as a stimulation or ramp train. Depending on the result of block 108, the stimulation signal is generated in accordance with either the original stimulation perimeters or the stimulation parameters as modified in block 108 described above. Delivery timing of the stimulation ramp train is also determined at block 110. For example, the routine can determine the appropriate timing for phrenic nerve stimulation in relation to the actual breath cycle of the ventilator 32. Generally described, the routine controls the timing of stimulation according to pre-defined rules, based on parameter estimates from the breath detection algorithm, etc. The pre-defined rules can include whether stimulation begins at any time before, during, or after the onset of the inspiratory phase of the ventilator 32, which is shown in FIGS. 11 and 12, or whether stimulation begins during the expiratory phase, as shown in FIG. 24.

Figure 23:
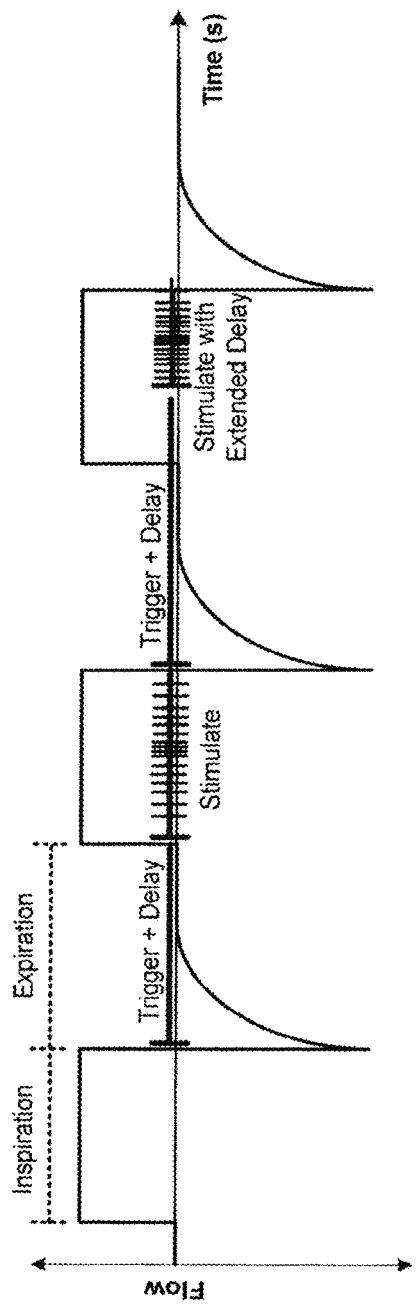
FIGS. 23 and 24 illustrate examples of the timing of administered stimulus in relation to the phases of the breath cycle.

For example, depending on the ventilator mode, the system 20 can trigger off pressure or airflow signals. Once the inspiration/expiration phases have been determined, such as in block 104, to stimulate during the inspiration phase, the stimulation train can either be started by triggering off the start of the expiration phase followed by a delay or the start of the inspiration phase, as shown in FIG. 23. Triggering off the start of the expiration phase allows stimulation to be generated prior to the start of the inspiration phase to maximize diaphragmatic force during the inspiration phase. In addition, stimulation during the expiration phase can be achieved by triggering off the start of the expiration phase or the start of the inspiration phase with a delay, as shown in FIG. 24. While using the inspiration or expiration start is preferred, the end of the inspiration/expiration periods could conceivably be used as well. Furthermore, it is also possible to provide delayed stimulation such that stimulation would begin in the middle of the inspiration phase for example.

Once timing is determined, the routine at block 110 delivers the stimulation pulses to the stimulating electrodes 28 at the appropriate time for transmission therefrom. The routine returns to block 104 until the time period for therapy has expired or a clinician halts operation of the system 20.

In some embodiments, the system 20 may assist the clinician in determining the appropriate level of diaphragm contribution to be input into the system 20. In that regard, the diaphragm contribution can be dependent on the condition of the patient's diaphragm. For example, in a patient that has only a maximum diaphragm output of 750 mL and the clinician intends to target an assist level of 500 mL, the clinician may unknowingly choose a diaphragm contribution level that would require delivery of the maximum stimulation charge, which will cause premature fatigue, etc. Given this patient's present diaphragm condition, the clinician may wish to choose a much lower percentage so that the stimulation charge is in-between the threshold charge and the supra-maximal charge.

Thus, in some embodiments, in order to appropriately select the diaphragm contribution level, the condition of the diaphragm and the respiratory system is first assessed by the system 20. In that regard, the system 20 is configured to run one or more assessments on the patient's diaphragm and/or respiratory mechanics. The assessment determines the maximum diaphragm output (in volume, pressure, or both) and other parameters such as the fatigue characteristics of the diaphragm, the resistance, compliance and relaxation characteristics of the respiratory system and its components, etc. The assessment can be also run in-between or during periods of the operation of the system 20 in synchrony with the ventilator 32. These tests can either be run by shortly disconnecting the patient from the ventilator 32 and pacing the diaphragm in isolation or can be run with the patient connected to the ventilator 32 by employing a sequence of pauses in the operation of the ventilator 32 during which the diaphragm is paced in isolation. The sequence of pauses may either be employed manually by the clinician, or natural pauses that are part of a regular ventilator breath cycle (such as an End-Inspiratory Pause or an End-Expiratory Pause) may be automatically identified and used by the system 20.

Generally described, after the flow of gas from the ventilator 32 is momentarily occluded, the maximal static pressures generated by the diaphragm in response to supra-maximally stimulating the phrenic nerves to elicit twitch, ramp, or tetanic contractions of the diaphragm are measured as well as the diaphragm relaxation characteristics during the inspiration and expiration phases. The assessment can pace the diaphragm in isolation with a preset duty cycle to assess diaphragm function with regard to its strength and endurance properties. From the data sensed by one or more sensors 48 and/or the sensor 50, measures and/or indices can be derived that include, but are not limited to, Maximum Static/Dynamic Inspiratory Pressures, Inspiratory Capacity, Pressure-Volume loop relationships, Work of Breathing, Pressure-Time Product, Pressure-Time Index, EMG, Maximum Relaxation Rate, and Expiration Time Constant. Diaphragm fatigue can be induced by continuous or intermittent stimulation of the phrenic nerves to assess endurance limits and to detect the presence of low frequency and/or high frequency fatigue. As the normal values for most of the calculated or derived parameters have a wide normal range, serial measurements set apart in time ranging from a few minutes to days, can be done on a patient by the pacing system to provide a complete picture of evolving changes in the diaphragm strength and endurance of the patient.

In some embodiments, a knowledge-based algorithm may be used to monitor instantaneous and/or trend data of the monitored signals. Such instantaneous and/or trend data may allow the assessment to predict weaning readiness of the patient and/or a time course for weaning. Such capability can also be extended to make the diaphragm assessment tests as a standalone screening and/or confirmatory tool by clinicians in the ICU, as the method of transvascular pacing of the diaphragm enables the clinician to assess the true status of the diaphragm in the absence of confounding factors (such as decreased central drive) usually associated with voluntary breathing maneuvers.

Figure 19:
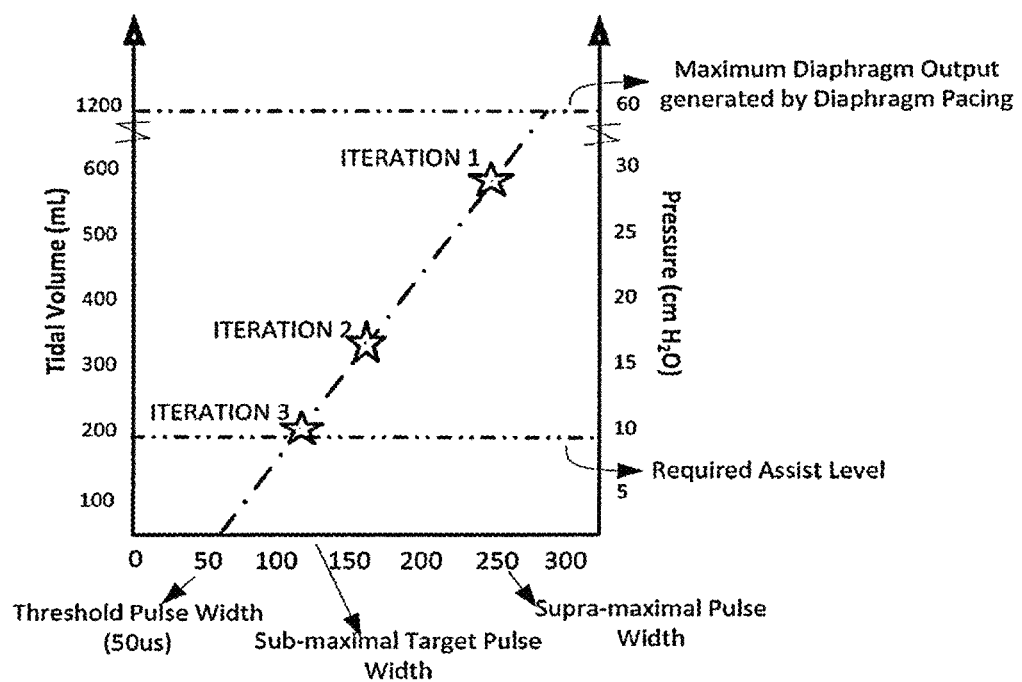
FIG. 19 is a graphical representation for scaling the contribution of the system of FIG. 1 to prescribed assist level and determining one or more initial pacing parameters using, for example, a binary algorithm.

Once the maximum diaphragm output is determined, the diaphragm contribution level can be chosen with knowledge of the relationship between the prescribed assist level and the maximum diaphragm output. In order to understand this relationship, the controller 60 in some embodiments, via one or more subroutines, can recursively estimate the percentage of maximum diaphragm output required to generate 100% of the prescribed assist level. Of course, this and other calculations can be made on a separate computer system and imported or otherwise inputted into the controller 60 prior to operation of the system 20. One example of this recursive estimate is shown in FIG. 19.

In some embodiments, and described generally above, the clinician has the option to adjust the diaphragm contribution during operation of the system 20 from 0 to 100% of the prescribed assist level, as illustrated by the dial of FIG. 20, depending upon the status of the patient and the therapeutic goal.

Figure 20A:
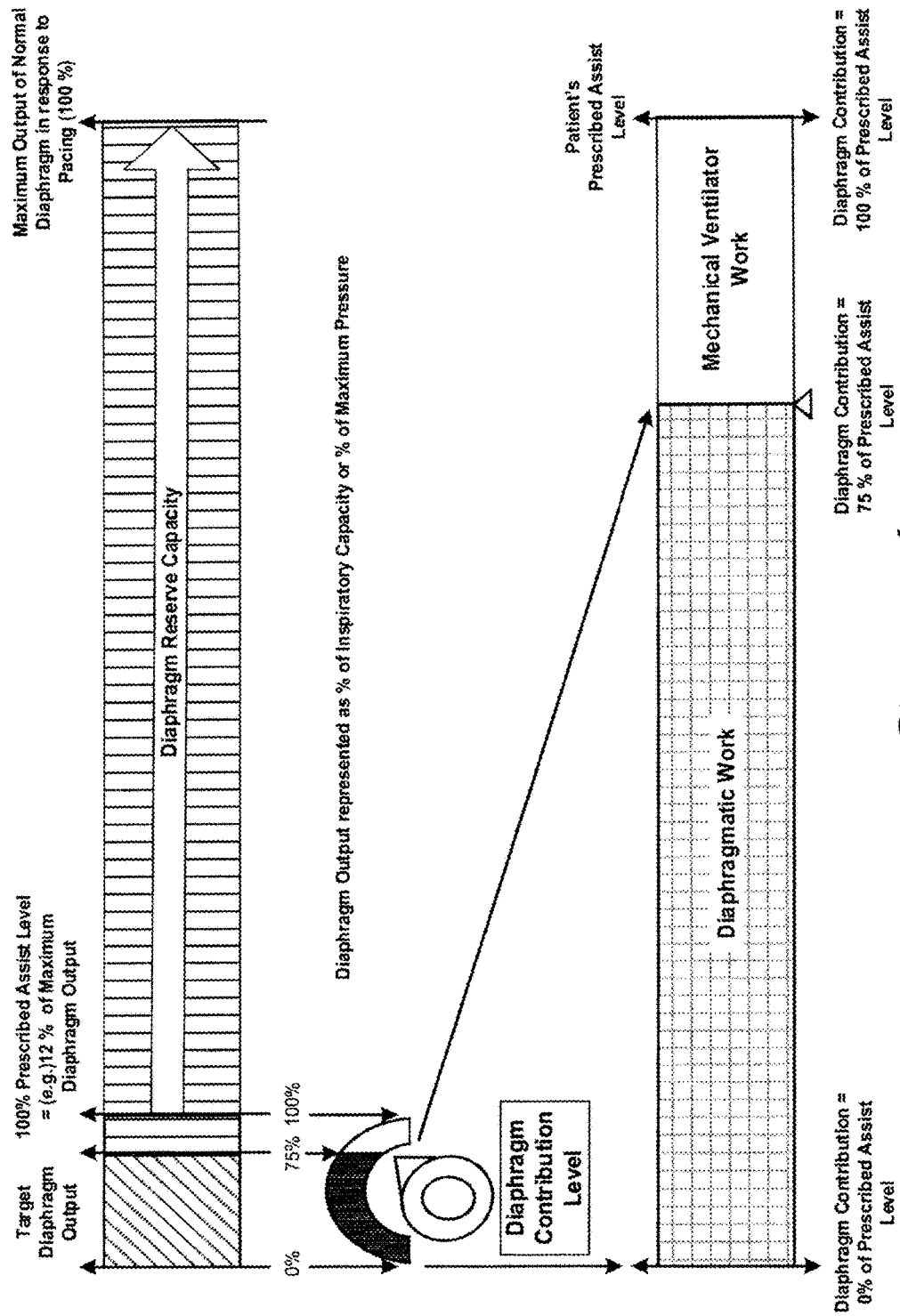
FIG. 20A is a schematic representation of one example of scaling the contribution of the system of FIG. 1 to diaphragm response.
Figure 20B:
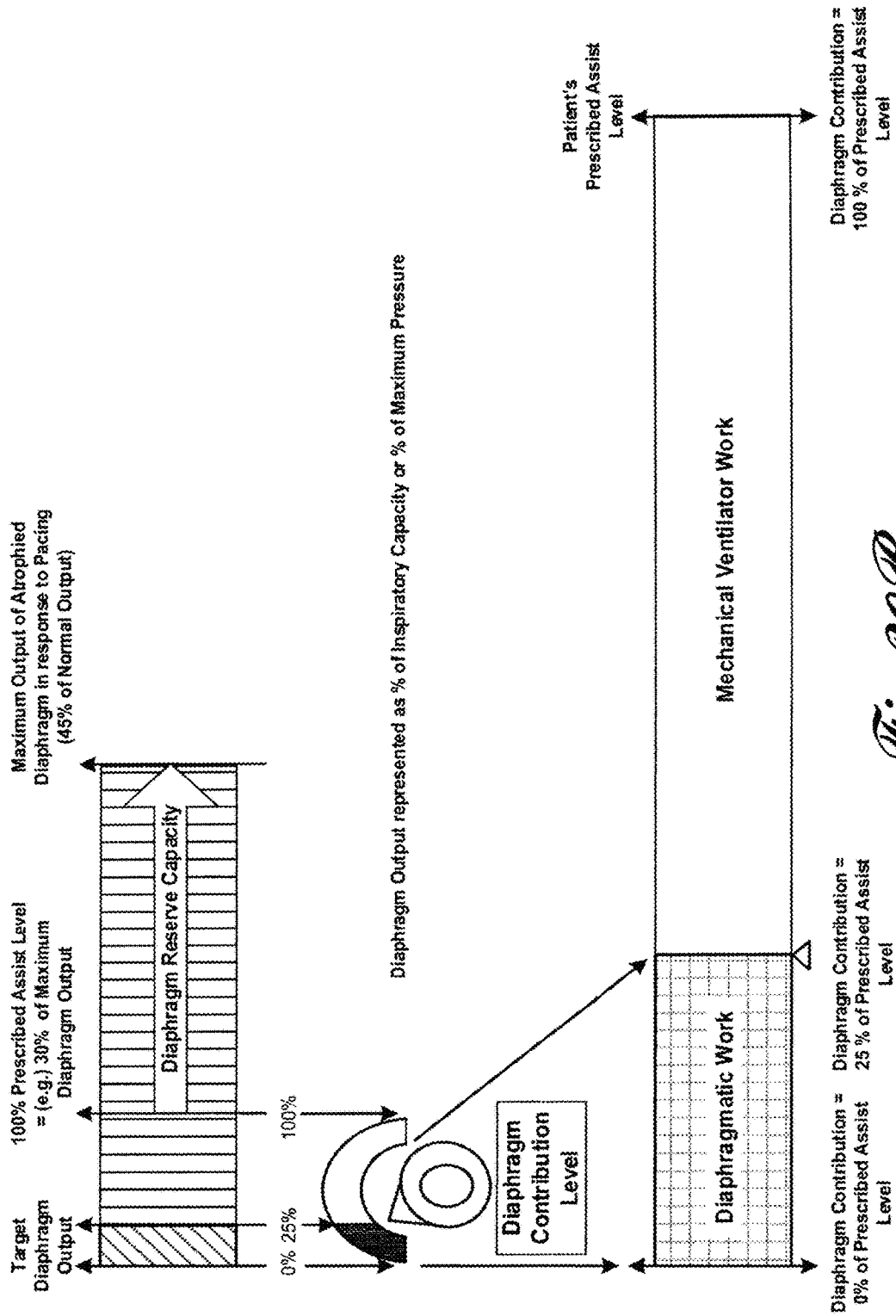
FIG. 20B is a schematic representation of another example of scaling the contribution of the system of FIG. 1 to diaphragm response.

FIG. 20A illustrates an example of setting the desired diaphragm contribution to 75% of the prescribed assist level (i.e., the target diaphragm contribution level). In this example, the remaining 25% of the ventilatory work is carried out by the ventilator 32. The clinician can therefore adjust the ventilator settings to contribute 25% of the ventilatory work, either as tidal volume or as pressure assist, as illustrated by the bottom plot of FIG. 20A. FIG. 20B illustrates another example of setting the desired diaphragm contribution to only 25% of the prescribed assist level (i.e., the target diaphragm contribution level). In this example, the remaining 75% of the ventilatory work is carried out by the ventilator 32. The clinician can therefore adjust the ventilator settings to contribute 75% of the ventilatory work, either as tidal volume or as pressure assist, as illustrated by the bottom plot of FIG. 20B. Alternatively, the PPMV can be set to a mode where the remaining portion of the prescribed assist level is determined and adjusted automatically by the ventilator on an Inter-Breath or Intra-Breath basis (e.g. Pressure Regulated Volume Control Mode). In some embodiments, the system 20 also calculates or otherwise obtains the stimulation characteristics that correspond to the diaphragm contribution. In other embodiments, the clinician can enter data indicative of these stimulation characteristics.

In some embodiments, the condition of the diaphragm is periodically reassessed after the therapy has been administered for a period of time (e.g. 12 hours, 1 day, etc.). For example, as described briefly above with regard to the closed-loop control method for regulating the diaphragm output, the variability in volume or pressure between breaths in some instances is attributable to changing respiratory mechanics of the patient, including changes to airway resistance and/or compliance of the lungs/chest wall. In other embodiments, the diaphragm muscle, through the administration of the therapy, has strengthened, and thus, the diaphragm contribution can be increased or the intensity of stimulation can be decreased to adjust the diaphragm contribution. In these cases, it may be beneficial to periodically reassess the diaphragm and optimize pacing therapy accordingly, after therapy has been initiated.

Figure 22:
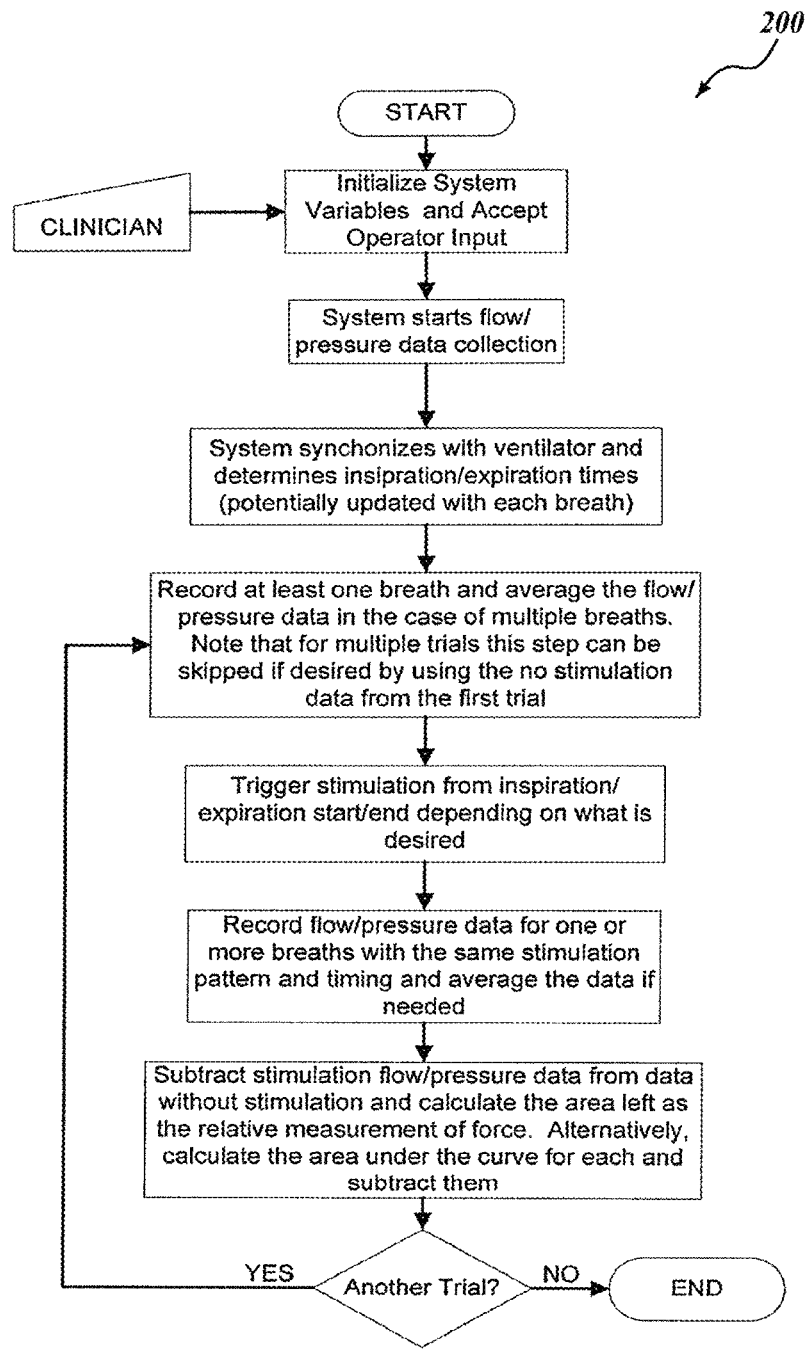
FIG. 22 is one example of a routine for assessing the diaphragm without disconnecting the patient from the ventilator.

One example of a routine for measuring changes in the diaphragm condition without removing the patient from the ventilator 32 is shown in FIG. 22. Similar to the diaphragm assessment described above, a successive approximation routine in some embodiments can be used to determine the optimal parameters of stimulation for the patient.

As best shown in FIG. 22, the routine 200 begins with the clinician providing the initial system parameters, which may include maximum allowable stimulation parameters. Stimulation parameters can be provided either as a predefined stimulation train with fixed duration such that the stimulation train is fully defined by the user using methods as previously described or as a stimulation train in which the number of pulses and the train duration are based on the detected ventilator inspiration time. Next, the routine carries out the breath detection algorithm to detect the inspiration and expiration phases using the flow/pressure data sensed by breath sensor 50. In addition, the flow and pressure data for one or more breaths without stimulation are collected and stored.

Depending on the ventilator mode, the system 20 can trigger off pressure or airflow signals. Once the inspiration/expiration phases have been determined, to stimulate during the inspiration phase, the stimulation train can either be started by triggering off the start of the expiration phase followed by a delay or the start of the inspiration phase, as shown in FIG. 23. Triggering off the start of the expiration phase allows stimulation to be generated prior to the start of the inspiration phase to maximize diaphragmatic force during the inspiration phase. In addition, stimulation during the expiration phase can be achieved by triggering off the start of the expiration phase or the start of the inspiration phase with a delay, as shown in FIG. 24. While using the inspiration and expiration start are preferred, the end of the inspiration/expiration periods could conceivably be used as well. Furthermore, it is also possible to provide delayed stimulation such that stimulation would begin in the middle of the inspiration phase for example.

Figure 26:
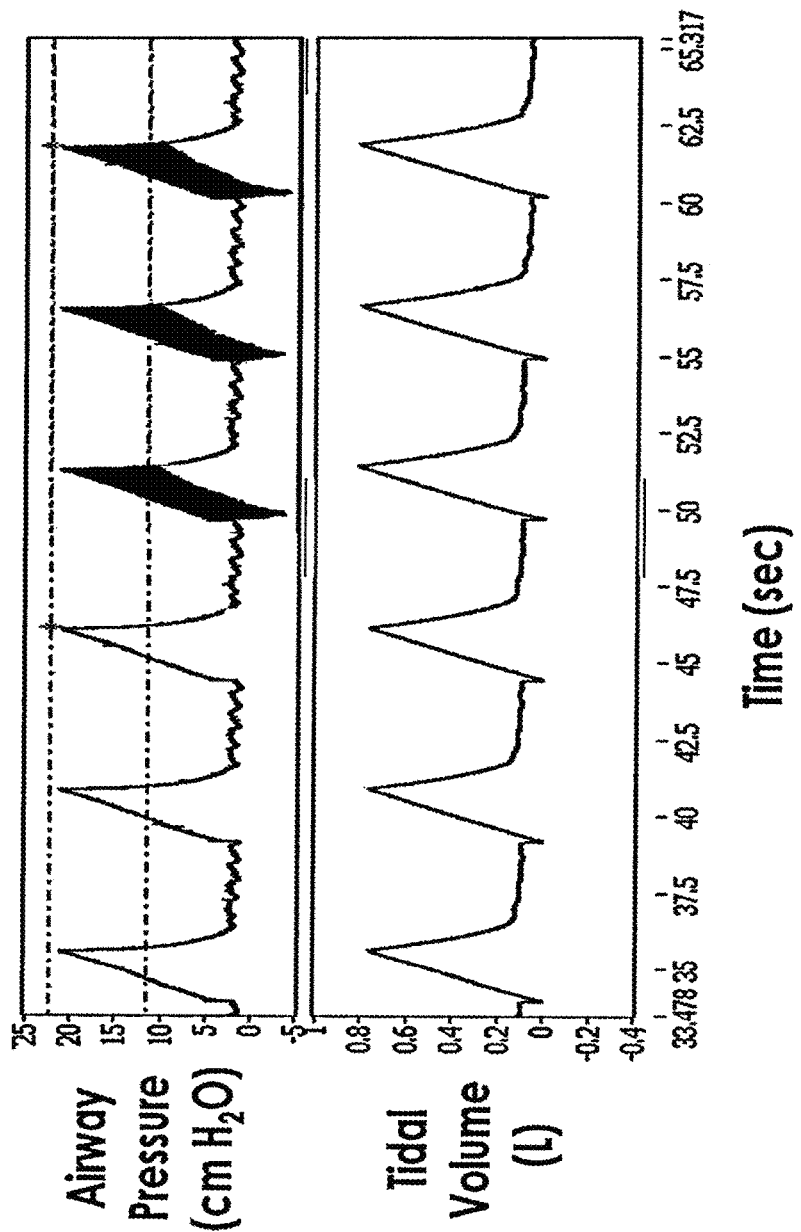
FIG. 26 is a graphical representation of one example of calculating the Pressure-Time Product, the calculation in turn used to regulate diaphragm contribution.

Flow, volume, and/or pressure data, or derived parameters thereof, for at least one breath with stimulation is recorded. For the data with stimulation as well as without, if more than one breath of information has been recorded the data can be averaged together. The collected flow/volume/pressure data with stimulation is then subtracted from the collected flow/volume/pressure data without stimulation. The difference, calculated as an area (and shown as the blacked-out area), can be used as a relative measurement of force generated by the diaphragm, and is shown in FIG. 26. In the case of a pressure controlled ventilation, the difference in volume (area under flow curve) would be used as the measurement. In the case of a volume controlled ventilator, the area under the pressure graph would be used as the measurement.

Figure 27:
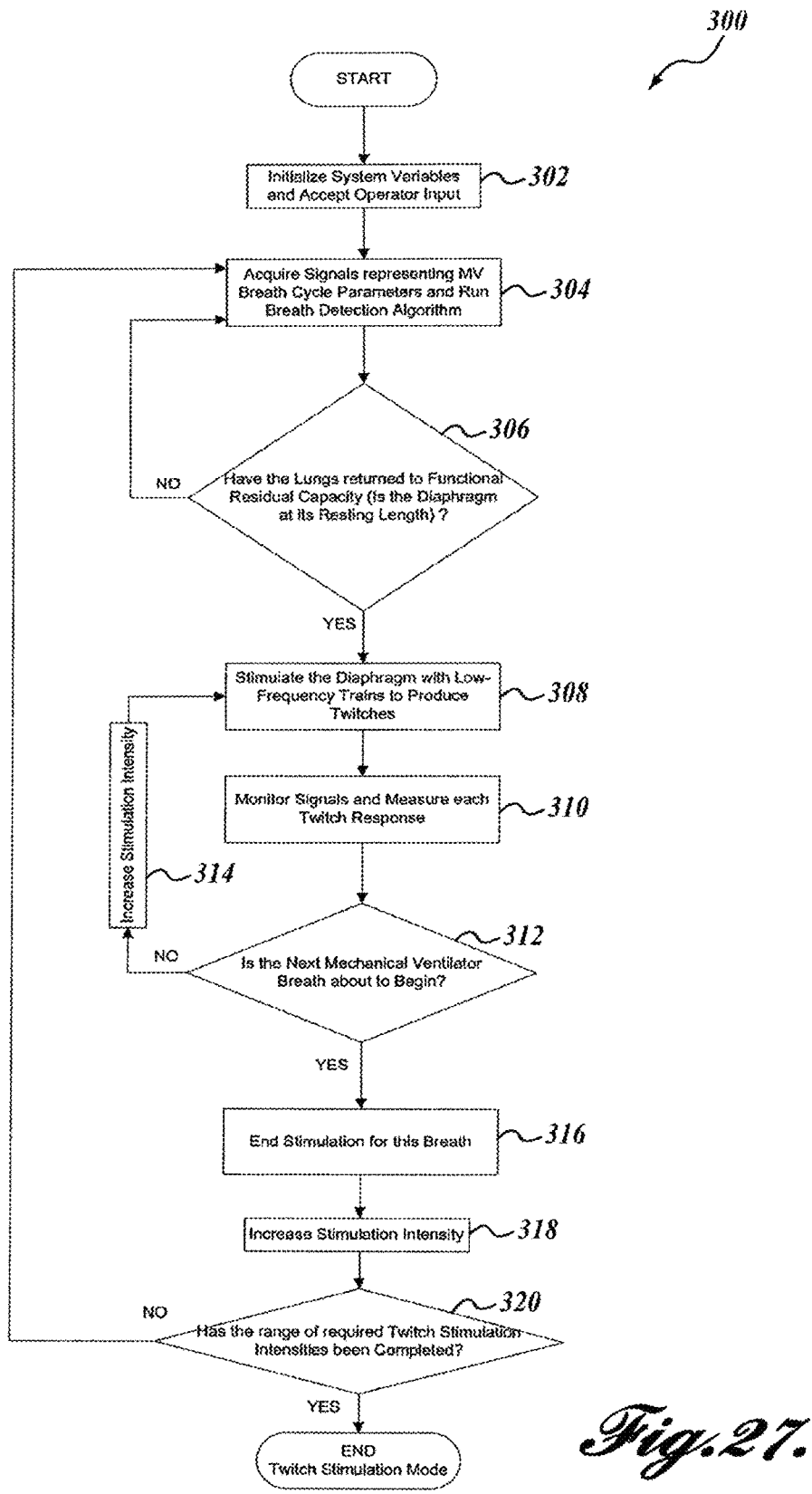
FIG. 27 is one example of an assessment routine carried out by the system of FIG. 1.

FIG. 27 is one example of another assessment routine 300 carried out by the system 20. The assessment routine 300 can be used to guide the placement of endovascular electrodes during normal ventilator operation (i.e., without interference to the ventilator operation or disconnecting the ventilator), and can assess the diaphragm recruitment in response to varying (decreasing or increasing) stimulation charges. When executing the assessment routine 300, the system 20 can administer low-frequency stimulation (such as 1 Hz to 5 Hz), during one or more quiet expiratory periods, to elicit unfused diaphragm contractile responses in the form of single twitches. The charge delivered can be progressively increased to build a complete nerve recruitment curve for each endovascular location, and the operator can define across how many breath periods this stimulation is delivered. The system 20 can analyze this stimulation and response information to algorithmically estimate the best position of the electrodes to stimulate one or both phrenic nerves using minimal amounts of charge (highest degree of efficiency). During this assessment routine, the system 20 can also gather information regarding the relationship between the stimulation train profiles and the corresponding diaphragm response, including diaphragm output (in volume, pressure, or both). Some stimulation parameters that may be obtained include but are not limited to Threshold Pulse Width and Supra-maximal Pulse Width required to recruit each phrenic nerve from appropriate endovascular electrode locations.

Figure 28:
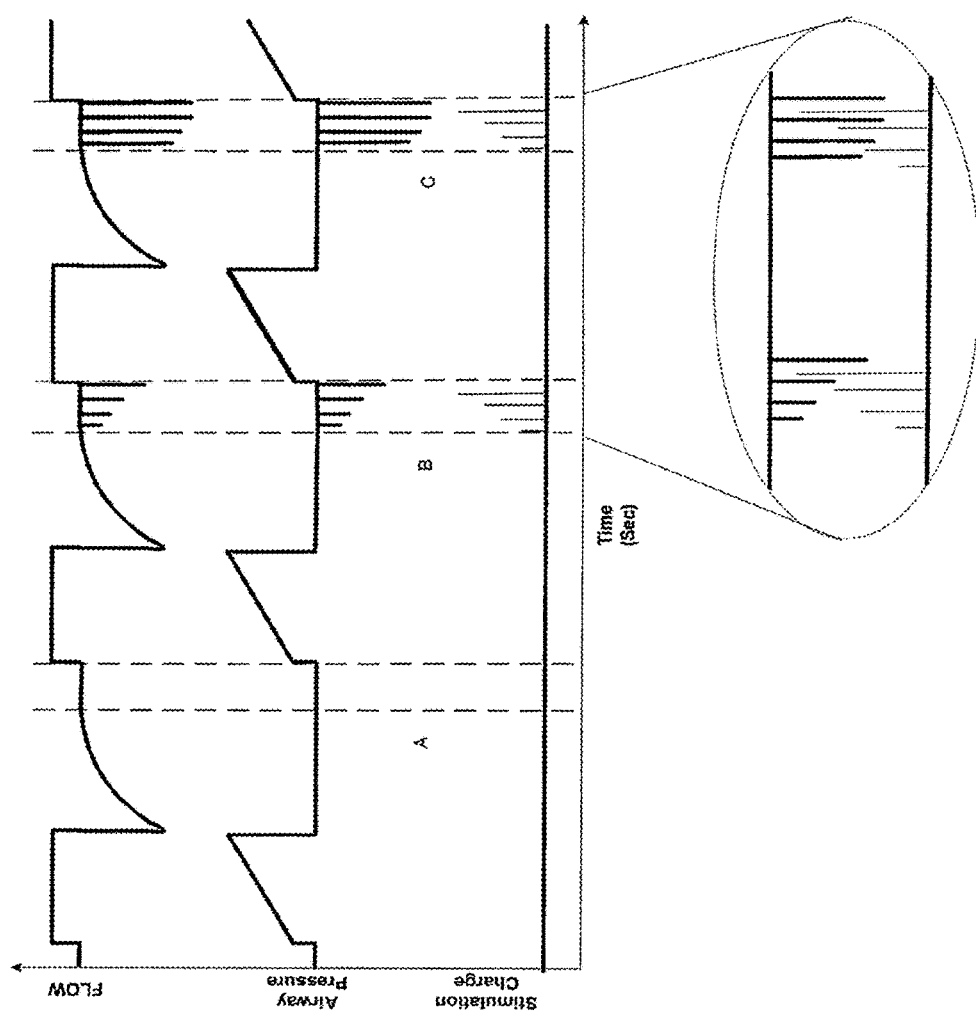
FIG. 28 is a graphical representation of end expiratory pauses, sometimes referred to as quiet periods.

As exemplified in FIG. 28, the stimulation charges in routine 300 can be programmed to periodically occur during periods of baseline flow/volume, which can occur at the end-expiratory pause of the ventilator breath cycle, which can also be referred to as the end-expiratory delay. The benefit of selective stimulation during the end-expiratory pause is that the length of the diaphragm muscle fibers is the same before each stimulus is delivered and thereby establishes standardized conditions for obtaining comparable results. This provides a standard baseline to compare the diaphragm twitch responses and can guide the placement of the endovascular electrodes.

Figure 29:
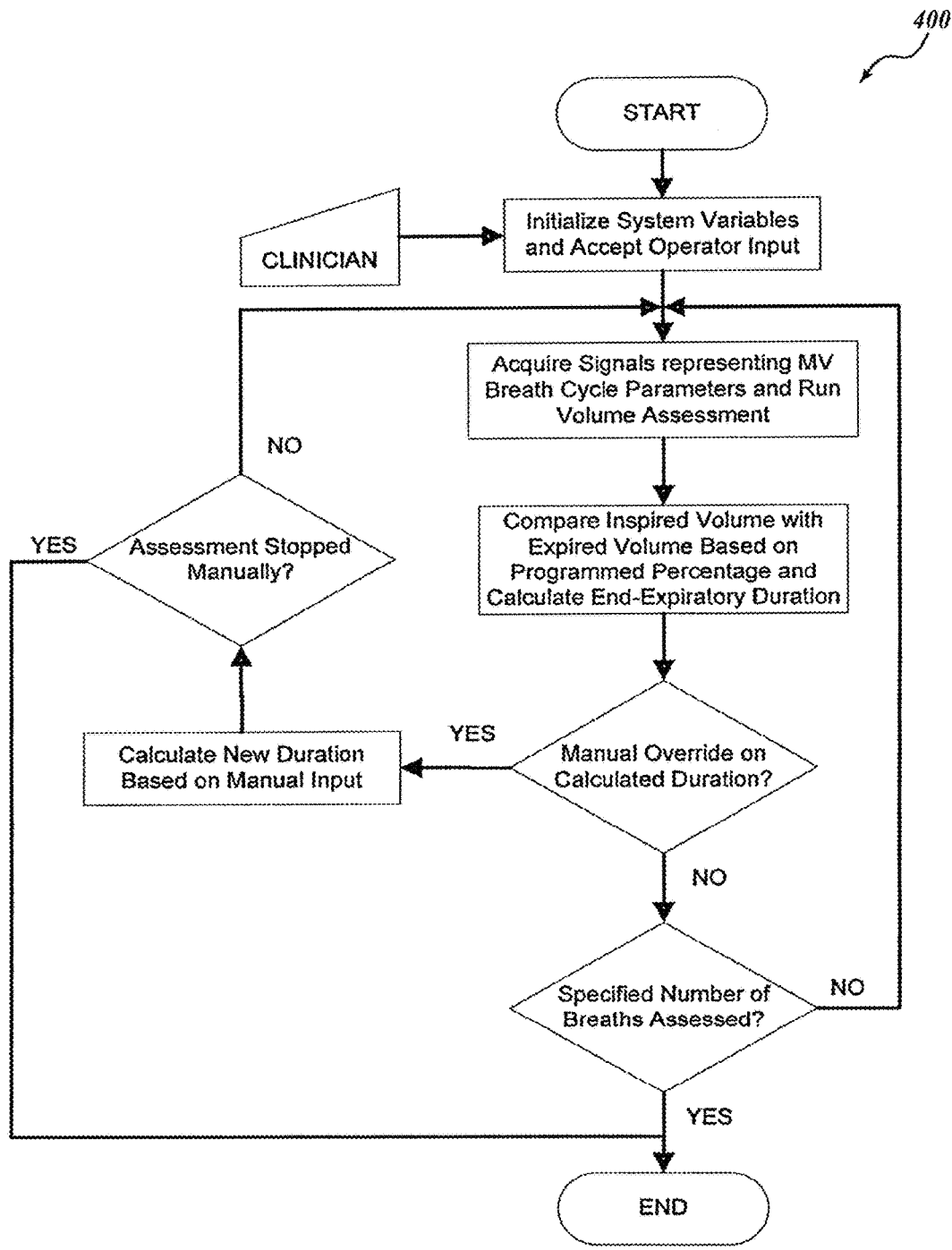
FIG. 29 is one example of a routine for determining the duration of the end-expiratory pause.

This period of zero volume can be determined prior to stimulation to determine the duration of the end-expiratory pause. In that regard, FIG. 29 illustrates one example of a routine 400 for determining the duration of the end-expiratory pause. With this routine, flow data is collected and the end expiratory pause is estimated. In some embodiments, volume of the inspiration and expiration phases are calculated. The point at which the expired volume reaches a user-programmable percentage of the inspiration volume is used as the start time for the end-expiratory pause. In one embodiment, the percentage used as a default is 85% of the inspired volume. In some embodiments, volume is used as it is less influenced by noise than other measures.

While using volume data in some embodiments is one technique, this does not preclude using other measures of the end expiratory phase such as a slope close to zero or simply using a fixed time interval at the end of the expiration phase as the end expiratory pause. In other embodiments, the system 20 can compute relaxation characteristics of the respiratory system, such as Expiratory-Time Constant (i.e. time required to exhale a certain percentage of the air from the lungs) to determine the ideal end-expiratory pause duration and prompt the clinician to adjust the ventilator settings accordingly. At any point in the assessment, the user has the ability to manually override the system and select the duration of the end-expiratory pause as a percentage or absolute value of the measured expiratory phase duration.

Returning to FIG. 27, the assessment routine 300 will be described in some detail. Routine 300 begins at block 302 with the clinician providing the initial system parameters or accepting internal default values, which may include the characteristics of a low-level starting stimulation signal, the maximum stimulation level, the estimated duration of the end-expiratory pause, one or more ventilator parameters, etc. In some embodiments, the characteristics of the low-level starting stimulation signal are based on the estimated duration of the end-expiratory pause.

Next, at block 304, the breath detection algorithm described above can be employed to synchronize the administered stimulation with the end-expiratory pause period of the ventilator 32. For example, the breath detection algorithm can be employed to identify the period of interest during a breath cycle when stimulation can be delivered, as shown in FIG. 28. The diaphragm being a skeletal muscle, its force output changes with its length, as described by its length-tension relationship. Therefore, it is beneficial to stimulate the diaphragm near its resting length, as it provides a standard baseline to compare the diaphragm twitch responses. The resting length of the diaphragm is reached at the end of every expiration phase, as the lungs reach their Functional Residual Capacity. Therefore the inspired and expired volumes can be monitored to provide a non-invasive estimate of when the lungs reach functional residual capacity. In addition, signals from one or more of the sensors 48 and/or sensor 50, such as pressure signals in the form of esophageal or intrathoracic pressure can be used to confirm that the lungs have reached Functional Residual Capacity.

At block 306, based on the aforementioned monitored parameters, a determination is made as to whether the patient's lungs have returned to Functional Residual Capacity as the ventilator carries out the breath cycle. When it is determined that the Functional Residual Capacity is reached, the system 20 administers a starting stimulation signal at block 308 and then monitors and measures the diaphragm response to the administered stimulation at block 310. Signals that can be monitored and measured to quantify the diaphragm response may include, but are not limited to, EMG, Airway Pressure, Airway Flow, Intra-Thoracic Pressure, Pleural Pressure, Central Venous Pressure, Thoracoabdominal motion, various patient impedances, etc.

Next, a determination is made at block 312 as to whether the next ventilator breath is about to begin. Estimated end expiratory pause duration and/or the monitored signals from sensors 48, 50, can aid in this determination. If not, the routine 300 increases the intensity of the stimulation at block 314 and returns to block 308 to administer the increased intensity pulse. If the next ventilator breath is about to begin, stimulation for the current breath is stopped at block 316, the intensity of the current stimulation level can be increased at block 318, and the routine returns to block 304 for another stimulation to be administered in synchrony with the breath cycle. The routine 300 can continue to loop in some embodiments until either the preset range of stimulation intensities has been reached or the maximum stimulation level has been reached.

As the Functional Residual Capacity can change with time, due to factors such as Extrinsic PEEP or Intrinsic PEEP, the system can also employ validation checks to confirm that the functional residual capacity (and therefore the diaphragm resting length) has not changed between breaths. One of the means to perform this validation is to analyze the trend data of the end-expiratory volume, before stimulating the diaphragm.

Figure 30:
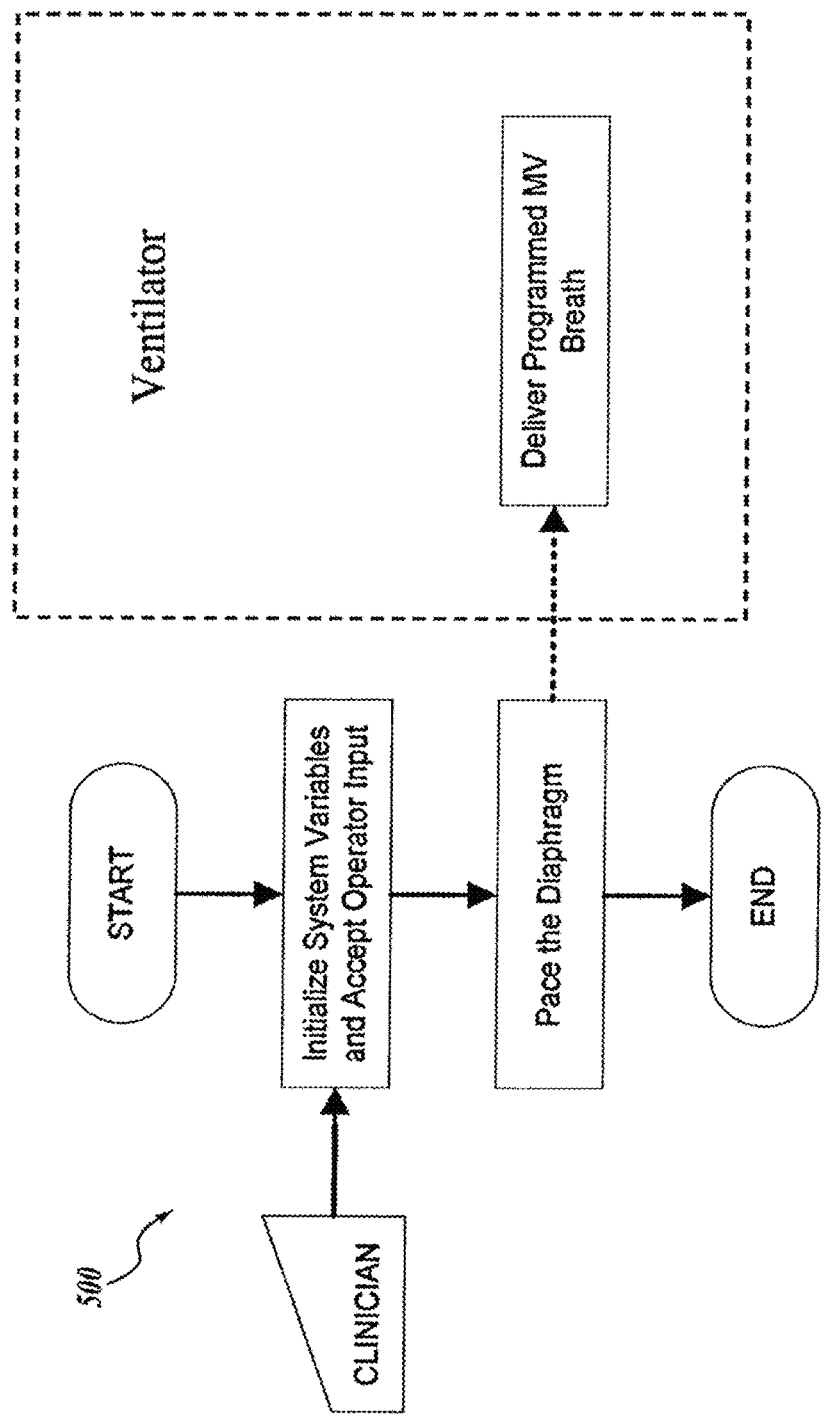
FIG. 30 is a schematic diagram showing one example of a Pacer-Initiated Ventilation Mode that can be carried out by one or more embodiments of the system shown in FIG. 1.
Figure 31:
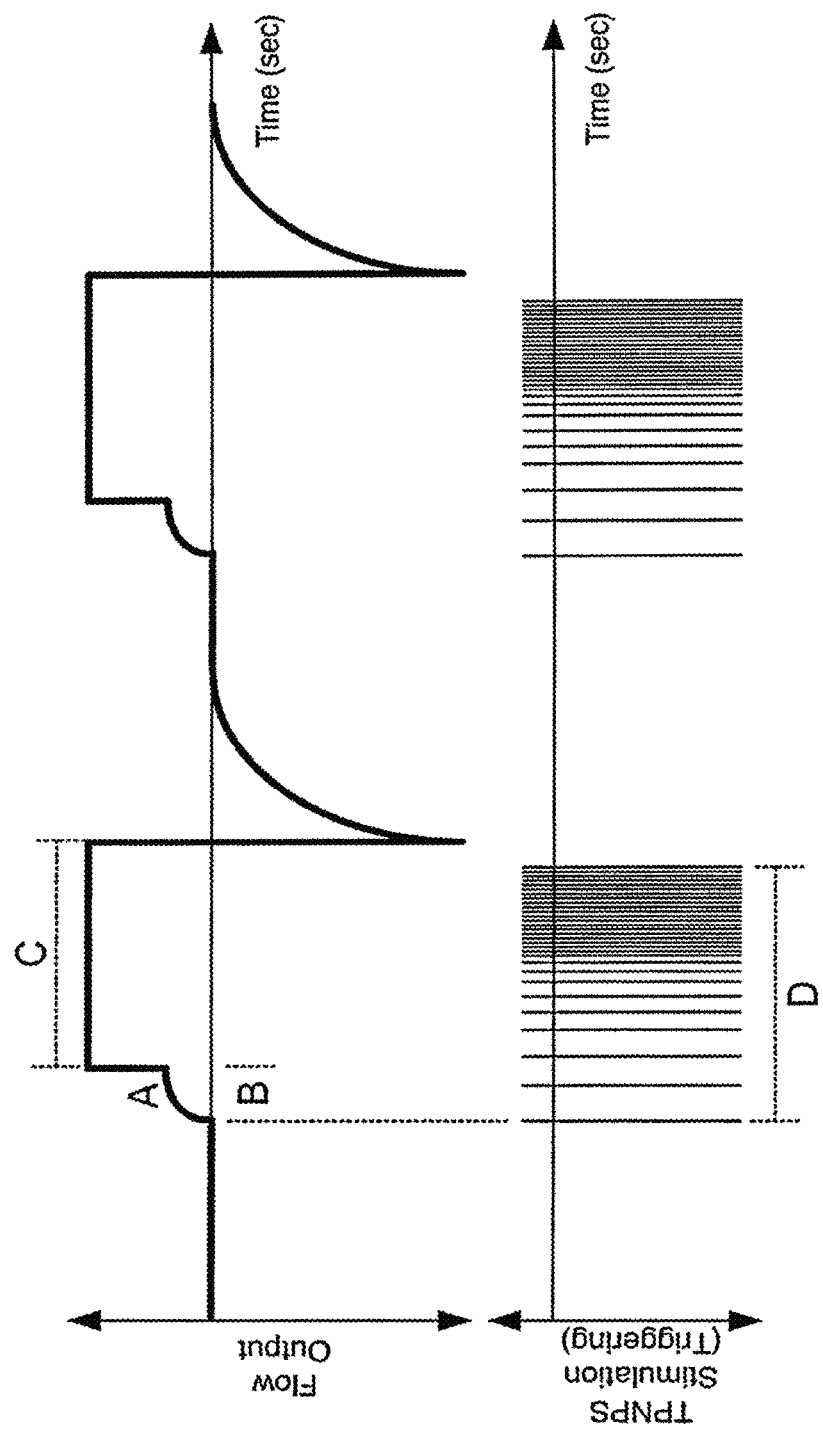
FIG. 31 illustrates the relationship between the pacing system and the ventilator in Pacer-Initiated Ventilation Mode.

The next mode of operation that can be carried out by embodiments of the system 20 includes a Pacer-Initiated Ventilation Mode. FIG. 30 illustrates one example of a routine 500 executed by the system 20 to carry out one or more functions, including the Pacer-Initiated Ventilation Mode. In that regard, many mechanical ventilators have an assist/support mode, whereby ventilation is provided when the patient attempts to breathe on their own. In this embodiment, the system 20 can be programmed to trigger the ventilator 32 working in assistive modes by using stimulation shown by "D" in FIG. 31 (and resultant response from the diaphragm) to mimic spontaneous effort by the patient, as shown in FIG. 31. The ventilator 32 responds to this trigger signal/event and delivers a breath to the patient (based on parameters set by the clinician) shown by "B" in FIG. 31. In effect, the system 20 drives breath delivery from the ventilator 32 (which is opposite from the Ventilator-Initiated Pacing Mode described above) shown by "C" in FIG. 31. In some embodiments, the system 20 does not perform breath detection, and thus, the breath sensor 50 can be omitted. In some embodiments, the breath sensor 50 may be used to carry out various assessment routines and feedback schemes. The system 20 can control the rate of pacing via the programmable parameters such as breath rate (in Breaths per minute), skipped breaths and sigh breaths. Similarly, the Pacer-Initiated Ventilation Mode can also include one or more of the adaptive functionality, closed loop control, diaphragm assessment, successive approximation features described above with reference to Ventilator-Initiated Pacing Mode are also applicable to this mode.

In the Pacer-Initiated Ventilation mode, the system 20 can use feedback to ensure proper diaphragm contribution. Some ventilator modes suitable for this embodiment are Pressure Support Ventilation (PSV), Pressure Regulated Volume Control (PRVC), Proportional Assist Ventilation (PAV) and Adaptive Support Ventilation (ASV).

Figure 32:
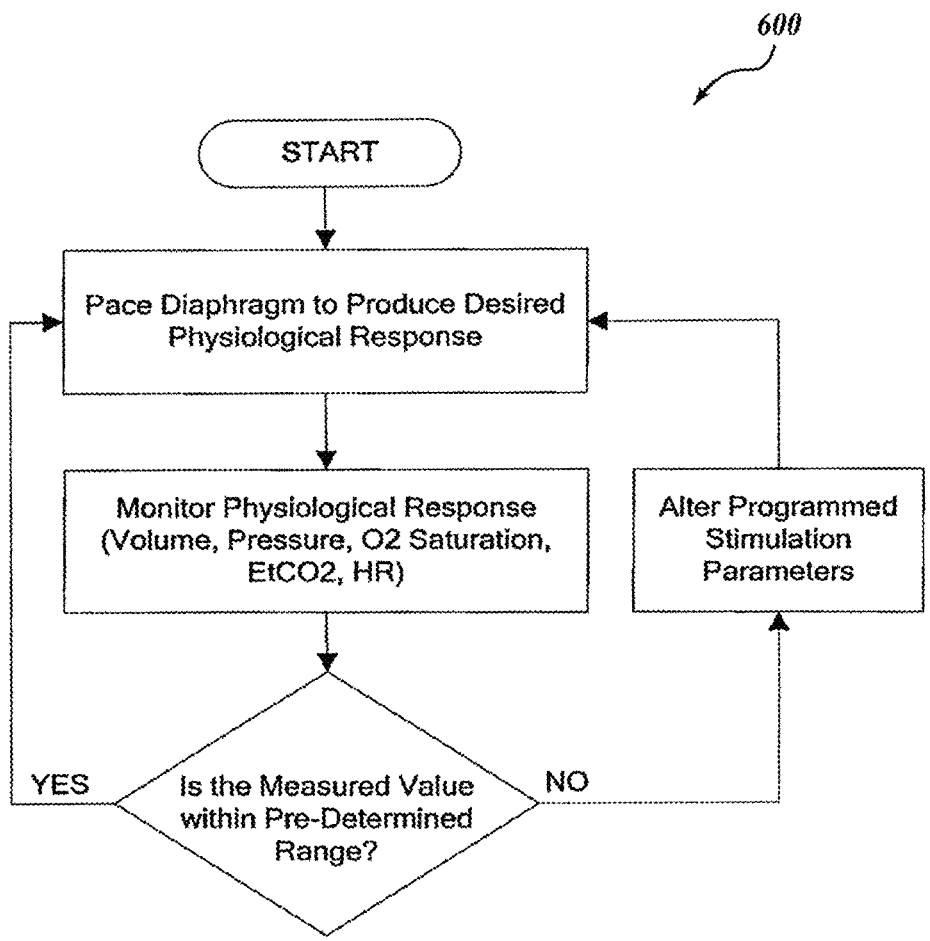
FIG. 32 is a schematic diagram showing one example of a pacing system operating in an Autonomous Mode.
Figure 32A:
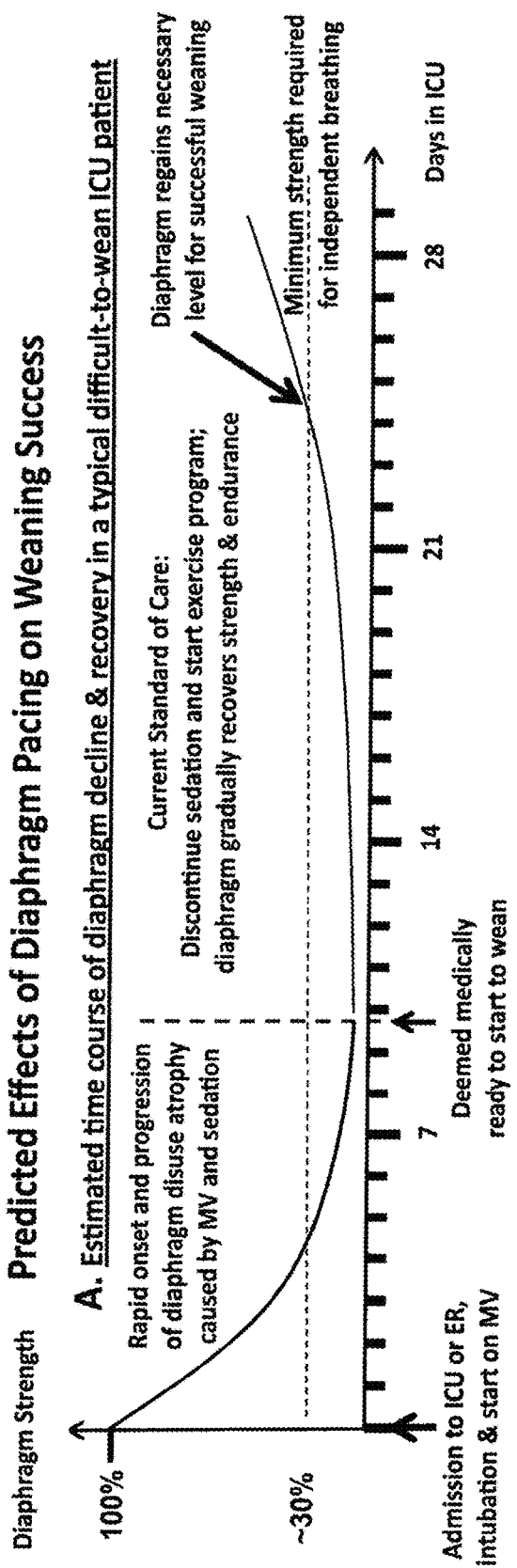

Embodiments of the system 20 can also be operated in Autonomous Mode, or A-Mode. A-Mode is a life-sustaining mode that can operate independently of the ventilator 32. FIG. 32 illustrates one example of a routine 600 executed by the system 20 for carrying out one or more functions, including the Autonomous Mode. In that regard, the A-Mode operates in closed-loop control fashion using feedback from various sensors, such as one or more of the sensors 48, 50. These sensors can be used to monitor physiological variables that can include, but are not limited to: central venous pressure, mixed venous oxygen saturation, heart rate and movement activity levels. A-Mode provides adjustable diaphragmatic pacing to a patient retaining none, some or all of his/her spontaneous breathing and requiring assisted breathing and can automatically adjust to the patient's physiological needs and changed activity levels, as needed.

Although A-mode can be a life-sustaining mode, it may or may not be used in this capacity (i.e. could be interfaced with a backup ventilator). For example, A-Mode may be applicable to patients who are permanently dependent on mechanical ventilators or otherwise in need of continuous pacing from the system 20.

As opposed the embodiments of the system 20 described above for carrying out the Pacer-Initiated Ventilation Mode and the Ventilator-Initiated Pacing Mode, embodiments of the system 20 carrying out the A-Mode can be totally implanted under the skin of the patient in the upper chest area. In this regard, the system 20 is powered by a power storage source, such as either primary or rechargeable implantable batteries, and may be integrated with other implantable devices that support heart or other functions to a patient.

As shown in the embodiment of FIG. 32, the system 20 operating in A-Mode involves a closed-loop operation to autonomously pace the diaphragm. This mode may make use of any patient response signal (feedback) that will help indicate that pacing is required; these signals include, but are not limited to: oxygen saturation, end-tidal CO2 (EtCO2), airflow, heart rate, movement-detecting accelerometer signals, etc. Pacing is administered continuously in A-mode, and an algorithm is used to detect and/or modify physiological response signals to determine whether a change in stimulation pattern, frequency, breath rate, intensity, type, and/or shape profile is required to elicit the expected response.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A medical device, comprising:
a first electrode pair configured to be positioned proximate at least one phrenic nerve within a patient;
a stimulator coupled to the first electrode pair, the stimulator being configured to:
calculate a level of work to be expended during breathing by the patient;
calculate a desired electrical stimulation based on the calculated level of work; and
deliver the calculated desired electrical stimulation to the first electrode pair to at least partially activate the patient's diaphragm; and
a sensor configured to provide a flow measurement to the stimulator;
wherein the stimulator is configured to determine when inspiration of a given breath is occurring based on the flow measurement from the sensor, and deliver the electrical stimulation during the determined inspiration; and
wherein the stimulator is configured to end the electrical stimulation before initiation of a subsequent breath.

2. The medical device of claim 1, wherein the stimulator is configured to end the electrical stimulation before initiation of expiration during the given breath.

3. The medical device of claim 1, wherein the stimulator is configured to end the electrical stimulation at initiation of expiration during the given breath.

4. The medical device of claim 1, wherein the stimulator is configured to end the electrical stimulation after initiation of expiration during the given breath.

5. The medical device of claim 1, wherein the medical device includes a plurality of pairs of electrodes, including the first electrode pair, and the stimulator is configured to deliver the electrical stimulation with one of the plurality of pairs of electrodes.

6. The medical device of claim 1, wherein the stimulator is in wired communication with the first electrode pair.

7. The medical device of claim 1, wherein the first electrode pair is disposed on a catheter.

8. The medical device of claim 7, wherein the electrodes of the first electrode pair are longitudinally spaced from one another on the catheter.

9. The medical device of claim 1, wherein the first electrode pair is configured to be placed within a blood vessel of the patient.

10. The medical device of claim 1, wherein the first electrode pair includes an anodal electrode and a cathodal electrode.

11. The medical device of claim 1, further including a second electrode pair, wherein the stimulator is configured to deliver electrical stimulation to the second electrode pair to at least partially activate the patient's diaphragm.

12. The medical device of claim 1, wherein the sensor is configured to interface with a breathing circuit of a mechanical ventilator.

13. The medical device of claim 1, wherein the sensor is for coupling to a mechanical ventilator, and the sensor is external to the mechanical ventilator.

14. The medical device of claim 1, wherein the flow measurement includes inspired airflow and/or expired airflow.

15. The medical device of claim 1, wherein the stimulator is configured to deliver stimulation during the given breath, and not during the subsequent breath.

16. A medical device, comprising:
one or more electrodes configured to be positioned under skin of a patient proximate to at least one phrenic nerve within the patient;
a sensor configured to measure airflow into and out of the patient; and
a stimulator connected to the one or more electrodes and to the sensor, the stimulator configured to:
determine when inspiration of a given breath is occurring based on input from the sensor;
calculate a level of work to be expended during breathing by the patient;
calculate a desired electrical stimulation based on the calculated level of work;
deliver the calculated desired electrical stimulation to the one or more electrodes to at least partially activate the patient's diaphragm during the determined inspiration; and
cease the electrical stimulation before initiation of expiration during the given breath.

17. The medical device of claim 16, wherein the one or more electrodes includes an anodal electrode and a cathodal electrode.

* * * * *